(12) United States Patent
Kleiner et al.

(10) Patent No.: US 9,186,193 B2
(45) Date of Patent: *Nov. 17, 2015

(54) FUSION CAGE WITH COMBINED BIOLOGICAL DELIVERY SYSTEM

(71) Applicant: Spinal Surgical Strategies, LLC, Denver, CO (US)

(72) Inventors: Jeffrey B. Kleiner, Denver, CO (US); Edward John Grimberg, Jr., Golden, CO (US)

(73) Assignee: Spinal Surgical Strategies, LLC, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/263,963

(22) Filed: Apr. 28, 2014

(65) Prior Publication Data

US 2015/0148907 A1    May 28, 2015

Related U.S. Application Data

(63) Continuation-in-part of application No. 14/088,148, filed on Nov. 22, 2013, now Pat. No. 8,709,088, which is a continuation of application No. 13/947,255, filed on Jul. 22, 2013, now Pat. No. 8,685,031, which is a
(Continued)

(51) Int. Cl.
*A61B 17/88* (2006.01)
*A61F 2/46* (2006.01)
(Continued)

(52) U.S. Cl.
CPC ......... *A61B 17/8822* (2013.01); *A61B 17/8816* (2013.01); *A61F 2/447* (2013.01); *A61F 2/4455* (2013.01); *A61F 2/4601* (2013.01); *A61F 2/4611* (2013.01); *A61F 2/30767* (2013.01);
(Continued)

(58) Field of Classification Search
CPC .................. A61B 17/8819; A61B 17/8822
See application file for complete search history.

(56) References Cited

U.S. PATENT DOCUMENTS

D30,951 S    6/1899  Saint Cyr, Jr.
1,867,624 A  7/1932  Hoffman
(Continued)

FOREIGN PATENT DOCUMENTS

FR    2790946       9/2000
JP    H09-327468   12/1997
(Continued)

OTHER PUBLICATIONS

U.S. Appl. No. 13/168,611, filed Jun. 24, 2011, Kleiner.
(Continued)

*Primary Examiner* — Christian Sevilla
(74) *Attorney, Agent, or Firm* — Sheridan Ross P.C.

(57) ABSTRACT

The present invention relates to an apparatus and method for near-simultaneous and integrated delivery of bone graft material during the placement of surgical cages or other medical implants in a patient's spine. The integrated fusion cage and graft delivery device according to various embodiments delivers and disperses biologic material through a fusion cage to a disc space and, without withdrawal from the surgical site, may selectably detach the fusion cage for deposit to the same disc space. The integrated fusion cage and graft delivery device is formed such that a hollow tube and plunger selectively and controllably place bone graft material and a fusion cage in or adjacent to the bone graft receiving area.

17 Claims, 36 Drawing Sheets

Related U.S. Application Data continuation-in-part of application No. 13/714,971, filed on Dec. 14, 2012, which is a continuation-in-part of application No. 13/367,295, filed on Feb. 6, 2012, now Pat. No. 9,060,877, which is a continuation-in-part of application No. 12/886,452, filed on Sep. 20, 2010, now Pat. No. 8,906,028.

(60) Provisional application No. 61/243,664, filed on Sep. 18, 2009.

(51) Int. Cl.
 *A61F 2/44* (2006.01)
 *A61F 2/30* (2006.01)
 *A61F 2/28* (2006.01)

(52) U.S. Cl.
 CPC . *A61F 2002/2817* (2013.01); *A61F 2002/2835* (2013.01); *A61F 2002/30013* (2013.01); *A61F 2002/3071* (2013.01); *A61F 2002/3093* (2013.01); *A61F 2002/30153* (2013.01); *A61F 2002/30224* (2013.01); *A61F 2002/30235* (2013.01); *A61F 2002/30601* (2013.01); *A61F 2002/30785* (2013.01); *A61F 2002/30787* (2013.01); *A61F 2002/30828* (2013.01); *A61F 2002/30878* (2013.01); *A61F 2002/30904* (2013.01); *A61F 2002/4475* (2013.01); *A61F 2002/4602* (2013.01); *A61F 2002/469* (2013.01); *A61F 2002/4627* (2013.01); *A61F 2002/4693* (2013.01); *A61F 2002/4694* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01)

(56) References Cited

U.S. PATENT DOCUMENTS

| | | | |
|---|---|---|---|
| 2,520,464 A | 8/1950 | Hubner |
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A | 7/1981 | Solomon |
| 4,338,925 A | 7/1982 | Miller |
| 4,430,062 A | 2/1984 | Henrichsen et al. |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,743,256 A | 5/1988 | Brantigan |
| 4,877,399 A | 10/1989 | Frank et al. |
| 4,925,924 A | 5/1990 | Silver et al. |
| D309,499 S | 7/1990 | Bowman et al. |
| D312,309 S | 11/1990 | Michelson |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| D351,022 S | 9/1994 | Saito |
| 5,354,292 A | 10/1994 | Braeuer et al. |
| 5,395,372 A | 3/1995 | Holt et al. |
| 5,425,772 A | 6/1995 | Brantigan |
| D360,689 S | 7/1995 | Giampapa |
| 5,431,658 A | 7/1995 | Moskovich |
| 5,443,514 A | 8/1995 | Steffee |
| D364,462 S | 11/1995 | Michelson |
| 5,520,611 A | 5/1996 | Rao et al. |
| D370,531 S | 6/1996 | Ash et al. |
| 5,527,312 A | 6/1996 | Ray |
| D372,311 S | 7/1996 | Koros et al. |
| 5,531,749 A | 7/1996 | Michelson |
| D372,781 S | 8/1996 | Reif |
| 5,549,607 A | 8/1996 | Olson et al. |
| 5,554,191 A | 9/1996 | Lahille et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,655 A | 9/1997 | Laboureau et al. |
| 5,665,122 A | 9/1997 | Kambin |
| 5,683,464 A | 11/1997 | Wagner et al. |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| 5,741,253 A | 4/1998 | Michelson |
| 5,752,969 A | 5/1998 | Cunci et al. |
| 5,762,629 A | 6/1998 | Kambin |
| 5,779,642 A | 7/1998 | Nightengale |
| 5,782,919 A | 7/1998 | Zdeblick et al. |
| 5,797,918 A | 8/1998 | McGuire et al. |
| 5,836,948 A | 11/1998 | Zucherman et al. |
| 5,836,958 A | 11/1998 | Ralph |
| 5,860,973 A | 1/1999 | Michelson |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,904,718 A | 5/1999 | Jefferies |
| 5,906,616 A | 5/1999 | Pavlov et al. |
| 5,925,051 A | 7/1999 | Mikhail |
| 5,925,056 A | 7/1999 | Thomas et al. |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,989,257 A | 11/1999 | Tidwell et al. |
| 5,997,895 A | 12/1999 | Narotam et al. |
| 6,004,191 A | 12/1999 | Schur et al. |
| 6,004,326 A | 12/1999 | Castro et al. |
| 6,013,028 A | 1/2000 | Jho et al. |
| 6,019,765 A | 2/2000 | Thornhill et al. |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,059,829 A | 5/2000 | Schlapfer et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,123,705 A | 9/2000 | Michelson |

(56) References Cited

U.S. PATENT DOCUMENTS

| | | |
|---|---|---|
| 6,136,001 A | 10/2000 | Michelson |
| 6,142,998 A | 11/2000 | Smith et al. |
| 6,146,420 A | 11/2000 | McKay |
| 6,149,096 A | 11/2000 | Hartley |
| 6,152,871 A | 11/2000 | Foley et al. |
| 6,159,211 A | 12/2000 | Boriani et al. |
| 6,159,245 A | 12/2000 | Meriwether et al. |
| 6,180,085 B1 | 1/2001 | Achilefu |
| 6,200,322 B1 | 3/2001 | Branch et al. |
| 6,209,886 B1 | 4/2001 | Estes et al. |
| 6,216,573 B1 | 4/2001 | Moutafis et al. |
| 6,224,599 B1 | 5/2001 | Baynham et al. |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,290,724 B1 | 9/2001 | Marino |
| 6,299,613 B1 | 10/2001 | Ogilvie et al. |
| 6,309,395 B1 | 10/2001 | Smith et al. |
| 6,325,805 B1 | 12/2001 | Ogilvie et al. |
| 6,328,738 B1 | 12/2001 | Suddaby |
| 6,336,928 B1 | 1/2002 | Guerin et al. |
| 6,342,074 B1 | 1/2002 | Simpson |
| 6,364,880 B1 | 4/2002 | Michelson |
| 6,375,635 B1 | 4/2002 | Moutafis et al. |
| 6,387,096 B1 | 5/2002 | Hyde, Jr. |
| 6,409,765 B1 | 6/2002 | Bianchi et al. |
| 6,436,101 B1 | 8/2002 | Hamada |
| 6,451,017 B1 | 9/2002 | Moutafis et al. |
| 6,454,806 B1 | 9/2002 | Cohen et al. |
| 6,467,556 B2 | 10/2002 | Alsruhe |
| D467,657 S | 12/2002 | Scribner |
| 6,500,206 B1 | 12/2002 | Bryan |
| 6,511,493 B1 | 1/2003 | Moutafis et al. |
| D469,871 S | 2/2003 | Sand |
| 6,520,976 B1 | 2/2003 | Gage |
| 6,524,318 B1 | 2/2003 | Longhini et al. |
| 6,565,574 B2 | 5/2003 | Michelson |
| 6,569,201 B2 | 5/2003 | Moumene et al. |
| 6,613,091 B1 | 9/2003 | Zdeblick et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,695,882 B2 | 2/2004 | Bianchi et al. |
| 6,699,288 B2 | 3/2004 | Moret |
| 6,709,438 B2 | 3/2004 | Dixon et al. |
| 6,719,760 B2 | 4/2004 | Dorchak et al. |
| 6,719,795 B1 | 4/2004 | Cornwall et al. |
| 6,730,125 B1 | 5/2004 | Lin |
| 6,743,257 B2 | 6/2004 | Castro |
| 6,746,487 B2 | 6/2004 | Scifert et al. |
| 6,764,491 B2 | 7/2004 | Frey et al. |
| 6,770,074 B2 | 8/2004 | Michelson |
| 6,773,437 B2 | 8/2004 | Ogilvie et al. |
| 6,800,093 B2 | 10/2004 | Nicholson et al. |
| 6,824,565 B2 | 11/2004 | Muhanna et al. |
| 6,830,574 B2 | 12/2004 | Heckele et al. |
| 6,852,126 B2 | 2/2005 | Ahlgren |
| 6,869,430 B2 | 3/2005 | Balbierz et al. |
| 6,890,728 B2 | 5/2005 | Dolecek et al. |
| 6,899,712 B2 | 5/2005 | Moutafis et al. |
| 6,923,792 B2 | 8/2005 | Staid et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,974,480 B2 | 12/2005 | Messerli et al. |
| 6,991,653 B2 | 1/2006 | White et al. |
| 6,994,728 B2 | 2/2006 | Zubok et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,033,317 B2 | 4/2006 | Pruitt |
| 7,041,136 B2 | 5/2006 | Goble et al. |
| 7,066,961 B2 | 6/2006 | Hichelson |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,128,760 B2 | 10/2006 | Michelson |
| 7,135,043 B2 | 11/2006 | Nakahara et al. |
| 7,182,782 B2 | 2/2007 | Kirschman |
| 7,204,825 B2 | 4/2007 | Cimino et al. |
| 7,207,992 B2 | 4/2007 | Ritland |
| 7,211,112 B2 | 5/2007 | Baynham et al. |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,288,093 B2 | 10/2007 | Michelson |
| 7,316,070 B2 | 1/2008 | Green |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,421,772 B2 | 9/2008 | Gao et al. |
| 7,429,270 B2 | 9/2008 | Baumgartner et al. |
| D579,562 S | 10/2008 | Anderson et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| D582,552 S | 12/2008 | Berberich |
| 7,461,803 B2 | 12/2008 | Boerner |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D590,945 S | 4/2009 | Berberich |
| 7,513,901 B2 | 4/2009 | Scifert et al. |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| D594,119 S | 6/2009 | Berberich et al. |
| 7,553,320 B2 | 6/2009 | Molz, IV et al. |
| D597,669 S | 8/2009 | Petersen |
| D598,096 S | 8/2009 | Petersen |

(56) References Cited

U.S. PATENT DOCUMENTS

| | | |
|---|---|---|
| D599,015 S | 8/2009 | Petersen |
| 7,578,820 B2 | 8/2009 | Moore et al. |
| D600,806 S | 9/2009 | Horton et al. |
| D601,251 S | 9/2009 | Horton et al. |
| 7,582,058 B1 | 9/2009 | Miles et al. |
| 7,582,107 B2 | 9/2009 | Trail et al. |
| 7,595,043 B2 | 9/2009 | Hedrick et al. |
| D603,502 S | 11/2009 | Petersen |
| 7,615,078 B2 | 11/2009 | White et al. |
| 7,618,423 B1 | 11/2009 | Valentine et al. |
| 7,625,374 B2 | 12/2009 | Branch et al. |
| 7,632,276 B2 | 12/2009 | Fishbein |
| D608,001 S | 1/2010 | Reardon et al. |
| 7,655,027 B2 | 2/2010 | Michelson |
| 7,658,766 B2 | 2/2010 | Melkent et al. |
| 7,671,014 B2 | 3/2010 | Beals et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,699,852 B2 | 4/2010 | Frankel et al. |
| 7,708,761 B2 | 5/2010 | Petersen |
| 7,717,685 B2 | 5/2010 | Moutafis et al. |
| 7,722,530 B2 | 5/2010 | Davison |
| 7,722,613 B2 | 5/2010 | Sutterlin et al. |
| 7,723,291 B2 | 5/2010 | Beals et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| D620,108 S | 7/2010 | Eitenmueller et al. |
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Iott et al. |
| 7,758,644 B2 | 7/2010 | Trieu |
| 7,758,648 B2 | 7/2010 | Castleman et al. |
| 7,763,025 B2 | 7/2010 | Assell et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| 7,819,921 B2 | 10/2010 | Grotz |
| D627,460 S | 11/2010 | Horton |
| 7,824,328 B2 | 11/2010 | Gattani et al. |
| 7,824,332 B2 | 11/2010 | Fakhrai |
| 7,824,410 B2 | 11/2010 | Simonson et al. |
| 7,824,703 B2 | 11/2010 | Scifert et al. |
| 7,828,804 B2 | 11/2010 | Li et al. |
| 7,828,845 B2 | 11/2010 | Estes et al. |
| 7,828,849 B2 | 11/2010 | Lim |
| 7,837,713 B2 | 11/2010 | Petersen |
| 7,837,732 B2 | 11/2010 | Zucherman et al. |
| D628,694 S | 12/2010 | Donnez |
| D629,896 S | 12/2010 | Horton |
| 7,846,210 B2 | 12/2010 | Perez-Cruet et al. |
| 7,850,733 B2 | 12/2010 | Baynham et al. |
| 7,850,735 B2 | 12/2010 | Eisermann et al. |
| 7,850,736 B2 | 12/2010 | Heinz et al. |
| D631,156 S | 1/2011 | Halder et al. |
| 7,867,277 B1 | 1/2011 | Tohmeh |
| 7,897,164 B2 | 3/2011 | Scifert |
| 7,897,564 B2 | 3/2011 | Beals et al. |
| 7,905,840 B2 | 3/2011 | Pimenta et al. |
| 7,905,886 B1 | 3/2011 | Curran et al. |
| 7,918,891 B1 | 4/2011 | Curran et al. |
| 7,922,766 B2 | 4/2011 | Grob et al. |
| 7,927,361 B2 | 4/2011 | Oliver et al. |
| D637,721 S | 5/2011 | Horton |
| 7,935,124 B2 | 5/2011 | Frey et al. |
| 7,938,857 B2 | 5/2011 | Garcia-Bengochea et al. |
| 7,939,092 B2 | 5/2011 | McKay et al. |
| 7,951,107 B2 | 5/2011 | Staid et al. |
| 7,964,208 B2 | 6/2011 | Spagnoli et al. |
| D641,872 S | 7/2011 | Solingen et al. |
| D641,873 S | 7/2011 | Solingen et al. |
| D641,874 S | 7/2011 | Solingen et al. |
| D642,268 S | 7/2011 | Qureshi |
| 7,985,256 B2 | 7/2011 | Grotz et al. |
| D643,921 S | 8/2011 | Davila |
| D647,202 S | 10/2011 | Scifert |
| 8,080,521 B2 | 12/2011 | Beals et al. |
| 8,088,163 B1 | 1/2012 | Kleiner |
| D655,414 S | 3/2012 | Cuschieri et al. |
| D656,610 S | 3/2012 | Kleiner |
| 8,148,326 B2 | 4/2012 | Beals et al. |
| D660,428 S | 5/2012 | Hohl |
| 8,198,238 B2 | 6/2012 | Beals et al. |
| 8,246,572 B2 | 8/2012 | Cantor et al. |
| D667,542 S | 9/2012 | Kleiner |
| 8,277,510 B2 | 10/2012 | Kleiner |
| 8,292,960 B2 | 10/2012 | Kleiner |
| 8,293,232 B2 | 10/2012 | Beals et al. |
| 8,361,152 B2 | 1/2013 | McCormack et al. |

(56) References Cited

U.S. PATENT DOCUMENTS

| | | |
|---|---|---|
| 8,366,748 B2 | 2/2013 | Kleiner |
| D692,133 S | 10/2013 | Steinwachs et al. |
| D696,399 S | 12/2013 | Kleiner |
| D700,322 S | 2/2014 | Kleiner |
| 8,685,031 B2 | 4/2014 | Kleiner |
| 8,709,088 B2 | 4/2014 | Kleiner et al. |
| 8,808,305 B2 | 8/2014 | Kleiner |
| 8,834,472 B2 | 9/2014 | McCormack et al. |
| 8,932,295 B1 | 1/2015 | Greenhalgh |
| 8,945,137 B1 | 2/2015 | Greenhalgh et al. |
| 2002/0010472 A1 | 1/2002 | Kuslich et al. |
| 2002/0049448 A1 | 4/2002 | Sand et al. |
| 2002/0058947 A1 | 5/2002 | Hochschuler et al. |
| 2002/0099377 A1 | 7/2002 | Zucherman et al. |
| 2002/0116006 A1 | 8/2002 | Cohen |
| 2003/0083748 A1 | 5/2003 | Lee et al. |
| 2003/0149482 A1 | 8/2003 | Michelson |
| 2003/0171812 A1 | 9/2003 | Grunberg et al. |
| 2003/0229358 A1 | 12/2003 | Errico et al. |
| 2004/0002713 A1 | 1/2004 | Olson et al. |
| 2004/0024466 A1 | 2/2004 | Heerklotz et al. |
| 2004/0073314 A1 | 4/2004 | White et al. |
| 2004/0087956 A1 | 5/2004 | Weikel et al. |
| 2004/0133211 A1 | 7/2004 | Raskin et al. |
| 2004/0133217 A1 | 7/2004 | Watschke |
| 2004/0143330 A1 | 7/2004 | Sazy |
| 2004/0148027 A1 | 7/2004 | Errico et al. |
| 2004/0153158 A1 | 8/2004 | Errico et al. |
| 2004/0167532 A1 | 8/2004 | Olson, Jr. et al. |
| 2004/0176853 A1 | 9/2004 | Sennett et al. |
| 2004/0215201 A1* | 10/2004 | Lieberman ............ 606/93 |
| 2004/0230211 A1 | 11/2004 | Moutafis et al. |
| 2005/0070900 A1 | 3/2005 | Serhan et al. |
| 2005/0096601 A1 | 5/2005 | Doyle |
| 2005/0112091 A1 | 5/2005 | DiMauro et al. |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0165405 A1 | 7/2005 | Tsou |
| 2005/0216002 A1 | 9/2005 | Simonson |
| 2005/0216018 A1 | 9/2005 | Sennett |
| 2005/0251146 A1 | 11/2005 | Martz et al. |
| 2005/0251257 A1 | 11/2005 | Mitchell et al. |
| 2005/0261781 A1 | 11/2005 | Sennett et al. |
| 2005/0283150 A1 | 12/2005 | Moutafis et al. |
| 2006/0004167 A1 | 1/2006 | Alamin et al. |
| 2006/0004367 A1 | 1/2006 | Alamin et al. |
| 2006/0015184 A1 | 1/2006 | Winterbottom et al. |
| 2006/0058585 A1 | 3/2006 | Oberlaender et al. |
| 2006/0058807 A1 | 3/2006 | Landry et al. |
| 2006/0100304 A1 | 5/2006 | Vresilovic et al. |
| 2006/0111779 A1 | 5/2006 | Petersen |
| 2006/0111780 A1 | 5/2006 | Petersen |
| 2006/0116770 A1 | 6/2006 | White et al. |
| 2006/0122597 A1 | 6/2006 | Jones et al. |
| 2006/0154366 A1 | 7/2006 | Brown et al. |
| 2006/0155170 A1 | 7/2006 | Hanson et al. |
| 2006/0167461 A1 | 7/2006 | Hawkins et al. |
| 2006/0190081 A1 | 8/2006 | Kraus |
| 2006/0229550 A1 | 10/2006 | Staid et al. |
| 2006/0247650 A1 | 11/2006 | Yerby et al. |
| 2006/0247791 A1 | 11/2006 | McKay et al. |
| 2006/0264808 A1 | 11/2006 | Staid et al. |
| 2006/0264964 A1 | 11/2006 | Scifert et al. |
| 2007/0003598 A1 | 1/2007 | Trieu |
| 2007/0043376 A1 | 2/2007 | Leatherbury et al. |
| 2007/0043442 A1 | 2/2007 | Abernathie |
| 2007/0067034 A1 | 3/2007 | Chirico et al. |
| 2007/0073110 A1 | 3/2007 | Larson et al. |
| 2007/0073294 A1 | 3/2007 | Chin et al. |
| 2007/0088007 A1 | 4/2007 | Ng |
| 2007/0093850 A1 | 4/2007 | Harris et al. |
| 2007/0123985 A1 | 5/2007 | Errico et al. |
| 2007/0172790 A1 | 7/2007 | Doucette, Jr. et al. |
| 2007/0185496 A1 | 8/2007 | Beckman et al. |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |
| 2007/0213826 A1 | 9/2007 | Smith et al. |
| 2007/0225219 A1 | 9/2007 | Boden et al. |
| 2007/0225811 A1 | 9/2007 | Scifert et al. |
| 2007/0242869 A1 | 10/2007 | Luo et al. |
| 2007/0250166 A1 | 10/2007 | McKay |
| 2007/0264300 A1 | 11/2007 | Scifert et al. |
| 2007/0265632 A1 | 11/2007 | Scifert et al. |
| 2007/0270951 A1 | 11/2007 | Davis et al. |
| 2007/0276406 A1 | 11/2007 | Mahoney et al. |
| 2007/0288007 A1 | 12/2007 | Burkus et al. |
| 2007/0293948 A1 | 12/2007 | Bagga et al. |
| 2008/0003255 A1 | 1/2008 | Kerr et al. |
| 2008/0009929 A1 | 1/2008 | Harris et al. |
| 2008/0033440 A1 | 2/2008 | Moskowitz et al. |
| 2008/0058606 A1 | 3/2008 | Miles et al. |
| 2008/0071284 A1* | 3/2008 | Lechmann et al. ............ 606/99 |
| 2008/0086142 A1* | 4/2008 | Kohm et al. ............ 606/92 |
| 2008/0125856 A1 | 5/2008 | Perez-Cruet et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0154381 A1 | 6/2008 | Parrish |
| 2008/0172127 A1 | 7/2008 | Perez-Cruet et al. |
| 2008/0195058 A1 | 8/2008 | Moutafis et al. |
| 2008/0228225 A1 | 9/2008 | Trautwein et al. |
| 2008/0243126 A1 | 10/2008 | Gutierrez et al. |
| 2008/0249569 A1 | 10/2008 | Waugh et al. |
| 2008/0255564 A1 | 10/2008 | Michelson |
| 2008/0255666 A1 | 10/2008 | Fisher et al. |
| 2008/0260598 A1 | 10/2008 | Scifert et al. |
| 2008/0269904 A1 | 10/2008 | Voorhies |
| 2008/0288071 A1 | 11/2008 | Biyani et al. |
| 2008/0300598 A1 | 12/2008 | Barreiro et al. |
| 2009/0043312 A1 | 2/2009 | Koulisis |
| 2009/0076440 A1 | 3/2009 | Moutafis et al. |
| 2009/0076556 A1 | 3/2009 | McGarity et al. |
| 2009/0088765 A1 | 4/2009 | Butler et al. |
| 2009/0098184 A1 | 4/2009 | Govil et al. |
| 2009/0099660 A1 | 4/2009 | Scifert et al. |
| 2009/0105718 A1 | 4/2009 | Zhang et al. |
| 2009/0124860 A1 | 5/2009 | Miles et al. |
| 2009/0124980 A1 | 5/2009 | Chen |
| 2009/0125066 A1 | 5/2009 | Kraus et al. |
| 2009/0142385 A1 | 6/2009 | Gross et al. |
| 2009/0187194 A1 | 7/2009 | Hamada |
| 2009/0192350 A1 | 7/2009 | Meja |
| 2009/0192403 A1 | 7/2009 | Gharib et al. |
| 2009/0198245 A1 | 8/2009 | Phan |
| 2009/0198249 A1 | 8/2009 | Ziegler |
| 2009/0198337 A1 | 8/2009 | Phan |
| 2009/0198338 A1 | 8/2009 | Phan |
| 2009/0198339 A1 | 8/2009 | Kleiner et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0228107 A1 | 9/2009 | Michelson |
| 2009/0246244 A1 | 10/2009 | McKay et al. |
| 2009/0248163 A1 | 10/2009 | King et al. |
| 2009/0259108 A1 | 10/2009 | Miles et al. |
| 2009/0264892 A1 | 10/2009 | Beyar et al. |
| 2009/0275995 A1 | 11/2009 | Truckai |
| 2009/0299477 A1 | 12/2009 | Clayton et al. |
| 2009/0306671 A1 | 12/2009 | McCormack et al. |
| 2009/0306692 A1 | 12/2009 | Barrington et al. |
| 2010/0004752 A1 | 1/2010 | White et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |

(56) References Cited

U.S. PATENT DOCUMENTS

| | | |
|---|---|---|
| 2010/0021518 A1 | 1/2010 | Scifert et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087828 A1 | 4/2010 | Krueger et al. |
| 2010/0087875 A1 | 4/2010 | McGahan et al. |
| 2010/0100141 A1 | 4/2010 | de Villiers et al. |
| 2010/0105986 A1 | 4/2010 | Miles et al. |
| 2010/0105987 A1 | 4/2010 | Miles et al. |
| 2010/0112029 A1 | 5/2010 | Scifert |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145452 A1 | 6/2010 | Blaylock et al. |
| 2010/0145461 A1 | 6/2010 | Landry et al. |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0185286 A1 | 7/2010 | Allard |
| 2010/0185287 A1 | 7/2010 | Allard |
| 2010/0185288 A1 | 7/2010 | Carls |
| 2010/0191241 A1 | 7/2010 | McCormack et al. |
| 2010/0191334 A1 | 7/2010 | Keller |
| 2010/0191337 A1 | 7/2010 | Zamani et al. |
| 2010/0198140 A1 | 8/2010 | Lawson |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0249934 A1 | 9/2010 | Melkent |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0266689 A1 | 10/2010 | Simonton et al. |
| 2010/0280622 A1 | 11/2010 | McKinley |
| 2010/0286778 A1 | 11/2010 | Eisermann et al. |
| 2010/0286784 A1 | 11/2010 | Curran et al. |
| 2010/0298938 A1 | 11/2010 | Humphreys et al. |
| 2010/0305575 A1 | 12/2010 | Wilkinson et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2010/0331847 A1 | 12/2010 | Wilkinson et al. |
| 2010/0331891 A1 | 12/2010 | Culbert et al. |
| 2011/0014587 A1 | 1/2011 | Spagnoli et al. |
| 2011/0015748 A1 | 1/2011 | Molz, IV et al. |
| 2011/0020768 A1 | 1/2011 | Spagnoli et al. |
| 2011/0021427 A1 | 1/2011 | Amsden et al. |
| 2011/0028393 A1 | 2/2011 | Vickers et al. |
| 2011/0071527 A1 | 3/2011 | Nelson et al. |
| 2011/0071536 A1 | 3/2011 | Kleiner |
| 2011/0093005 A1 | 4/2011 | Strokosz et al. |
| 2011/0106162 A1 | 5/2011 | Ballard et al. |
| 2011/0144755 A1 | 6/2011 | Baynham et al. |
| 2011/0160777 A1 | 6/2011 | Spagnoli et al. |
| 2011/0184412 A1 | 7/2011 | Scifert et al. |
| 2011/0230970 A1 | 9/2011 | Lynn et al. |
| 2012/0022651 A1 | 1/2012 | Akyuz et al. |
| 2012/0035668 A1 | 2/2012 | Manninen et al. |
| 2012/0065613 A1 | 3/2012 | Pepper et al. |
| 2012/0065687 A1 | 3/2012 | Ballard et al. |
| 2012/0078315 A1 | 3/2012 | Sweeney |
| 2012/0136442 A1 | 5/2012 | Kleiner |
| 2012/0259335 A1 | 10/2012 | Scifert et al. |
| 2013/0073041 A1 | 3/2013 | Scifert et al. |
| 2013/0110169 A1 | 5/2013 | Hynes et al. |
| 2013/0184822 A1 | 7/2013 | Kleiner |
| 2013/0338720 A1 | 12/2013 | Kleiner |
| 2014/0100657 A1 | 4/2014 | McCormack et al. |

FOREIGN PATENT DOCUMENTS

| | | |
|---|---|---|
| JP | 2002-052331 | 2/2002 |
| JP | 2009-534140 | 9/2009 |
| JP | 2009-535115 | 10/2009 |
| WO | WO 95/22402 | 8/1995 |
| WO | WO 99/08627 | 2/1999 |
| WO | WO 02/17801 | 3/2002 |
| WO | WO 2005/037149 | 4/2005 |
| WO | WO 2005/071190 | 8/2005 |
| WO | WO 2007/122006 | 11/2007 |
| WO | WO 2007/127666 | 11/2007 |

OTHER PUBLICATIONS

U.S. Appl. No. 29/453,829, filed May 3, 2013, Kleiner.

"BAK® /Proximity™ (BP®) Cage", Zimmer Website, as early as Oct. 23, 2007, available at www.zimmer.com/z/ctl/op/global/action/1/id/7930/template/MP/prcat/M6/prod/y, printed on Jun. 8, 2009, 1 page.

"BAK® Vista® Radiolucent Interbody Fusion System", Zimmer Website, as early as Oct. 25, 2005, available at www.zimmerindia.com/z/ctl/op/global/action/1/id/7809/template/MP/prcat/M6/prod/y, printed on Jun. 8, 2009, pp. 1-2.

"Facet Joint Syndrome," The Cleveland Clinic Foundation, copyright 1995-2008, printed Nov. 19, 2008, available at www.my.clevelandclinic.org/disorders/facet_joint_syndrome/hic_facet_joint_syndrome.aspx, 2 pages.

"Screws, Cages or Both", Spine Universe Website, as early as Aug. 18, 2002, available at www.spineuniverse.com/displayarticle.php/article1363.html, printed on Jun. 8, 2009, pp. 1-13.

"University of Maryland Spine Program: A Patient's Guide to Anterior Lumbar Interbody Fusion with Intervertebral Cages", University of Maryland Medical Center website, as early as 2003, available at www.umm.edu/spinecenter/education/anterior_lumbar_interbody_fusion_with_intervertebral_cages.htm, printed on Jun. 8, 2009, pp. 1-4.

"Vertebral column," from Wikipedia, the free encyclopedia, printed May 19, 2009, retrieved from www.en.wikipedia.org/wiki/Vertebral_column, 6 pages.

Ehrenberg, "The 3-D Printing Revolution," Science News, Mar. 9, 2013, pp. 20-25.

Ray, "Facet Joint Disorders and Back Pain," published on Spine-Health, Dec. 10, 2002, available at www.spine-health.com/conditions/arthritis/facet-joint-disorders-and-back-pain, 1 page.

Staehler, "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.

Staehler, "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.

Ullrich, "Anterior Cervical Spinal Fusion Surgery," published on Spine-Health, Oct. 7, 2005, available at www.spine-health.com/treatment/back-surgery/anterior-cervical-spinal-fusion-surgery, 2 pages.

(56) References Cited

OTHER PUBLICATIONS

Ullrich, "Cervical Spinal Instrumentation," published on Spine-Health, Oct. 7, 2005, available at www.spine-health.com/treatment/back-surgery/cervical-spinal-instrumentation, 2 pages.

Wascher, "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.

"Zygapophysial joint," from Wikipedia, the free encyclopedia, printed May 19, 2009, retrieved from www.en.wikipedia.org/wiki/Zygapophysial_joint, 2 pages.

International Search Report for International (PCT) Patent Application No. PCT/US11/52278, mailed Jan. 18, 2012 2 pages.

Written Opinion for International (PCT) Patent Application No. PCT/US11/52278, mailed Jan. 18, 2012 5 pages.

International Preliminary Report on Patentability for International (PCT) Patent Application No. PCT/US11/52278, mailed Apr. 4, 2013 7 pages.

Official Action for Australian Patent Application No. 2011305680, dated Jan. 31, 2014, 2 pages.

Notice of Acceptance for Australian Patent Application No. 2011305680, dated Aug. 27, 2014, 2 pages.

Official Action for Canadian Patent Application No. 2,811,018, dated Feb. 6, 2014, 2 pages.

Official Action for European Patent Application No. 11827323.4, dated Jul. 21, 2014, 3 pages.

International Search Report and Written Opinion for International (PCT) Patent Application No. PCT/US2013/023992 mailed Apr. 26, 2013, 8 pages.

International Preliminary Report on Patentability for International (PCT) Patent Application No. PCT/US2013/023992 mailed Aug. 14, 2014, 6 pages.

Notice of Allowance for Japanese Patent Application No. 2013-25835, mailed Mar. 28, 2014, 2 pages (includes English translation).

Official Action for Canadian Patent Application No. 153952, dated Apr. 15, 2014, 1 page.

International Search Report for International (PCT) Patent Application No. PCT/US2009/033488, mailed. Mar. 25, 2009, 2 pages.

Written Opinion for International (PCT) Patent Application No. PCT/US2009/033488, mailed. Mar. 25, 2009, 9 pages.

Official Action for U.S. Appl. No. 12/886,452, mailed May 9, 2012 19 pages.

Official Action for U.S. Appl. No. 12/886,452, mailed Oct. 16, 2012 15 pages.

Notice of Allowance for U.S. Appl. No. 12/886,452, mailed Jul. 15, 2014 7 pages.

Official Action for U.S. Appl. No. 13/367,295, mailed May 2, 2012 16 pages.

Official Action for U.S. Appl. No. 13/367,295, mailed Oct. 15, 2012 14 pages.

Official Action for U.S. Appl. No. 13/367,295, mailed Jul. 14, 2014 9 pages.

Notice of Allowance for U.S. Appl. No. 13/947,255, mailed Oct. 17, 2013 16 pages.

Notice of Allowance for U.S. Appl. No. 14/088,148, mailed Feb. 3, 2014 11 pages.

Notice of Allowance for U.S. Appl. No. 29/453,829, mailed Oct. 8, 2014, 8 pages.

U.S. Appl. No. 29/506,748, filed Oct. 20, 2014, Grimberg et al.

Extended European Search Report for European Patent Application No. 11827323.4, dated Oct. 17, 2014, 9 pages.

U.S. Appl. No. 14/214,031, filed Mar. 14, 2014, Greenhalgh.

Notice of Allowance for U.S. Appl. No. 13/367,295, mailed Jan. 23, 2015 5 pages.

Official Action for Canadian Patent Application No. 2,811,018, dated Dec. 8, 2014, 3 pages.

Official Action (English translation) for Japanese Patent Application No. 2013-529407, mailed Aug. 4, 2015, 3 pages.

Notice of Allowance (with English translation) for Chinese Patent Application No. 201530104963.1, mailed Sep. 6, 2015, 5 pages.

\* cited by examiner

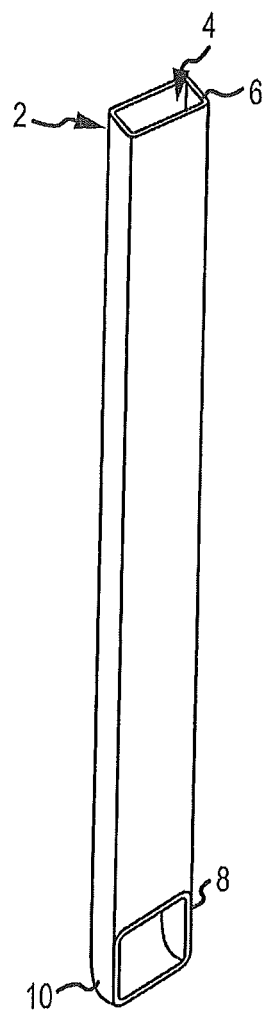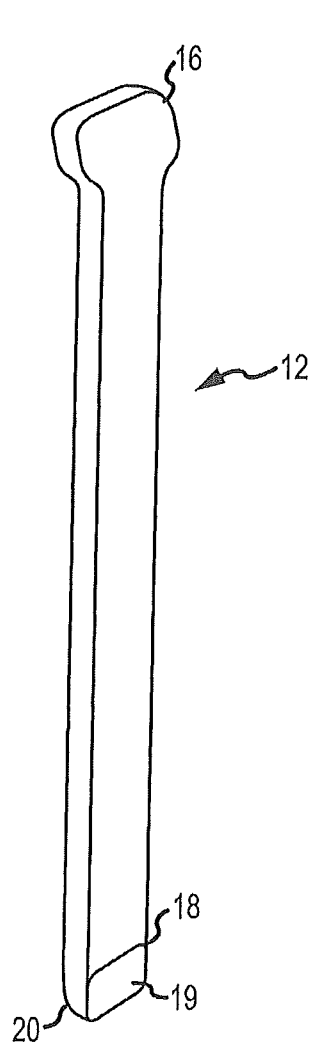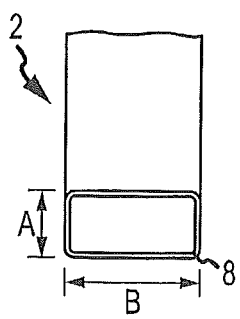
FIG.1C
FIG.1A
FIG.1B

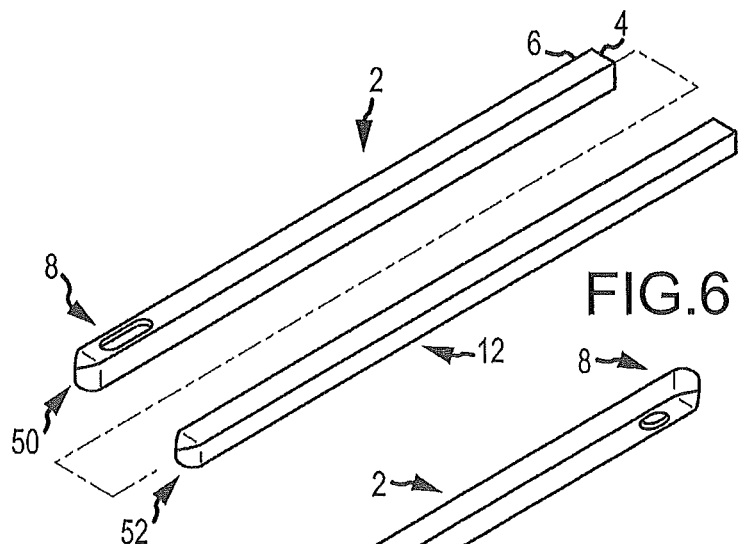
FIG.6
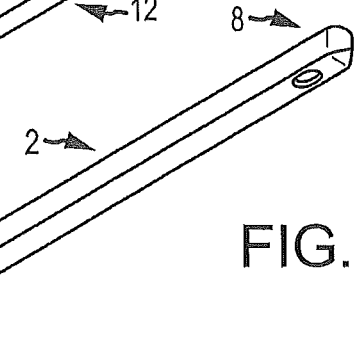
FIG.7
FIG.8
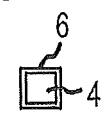
FIG.9
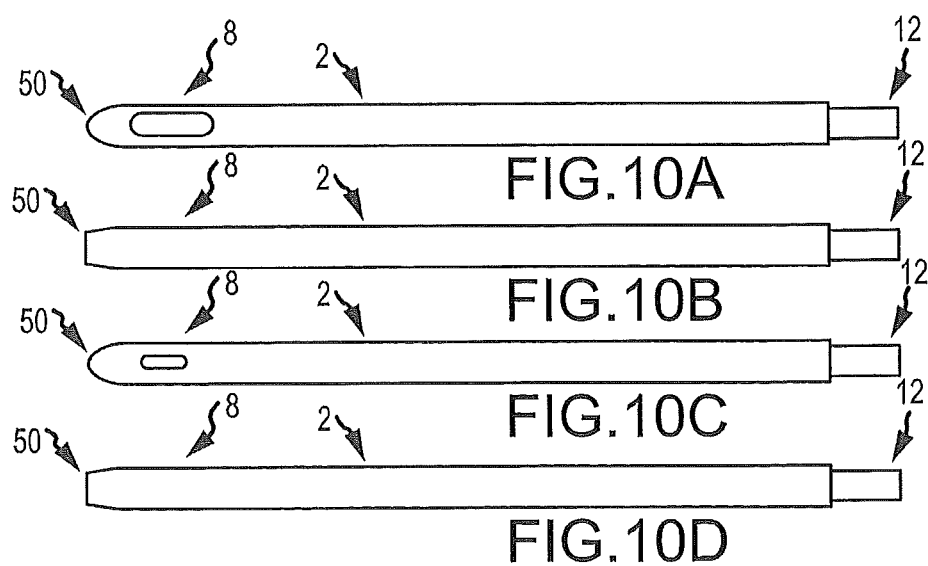
FIG.10A
FIG.10B
FIG.10C
FIG.10D

SECTION A-A

SECTION A-A

SECTION A-A

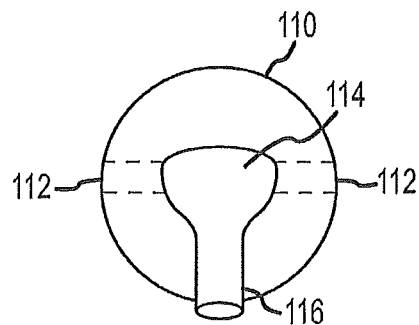
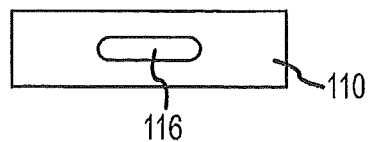
FIG.19A  FIG.19B
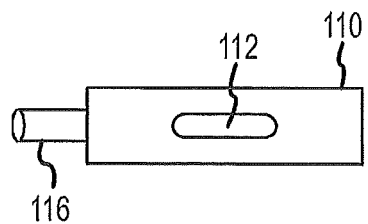
FIG.19C
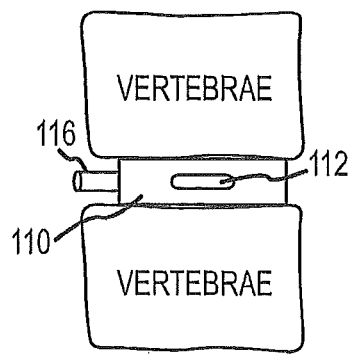
FIG.19D

- 1ml DISK REMOVAL = 6.6+/-0.9ml
- 2ml DISK REMOVAL = 8.4+/-2.8ml
- 3ml DISK REMOVAL = 8.8+/-2.0ml
- 4ml DISK REMOVAL = 10.2+/-3.5ml
- 5ml DISK REMOVAL = 12.1+/-1.9ml
- 6ml DISK REMOVAL = 11.6+/-2.4ml
- 7ml DISK REMOVAL = 11.1+/-3.1ml
- 8ml DISK REMOVAL = 12.3+/-2.3ml

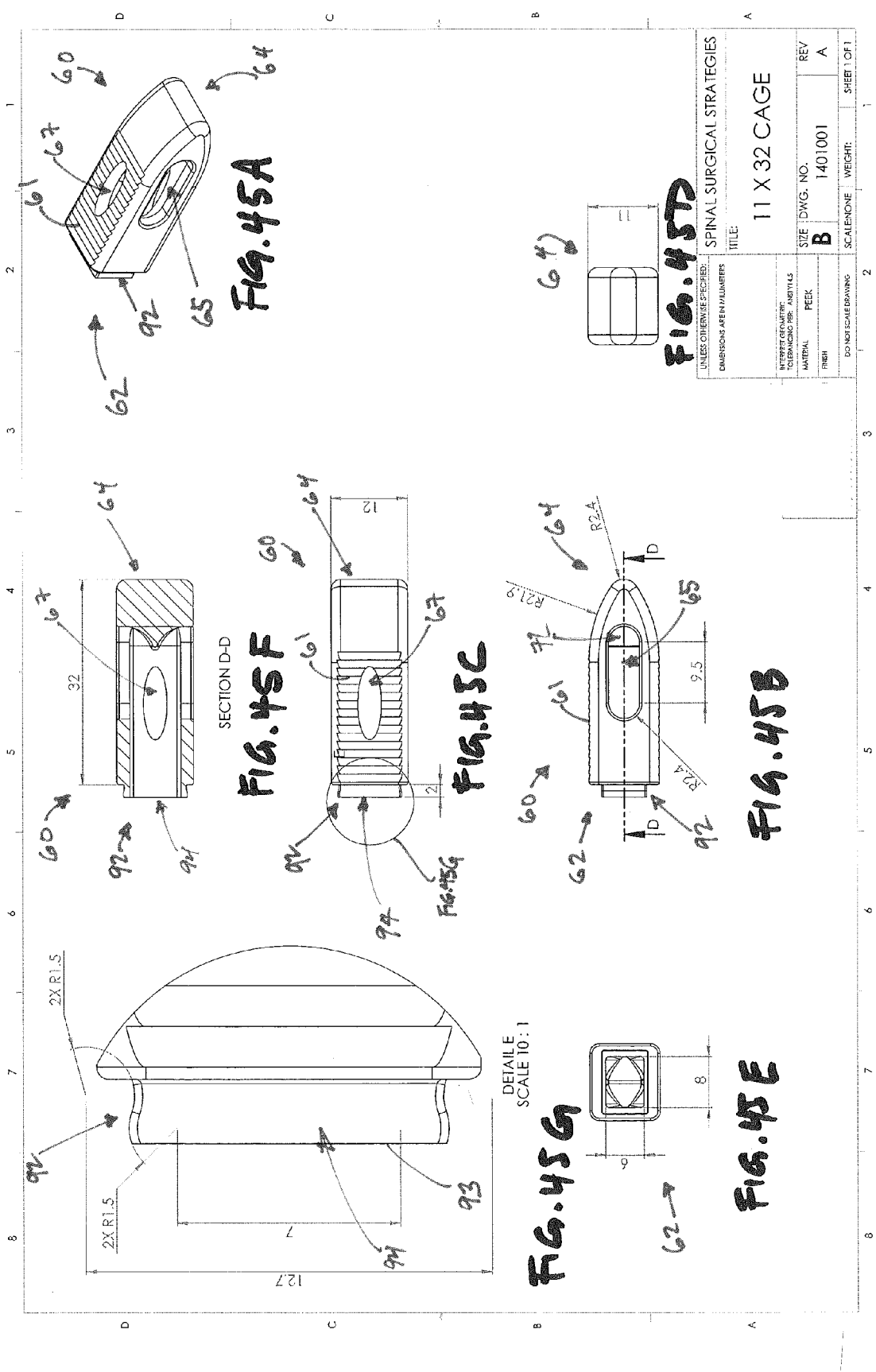

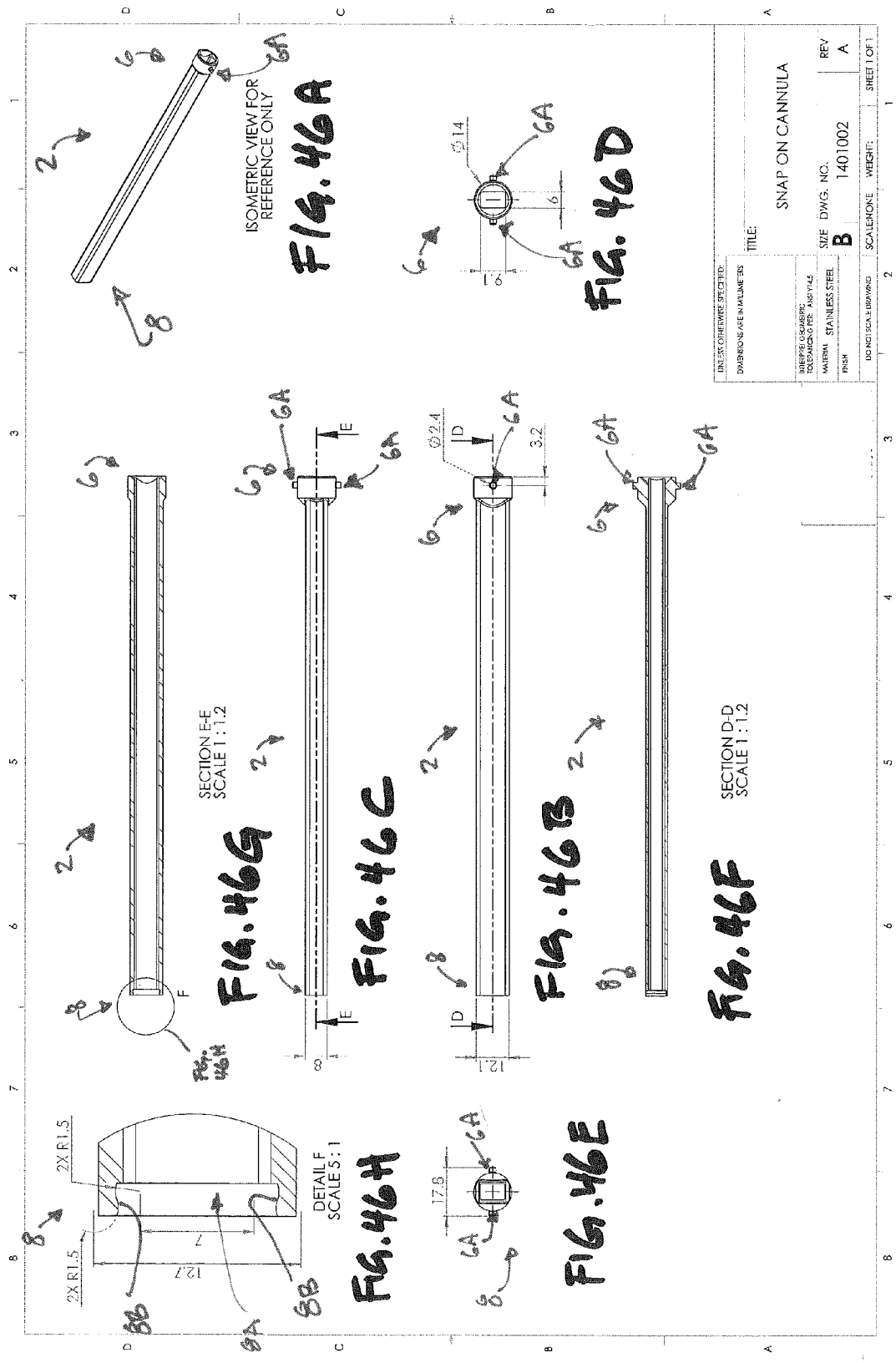

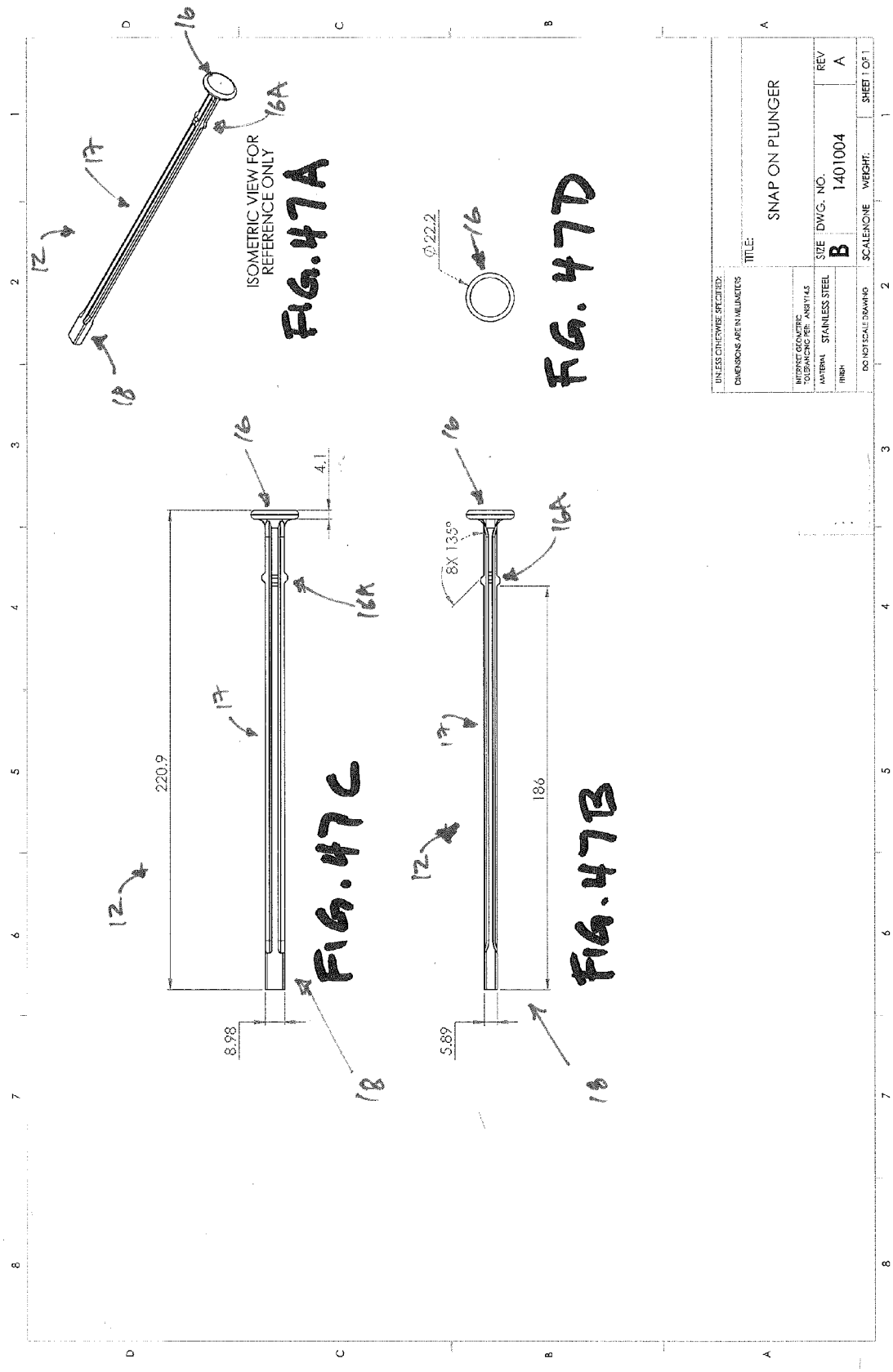

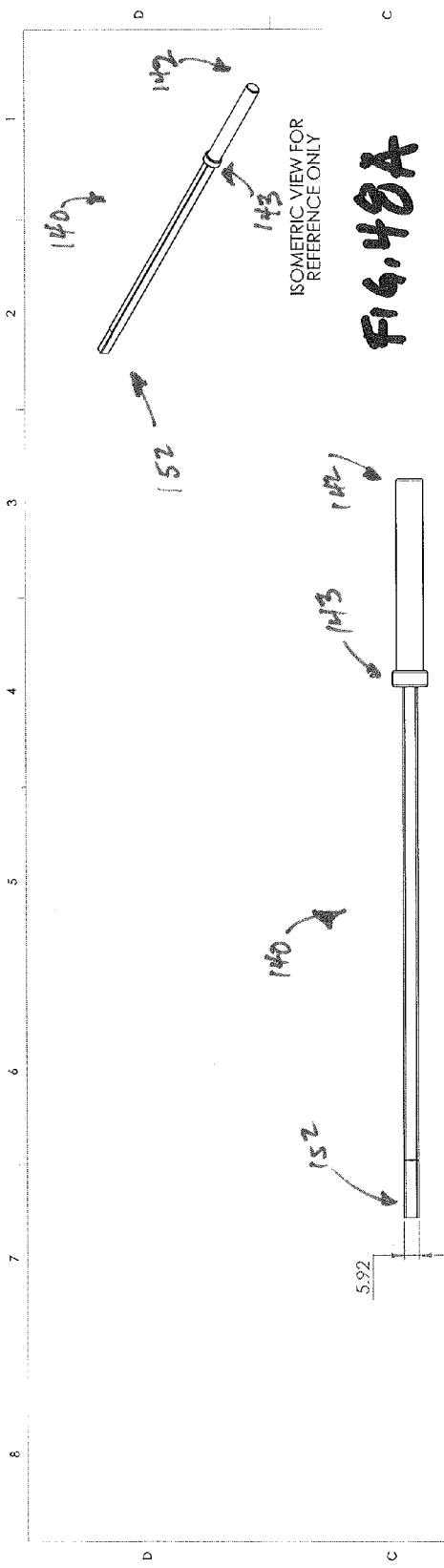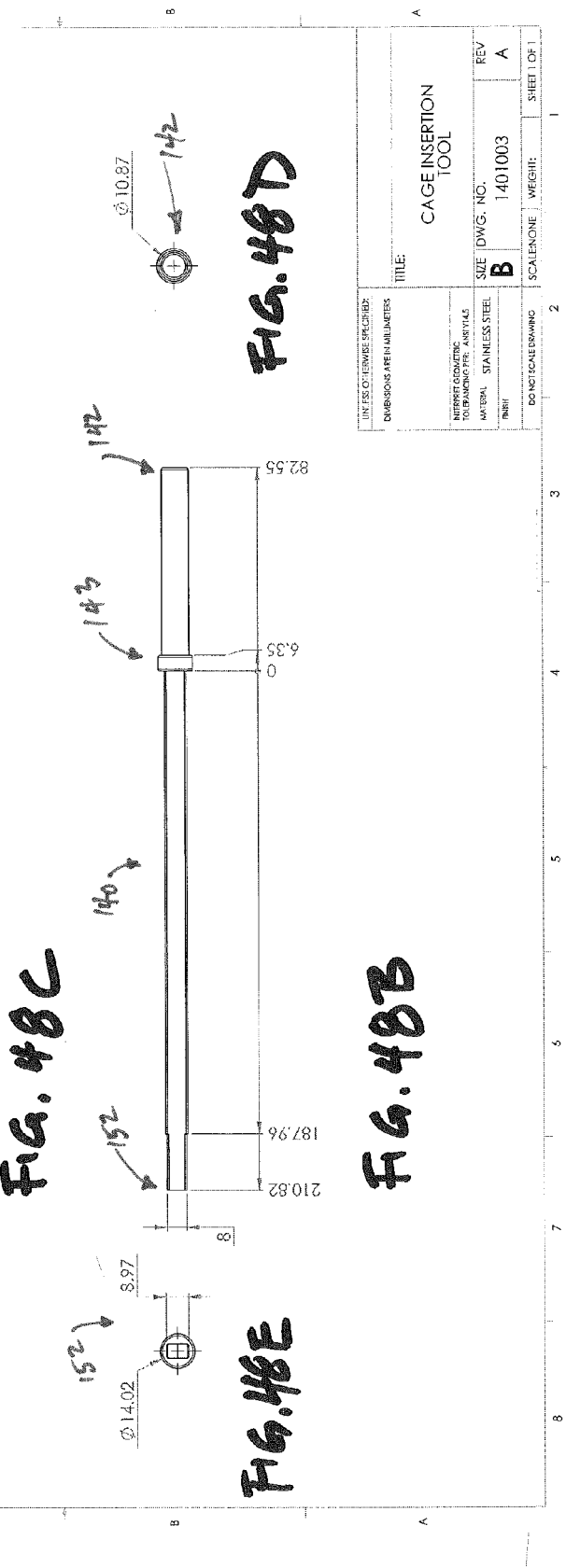

FUSION CAGE WITH COMBINED BIOLOGICAL DELIVERY SYSTEM

CROSS REFERENCE TO RELATED APPLICATIONS

This application is a continuation-in-part of U.S. patent application Ser. No. 14/088,148, filed Nov. 11, 2013, which is a continuation of U.S. patent application Ser. No. 13/947,255, filed Jul. 22, 2013, which is a continuation-in-part of U.S. patent application Ser. No. 13/714,971, filed Dec. 14, 2012, which is a continuation-in-part of U.S. patent application Ser. No. 13/367,295, filed Feb. 6, 2012, which is a continuation-in-part of U.S. patent application Ser. No. 12/886,452, filed Sep. 20, 2010, which claims the benefit of U.S. Provisional Application No. 61/243,664, filed on Sep. 18, 2009, and cross-references U.S. Provisional Application No. 61/439,712, filed Feb. 4, 2011,PCT Application No. IA PCT/US11/52278, filed Sep. 20, 2011, PCT Application No. IA PCT/US13/23992, filed Jan. 31, 2013, and U.S. Design patent application Ser. No. 29/453,829, filed May 3, 2013, the entire disclosures of which are hereby incorporated herein by reference in their entirety.

FIELD OF THE INVENTION

This disclosure relates to orthopedic surgery, and more specifically to an apparatus and method for near-simultaneous and integrated delivery of bone graft material during the placement of surgical cages or other medical implants in a patient's spine.

BACKGROUND OF THE INVENTION

According to the American Academy of Orthopedic Surgeons, about 250,000 spinal fusion surgeries are performed every year, mostly on adults between the ages of 45 to 64. Spinal fusion is a process by which two or more of the vertebrae that make up the spinal column are fused together with bone grafts and internal devices (such as rods) that heal into a single solid bone. Spinal fusion can eliminate unnatural motion between the vertebrae and, in turn, reduce pressure on nerve endings. In addition, spinal fusion can be used to treat, for example, injuries to spinal vertebrae caused by trauma; protrusion and degeneration of the cushioning disc between vertebrae (sometimes called slipped disc or herniated disc); abnormal curvatures (such as scoliosis or kyphosis); and weak or unstable spine caused by infections or tumors.

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). More recently, direct lateral interbody fusion ("D-LIF") has become available. A posterior approach is one that accesses the surgical site from the patient's back, an anterior approach is one that accesses the surgical site from the patient's front or chest, and a direct lateral approach is on that accesses the surgical site from the patient's side. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, the entire disclosure of which is incorporated by reference in its entirety.

Vertebrectomy, or the removal or excision of a vertebra, is another type of spinal surgery that may be necessary to alleviate pain and/or correct spinal defects, such as when disk material above and below a particular vertebra protrudes from the spine and contacts the spinal cord. Once the problematic vertebra is removed, a specialized fusion cage (also called a vertebrectomy cage) may be inserted into its place to restore structural continuity to the spine.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvest. Each of the manufacturers espouses their product as the most advantageous for healing. These products all have similar handling characteristics and the literature reveals that they have similar healing prospects. They come in a syringe and it is up to the surgeon to apply the selected material to the target site. The most common site for application is to the disk space after it has been prepared to a bleeding bed and ready to accept a cage and/or the grafting material. This represents a long and narrow channel even in open procedures. The surgeon is left to his own devices as to how to get the graft from its container to the active site. The devices which have been used have included a "caulking gun" construct and a variety of barrel shaft with a plunger design.

Bone graft typically includes crushed bone (cancellous and cortical), or a combination of these (and/or other natural materials), and may further comprise synthetic biocompatible materials. Bone graft of this type is intended to stimulate growth of healthy bone. As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices in both prepackaged or packaged by the surgeon embodiments. In addition, the method of delivery of bone graft to a particular location varies depending on the form of the bone graft utilized.

Autogenous bone (bone from the patient) or allograft bone (bone from another individual) are the most commonly used materials to induce bone formation. Generally, small pieces of bone are placed into the space between the vertebrae to be fused. Sometimes larger solid pieces of bone are used to provide immediate structural support. Autogenous bone is generally considered superior at promoting fusion. However, this procedure requires extra surgery to remove bone from another area of the patient's body such as the pelvis or fibula. Thus, it has been reported that about 30 percent of patients have significant pain and tenderness at the graft harvest site, which may be prolonged, and in some cases outlast the back pain the procedure intended to correct. Similarly, allograft bone and other bone graft substitutes, although eliminating the need for a second surgery, have drawbacks in that they have yet to be proven as cost effective and efficacious substitutes for autogenous bone fusion.

An alternative to autogenous or allograft bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. However, use of BMPs, although efficacious in promoting bone growth, can be prohibitively expensive.

Another alternative is the use of a genetically engineered version of a naturally occurring bone growth factor. This approach also has limitations. Specifically, surgeons have expressed concerns that genetically engineered BMPs can dramatically speed the growth of cancerous cells or cause non-cancerous cells to become more sinister. Another concern is unwanted bone creation. There is a chance that bone generated by genetically engineered BMPs could form over the delicate nerve endings in the spine or, worse, somewhere else in the body.

Regenerative medicine, which harnesses the ability of regenerative cells, e.g., stem cells (i.e., the unspecialized master cells of the body) to renew themselves indefinitely and develop into mature specialized cells, may be a means of circumventing the limitations of the prior-art techniques. Stem cells, i.e., both embryonic and adult stem cells, have been shown to possess the nascent capacity to become many, if not all, of the 200+ cell and tissue types of the body, including bone. Recently, adipose tissue has been shown to be a source of adult stem cells (See e.g. Zuk, Patricia Z. et al., "Multilineage Cells from Human Adipose Tissue: Implication for Cell-Based Therapies," Tissue Engineering, April 2001, 7:211-28; Zuk, Patricia A. et al., "Human Adipose Tissue Is A Source Of Multipotent Stem Cells," Molecular Biology of the Cell, 2002, 13:4279-4295). Adipose tissue (unlike marrow, skin, muscle, liver and brain) is comparably easy to harvest in relatively large amounts with low morbidity (See e.g. Commons, G. W., Halperin, B., and Chang, C. C. (2001) "Large-volume liposuction: a review of 631 consecutive cases over 12 years" Plast. Reconstr. Surg. 108, 1753-63; Katz, B. E., Bruck, M. C. and Coleman, W. P. 3 (2001b) "The benefits of powered liposuction versus traditional liposuction: a paired comparison analysis" Dermatol. Surg. 27, 863-7). Accordingly, given the limitations of the prior art spinal fusion techniques, there exists a need for a device that incorporates regenerative cells, e.g., stem cells that posses the ability to induce bone formation.

Many different methods and approaches have been attempted to induce bone formation or to promote spinal fusion. The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or the chalking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device, and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device.

As mentioned, the method of delivery of bone graft to a particular location varies depending on the form of the bone graft utilized. For example, in the case of slurry type bone graft, various dispensing devices have been developed having applicators designed to accommodate this type of bone graft. One such device is disclosed by U.S. Pat. No. 5,925,051 issued to Mikhail on Jul. 20, 1999 ("Mikhail"). Mikhail provides a caulking gun type dispenser for introducing bone graft in an enlarged bone (e.g. femoral) cavity. The device preferably includes a barrel pre-loaded with bone graft and a cannulated ejector positioned over a multi-section guide wire. This arrangement purports to accomplish both ejecting bone graft from the barrel and compacting the bone graft material while being guided on the guide wire. Mikhail, however, is designed solely for use with slurry-type bone graft, and does not accommodate bone graft in granule form, which often varies in size among granules and does not have the same "flow" or viscosity characteristics as slurry-type bone graft. Thus, the applicator of Mikhail is insufficient for introducing most bone graft to a surgical site in a patient.

U.S. Pat. No. 6,019,765 issued to Thornhill et al. on Feb. 1, 2000 ("Thornhill") also teaches a bone graft delivery device. The bone graft device applicator of Thornhill is used to apply bone graft to an artificial joint without having to remove a previously implanted prosthesis component. The applicator device includes a hollow tube with an actuation mechanism for discharging the bone graft from the device via a nozzle coupled to a distal end of the tube. The bone graft delivery device of Thornhill may include various components for loading the device with the bone graft, and may further include a plurality of nozzles each having a geometry suited for a particular application. Like Mikhail, the Thornhill delivery device is designed for use with bone slurry, and requires much custom instrumentation and different sized parts to achieve success in many bone graft delivery applications, which in turn increases the time to assemble and use the delivery device and may create further problems during the surgical operation.

U.S. Pat. No. 5,697,932 issued to Smith et al. on Dec. 16, 1997 ("Smith") discloses yet another bone graft delivery system and method. In Smith, a hollow tube of pre-loaded bone graft and a plunger are used to facilitate delivery of the bone graft to a bone graft receiving area. A positioning structure is provided on the plunger to maintain the plunger in a desirable position with respect to the hollow tube. Adjunct positioning means may also be provided to ensure that the plunger remains in the desirable position during the packing of bone graft into the bone graft receiving area. Like the devices of Thornhill and Mikhail, the device disclosed by Smith is clearly designed solely for slurry type bone graft, and does not provide an effective opening for receiving the desired amount of bone graft. Furthermore, the hollow tube shown by Smith is narrow and does not have a footing or other apparatus associated with the delivery device for preventing the device from penetrating, for example, the abdominal region of a patient, which may occur during tamping or packing of the bone graft. This in turn may cause serious injury to a patient if not controlled, and for these reasons the device of Smith is also insufficient for delivery of bone graft to a surgical site.

Traditional devices for inserting a fusion cage or other medical implants into a patient's spine or other surgical area are distinct and separate from traditional devices that deliver bone graft material to the surgical site. For example, once an implant has been positioned, then bone growth material is packed into the internal cavity of the fusion cage. Also, sometimes the process is reversed, i.e., the bone growth is inserted first, and then the implant. These bone growth inducing substances come into immediate contact with the bone from the vertebral bone structures which project into the internal cavity through the apertures. Two devices are thus traditionally used to insert bone graft material into a patient's spine and to position and insert a fusion cage. These devices thus necessitate a disc space preparation followed by introduction of the biologic materials necessary to induce fusion and, in a separate step, application of a structural interbody fusion cage.

The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid 1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal fusion cages may be placed in front of the spine, a procedure known as anterior lumbar interbody fusion, or ALIF, or placed in back of the spine. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back, or through a direct lateral interbody fusion, or D-LIF, technique, involving placement of the cage through an incision in the side.

A typical procedure for inserting a common threaded and impacted fusion cage is as follows. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space. Lastly, bone graft material may be inserted into the surgical area using separate tools and devices.

U.S. Pat. No. 4,743,256 issued to Brantigan ("Brantigan") discloses a traditional spinal back surgical method involving the implantation of a spinal fusion cage. The cage surfaces are shaped to fit within prepared endplates of the vertebrae to integrate the implant with the vertebrae and to provide a permanent load-bearing strut for maintaining the disc space. Brantigan teaches that these cages typically consist of a homogeneous nonresorbable material such as carbon-reinforced polymers such as polyether ether ketone (PEEK) or polyether ketone ether ketone ketone ("PEKEKK"). Although these cages have demonstrated an ability to facilitate fusion, a sufficient fusion is sometimes not achieved between the bone chips housed within the cage and the vertebral endplates. In particular, achieving a complete fusion in the middle portion of the cage has been particularly problematic. As shown in FIG. 6 herein, the upper U and lower L surfaces of these cages C have large transverse pores P which facilitate bone ingrowth, and these pores lead to an inner void space IVS which houses bone graft (not shown) which facilitates the desired fusion. In any case, Brantigan teaches the separate process and procedure for the insertion of a fusion cage and the insertion of bone graft. Indeed, local bone graft harvested from the channel cuts into the vertebrae to receive the plug supplements the fusion.

U.S. Pat. Appl. 20070043442 of Abernathie et al. ("Abernathie") discloses another traditional spinal back surgical method involving the implantation of a spinal fusion cage. Abernathie relates generally to an implantable device for promoting the fusion of adjacent bony structures, and a method of using the same. More specifically, Abernathie relates to an expandable fusion cage that may be inserted into an intervertebral space, and a method of using the same. Abernathie includes an aperture in the fusion cage to allow bone growth therethrough, as a separate procedure to the insertion of the fusion cage.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

U.S. Pat. No. 5,906,616 issued to Pavlov et al. ("Pavlov") discloses a fusion cage of various cylindrical and conical shapes and a method of insertion. Like Brantigan, Pavlov teaches the separate process and procedure for the insertion of a fusion cage and the insertion of bone graft. U.S. Pat. No. 5,702,449 ("McKay") discloses a spinal implant comprising a cage made of a porous biocompatible material reinforced by an outer sleeve made of a second material which is relatively stronger under the compressive load of the spine than the biocompatible material. U.S. Pat. No. 6,569,201 issued to Moumene et al. ("Moumene") teaches a bone fusion device having a structural bioresorbable layer disposed upon the outer surface of a non-resorbable support. As the bioresorbable structural layer resorbs over time, the load upon the bone graft housed within the non-resorbable support increases. Published PCT Application No. WO 99/08627 ("Gresser") discloses a fully bioresorbable interbody fusion device, as well as homogeneous composite devices containing at least 25% resorbable materials. U.S. Pat. No. 7,867,277 issued to Tohmeh discloses a spinal fusion implant of bullet shaped end.

U.S. Pat. No. 7,846,210 issued to Perez-Cruet et al. ("Perez-Cruet") discloses an interbody device assembly consisting of a fusion device and an insertion device. The insertion device positions the fusion device between two vertebrae, provides bone graft material, and then detaches from the fusion device, leaving the fusion device in place to restore disc space height. However, the Perez-Cruet device is designed to receive bone graft material from its insertion device and distribute the material away from the fusion device. In most embodiments of the fusion device, a center plate is positioned immediately downstream of the received bone graft material and directs the bone graft to opposing sides of the fusion device. (See, for example, FIG. 20 depicting plate 308 directing bone graft material 392 along the exterior sides of the fusion device 302). As such, the Perez-Cruet fusion device is unlikely to completely fill the areas near of its fusion cage and deliver bone graft material to the surrounding bone graft site. Furthermore, none of the Perez-Cruet fusion device embodiments feature a defined interior space or a cage-style design. Indeed, the Perez-Cruet fusion device explicitly teaches away from a contained-interior, fusion-cage-style device, asserting that its fusion device fills all of the disc space as opposed to a cage design, which contains the bone material. Furthermore, the Perez-Cruet does not feature a distal tip that functions to precisely position the fusion device and stabilize the device during delivery of bone graft material.

U.S. Pat. No. 7,985,256 issued to Grotz et al. ("Grotz") discloses an expandable spinal implant for insertion between opposed vertebral end plates. The implant is a cylinder block of slave cylinders; a central cavity between the cylinders receives bone graft material and pistons positioned within the cylinders provide a corrective bone engaging surface for expanding against a first vertebral end plate. The insertion tool used to place the spinal implant includes a handle and hollow interior for housing hydraulic control lines and a bone graft supply line. The Grotz system does not allow precise positioning or delivery of bone graft material without an implant and requires a complex and bulky insertion tool.

U.S. Pat. Appl. 2010/0198140 to Lawson ("Lawson") discloses a tool comprising a cannula with an open slot at the distal end and a closed tip. Lawson's tool employs tamps to push bone aside and open up a void for filling; solid bone pellets are then rammed down the hollow interior of the cannula by a tamper and delivered to the surgical site. Lawson does not allow precise positioning or delivery of viscous bone graft material and has no capability to interconnect or integrate with an implant such as a bone graft fusion cage.

U.S. Pat. Appl. 2010/0262245 to Alfaro et al. ("Alfaro") discloses a delivery system for an intervertebral spacer and a bone grafting material comprising a spacer disengagingly attached to a hollow handle. The handle comprises a chamber and bone grafting material-advancing means for introducing bone grafting material from the chamber into the spacer and the intervertebral spaces. The Alfaro system does not allow precise positioning or delivery of bone graft material through a distal tip that precisely positions the fusion device and stabilizes the device during delivery of bone graft material, and does not allow primarily lateral injection of bone graft fusion material.

The prior art bone graft delivery devices listed above typically must come pre-loaded with bone graft, or alternatively require constant loading (where permissible) in order to constantly have the desired supply of bone graft available. Moreover, these bone graft delivery devices generally cannot handle particulate bone graft of varying or irregular particulate size. Furthermore, the prior art devices for inserting a fusion cage or other medical implant into a patient's spine or other surgical area are commonly distinct and separate from traditional devices that deliver bone graft material to the surgical site. As such, two devices are traditionally used to insert bone graft material into a patient's spine and to position and insert a fusion cage. The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures. These problems can be a great inconvenience, cause avoidable trauma to a patient and make these prior art devices unsuitable in many procedures.

Therefore, there is a long-felt need for an apparatus and method for near-simultaneous and integrated precision delivery of bone graft material during the placement of surgical cages or other medical implants in a patient's spine. The present invention solves these needs. The present invention allows biologic material to flow directly to the fusion cage and be dispersed within the disc space in a single step, and can precisely and simply deliver particulate bone graft of varying or irregular particulate size. Thus, the present invention allows application of bone graft material through a detachable fusion cage, eliminates otherwise restriction of the volume of biologic material that may be dispersed within the disk space, and eliminates the requirement that the fusion cage be pushed back into the same place that the fusion material delivery device was, which can lead to additional trauma to the delicate nerve structures.

SUMMARY OF THE INVENTION

Certain embodiments of the present disclosure relate to an apparatus and method for near-simultaneous and integrated delivery of bone graft material during the placement of surgical cages or other medical implants in a patient's spine. The integrated fusion cage and delivery device (the "device") is comprised generally of a tubular member and a plunger for expelling bone graft from the tubular member, through a surgical fusion cage, and into a bone graft receiving area, then disengaging the fusion cage at the surgical site in a human patient. Thus, the apparatus and method allows the biologic material to flow directly into and through the fusion cage and dispersed within the disc space in a single step, and leave the detachable fusion cage in the surgical area. Other embodiments and alternatives to this device are described in greater detail below.

By way of providing additional background, context, and to further satisfy the written description requirements of 35 U.S.C. §112, the following references are incorporated by reference in their entireties for the express purpose of explaining the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

By way of providing additional background, context, and to further satisfy the written description requirements of 35 U.S.C. §112, the following references are incorporated by reference in their entireties for the express purpose of explaining the nature of the surgical procedures in which fusion cages are used and to further describe the various tools and other apparatus commonly associated therewith: U.S. Pat. No. 6,569,201 to Moumene et al.; U.S. Pat. No. 6,159,211 to Boriani et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. 2012/0022651 to Akyuz et al.; U.S. Pat. Appl. 2011/0015748 to Molz et al.; U.S. Pat. Appl. 2010/0249934 to Melkent; U.S. Pat. Appl. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. 2010/0198140 to Lawson; and U.S. Pat. Appl. 2010/0262245 to Alfaro et al.

By way of providing additional background and context, the following references are also incorporated by reference in their entireties for the purpose of explaining the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov, and U.S. Pat. No. 8,088,163 to Kleiner.

In addition, by way of providing additional background and context, the following references are also incorporated by reference in their entireties for the purpose of explaining the nature of spinal fusion and devices and methods commonly associated therewith: U.S. Pat. No. D647,202 entitled "Bone Marrow Harvesting Device" to Scifert issued Oct. 18, 2011; US Pat. No. 7,897,164 entitled "Compositions and Methods for Nucleus Pulposus Regeneration" to Scifert issued March 1, 2011; US Pat. Appl. No. 2010/0112029 entitled "Compositions and Methods for Nucleus Pulposus Regeneration" to Scifert issued May 6, 2010; US Pat. Appl. No. 2010/0021518 entitled "Foam Carrier for Bone Grafting" to Seifert issued Jan. 28, 2010; U.S. Pat. No. 7,824,703 entitled "Medical Implants with Reservoir(s), and Materials Preparable From Same" to Scifert, et al., issued November 2, 2010; US Pat. Appl. No. 2006/0247791 entitled "Multi-Purpose Medical Implant Devices" to McKay, et al., issued November 2, 2006; US Pat. Appl. No. 2007/0225811 entitled "Conformable Orthopedic Implant" to Scifert, et al., issued Sep. 27, 2007; U.S. Pat. No. 6,746,487 entitled "Intramedullary Trial Fixation Device" to Scifert, et al., issued Jun. 9, 2004; US Pat. Appl. No. 2013/0073041 entitled "Medical Implants With Reservoir(s), and Materials Preparable From Same" to Scifert et al., issued Mar. 21, 2013; US Pat. Appl. No. 2010/0266689 entitled "Tissue Augmentation With Active Agent For Wound Healing" to Simonton et al., issued Oct. 21, 2010; US Pat. Application No. 2011/0028393 entitled "Flowable Paste And Putty Bone Void Filler" to Vickers et al., issued Feb. 3, 2011; US Pat. Appl. No. 2009/0099660 entitled "Instrumentation To Facilitate Access Into The Intervertebral Disc Space And Introduction Of Materials Therein" to Scifert issued Apr. 16, 2009; US Pat. Appl. No. 2011/0014587 entitled "System And Methods Of Preserving An Oral Socket" to Spagnoli et al., issued Jan. 20, 2011; U.S. Pat. No. 8,148,326 entitled "Flowable Carrier Matrix and Methods for Delivering to a Patient" to Beals et al., issued Apr. 3, 2012; US Pat. Appl. No. 2008/0260598 entitled "Devices, Methods and Systems for Hydrating a Medical Implant Material" to Gross et al., issued Oct. 23, 2008; US Pat. Appl. No. 2007/0265632 entitled "Bone Cutting Template and Method of Treating Bone Fractures" to Seifert et al., issued Nov. 15, 2007; U.S. Pat. No. 8,293,232 entitled "Flowable Carrier Matrix and Methods for Delivering to a Patient" to Beals et al., issued Oct. 23, 2012; U.S. Pat. No. 8,198,238 entitled "Flowable Carrier Matrix and Methods for Delivering to a Patient" to Beals et al., issued Jun. 12, 2012; U.S. Pat. No. 7,939,092 entitled "Cohesive Osteogenic Putty and Materials Therefor" to McKay et al., issued May 10, 2011; US Pat. Appl. No. 2007/0264300 entitled "Therapeutic Agent Carrier and Method of Treating Bone Fractures" to Seifert et al., issued Nov. 15, 2007; US Pat. Appl. No. 2011/0020768 entitled "Implantable Screw and System for Socket Preservation" to Spagnoli et al., issued Jan. 27, 2011; US Pat. Appl. No. 2012/0065687 entitled "Multi-Radius Vertebral Rod with a Varying Stiffness" to Ballard et al., issued Mar. 15, 2012; US Pat. No. 2007/0225219 entitled "Intramedullary Drug Delivery Device and Method of Treating Bone Fractures" to Boden et al., issued Sep. 27, 2007; U.S. Pat. No. 7,723,291 entitled "Release of BMP, Bioactive Agents and/or Cells Via a Pump into a Carrier Matrix" to Beals et al., issued May 25, 2010; U.S. Pat. No. 7,671,014 entitled "Flowable Carrier Matrix And Methods For Delivering To A Patient" to Beals et al., issued Mar. 2, 1010; U.S. Pat. No. 7,897,564 entitled "Flowable Carrier Matrix and Methods for Delivering to a Patient" to Beals et al., issued Mar. 1, 2011; US Pat. Application No. 2011/0160777 entitled "System and Methods of Maintaining Space for Augmentation of the Alveolar Ridge" to Spagnoli et al., issued Jun. 30, 2011; US Pat. Application No. 2009/0246244 entitled "Malleable Multi-Component Implants and Materials Therefor" to McKay et al., issued Oct. 1, 2009; US Pat. Application No. 2009/0246244 entitled "Malleable Multi-Component Implants and Materials Therefor" to McKay et al., issued Oct. 1, 2009; US Pat. No. 2013/0110169 entitled "Vertebral Rod System and Methods of Use" to Hynes, et al., issued May 2, 2013; US Pat. Appl. No. 2011/0184412 entitled "Pre-Assembled Construct With One Or More Non-Rotating Connectors For Insertion Into a Patient" to Scifert, et al., issued Jul. 28, 2011; U.S. Pat. No. 7,964,208 entitled "System and Methods of Maintaining Space For Augmentation of the Alveolar Ridge" to Spagnoli, et al., issued Jun. 21, 2011; U.S. Pat. No. 8,080,521 entitled "Flowable Carrier Matrix and Methods for Delivering to a Patient" to Beals, et al., issued Dec. 20, 2011; US Pat. Appl. No. 2009/0142385 entitled "Compositions for Treating Bone Defects" to Gross, et al., issued Jun. 4, 2009; U.S. Pat. No. 7,578,820 entitled "Devices and Techniques for a Minimally Invasive Disc Space Preparation and Implant Insertion" to Moore, et al., issued Aug. 25, 2009; US Pat. Appl. No. 2010/0305575 entitled "Methods and Apparatus for Performing Knee Arthroplasty" to Wilkinson, et al., issued Dec. 2, 2010; US Pat. Appl. No. 2011/0021427 entitled "Biphasic Calcium Phosphate Cement for Drug Delivery" to Amsden, et al., issued Jan. 27, 2011; US Pat. Appl. No. 2012/0259335 entitled "Patello-Femoral Joint Implant and Instrumentation" to Scifert, et al., issued Oct. 11, 2012; US Pat. Appl. No. 2011/0106162 entitled "Composite Connecting Elements for Spinal Stabilization Systems" to Ballard, et al., issued May 5, 2011; US Pat. Appl. No. 2004/0073314 entitled "Vertebral Body and Disc Space Replacement Devices" to White, et al., issued Apr. 15, 2004; U.S. Pat. No. 7,513,901 entitled "Graft Syringe Assembly" to Scifert, et al., issued Apr. 7, 2009; US Pat. Appl. No. 2010/0004752 entitled "Vertebral Body and Disc Space Replacement Devices" to White, et al., issued Jan. 7, 2010; U.S. Pat. No. 7,615,078 entitled "Vertebral Body and Disc Space Replacement Devices" to White, et al., issued Nov. 10, 2009; U.S. Pat. No. 6,991,653 entitled "Vertebral Body and Disc Space Replacement Devices" to White, et al., issued Jan. 31, 2006; US Pat. Appl. No. 2010/0331847 entitled "Methods and Apparatus for Performing Knee Arthroplasty" to Wilkinson, et al., issued Dec. 30, 2010; US Pat. Appl. No. 2006/0116770 entitled "Vertebral Body and Disc Space Replacement Devices" to White, et al., issued Jun. 1, 2006; and U.S. Pat. No. 8,246,572 entitled "Bone Graft Applicator" to Cantor, et al., issued Aug. 21, 2012.

According to varying embodiments described herein, the present invention is directed to near-simultaneous and integrated delivery of bone graft material during the placement of surgical cages or other medical implants into a patient's spine. The delivery of the bone graft material may be to any area of the body, and in particular to the intervertebral joints of the spine, for achieving bone graft fusion. The device may be used without the optional near-simultaneous and integrated placement of surgical cages with the delivery of bone graft material. Also, the invention may be used in the repair of a bone joint or in connection with the implantation of prosthetic devices in the body, including, by way of example but not limitation, the hip, knee and a variety of spinal joints. Additionally, the present invention may be used in primary surgery, in which a bone graft is being supplied to promote new bone growth or to reconstruct a joint for the first time, as well as in revision surgery, in which a follow-up procedure is being performed in an area that has previously been subject to one or more surgeries. Further, the invention may be used in any application where material is to be delivered with precision to a confined area where access is restricted, to include surgical procedures, repair of installed or uninstalled mechanical or electrical devices, and arming or disarming of explosive devices.

Although well suited for use in human patients, and although much of the discussion of the present invention is directed toward use in humans, advantages offered by the present invention may be realized in the veterinary and scientific fields for the benefit and study of all types of animals and biological systems. Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas, specifically where there is a desire to constrain added fluid material to particular regions. For example, the present invention finds application in methods where the objective is to confine added material to predetermined areas of interest and to prohibit the undesired translocation of such material until an operation is complete and/or until a predetermined later time.

According to various embodiments of the present disclosure, one aspect of the invention is to provide an integrated fusion cage and graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space. A substantially round shape may also be employed that provides the surgeon with an indication of directional orientation.

The phrase "removably attached" and/or "detachable" is used herein to indicate an attachment of any sort that is readily releasable.

The phrase "integrated fusion cage", "spinal fusion implant", "biological implant" and/or "fusion cage" is used here to indicate a biological implant.

According to various embodiments of the present disclosure, it is another aspect that the hollow tubular member further comprise at least one opening on a lateral face or surface of the hollow tubular member, at one distal end, for ejecting bone graft material into a bone graft receiving area, such as a disc space, such that the bone graft material is ejected from the hollow tubular member through an additional implant, such as a structural cage implant. In addition, the graft material is dispersed into the area of the debrided disc space surrounding and within the cage. Furthermore, the structural cage implant is removably attached to the hollow tubular member so as to be deposited into the surgical area. Thus, the device may be used in an integrated and near-simultaneous method for depositing bone graft material into a debrided disc space through a structural cage implant and leaving the structural implant.

According to various embodiments of the present disclosure, one aspect of the invention is to provide an integrated fusion cage detachable component of the integrated fusion cage and graft delivery device that comprises a biological implant that fits over the distal end of the substantial hollow tube, and which has a shape that is substantially congruent with the distal end of the hollow tube. However, the shape and configuration of the integrated fusion cage need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space. A substantially round shape may also be employed that provides the surgeon with an indication of directional orientation.

In a preferred embodiment, the fusion cage has a tapered tip, and several open channels along the medial surfaces. In a preferred embodiment, the fusion cage and/or the bone graft delivery portion of the integrated fusion cage and graft delivery device is of oblong or rectangular, or square shape. The integrated fusion cage and graft delivery device is designed to avoid blocking or impacting bone graft material into a surgical disc space, thereby limiting the bone graft material that may be delivered, and not allowing available fusion space to be fully exploited for fusion.

In a preferred embodiment, the fusion cage has a keel-shaped tip to separate disk and prevent annular penetration. Also, the fusion cage has dual portals for bone graft discharge, with the medial openings larger than the lateral openings. Further, the fusion cage may be designed in variable heights and lengths so that it fits snugly into the prepared disk space.

In a preferred embodiment that is ideal for anterior lumbar interbody fusion, the fusion cage has two portals for bone graft discharge positioned on opposite sides of the fusion cage. In a preferred embodiment that is ideal for direct lateral interbody fusion, the fusion cage has six portals for bone graft discharge, with three portals on one side of the fusion cage and three portals on an opposite side of the fusion cage. And, in a preferred embodiment that is ideal for post-vertebrectomy use, two opposing wall portions of the fusion cage are substantially porous to bone graft slurry, while the substantial remainder of the wall of the fusion cage is substantially impervious to bone graft slurry.

In another embodiment of the device, the hollow tube engages with the fusion cage via a break-off collar and the plunger inserts into the interior of the hollow tube. The break-off collar may be severed by any of several means, to include application of torsion and/or rotational force and/or lateral force to the break-off collar, for example by twisting on the hollow tube and/or the plunger. The break-off collar may be formed by any of several means, comprising a thinner and/or reduced cross-sectional, that is thickness, a pre-set fracture-line, one or more notches, a frangible portion defined by a discrete, extended area that is weaker in one or more respects as compared to surrounding and/or adjacent material, and any means known to those skilled in the art to achieve reliable break-off. Preferably a clean break is achieved such that no surgically significant issues arise so such severance of the cage-portion and the hollow for the portion. In other embodiments, other ways devices and features can be employed to achieve separation of or first delivery tube structure and a second structure intended to remain in a patient. For example, electric and/or magnetic disconnecting mechanisms can be used in lieu of a physical breaking/severing of two discrete portions that define the above-referenced first and second structures. A smooth edge preferably remains after such severance of the cage. Moreover, it will be understood as being within the scope of the present invention to use more conventional coupling/decoupling mechanisms to achieve desired separation of the first and second structures, e.g. bayonette mounted features, tongue and groove, male/female interlocking structures, clamping devices, nested arrangements, etc., all of which find support in the various cited references incorporated herein by reference. In one example method of use, the connected hollow tube and fusion cage is inserted into the surgical area, bone graft material is inserted into the hollow tube (or already provided as a pre-packaged material), the plunger is pushed into the hollow tube, so as to deliver bone graft material to the site, then the plunger is reversed or pulled-out so to retreat from the site and move higher or beyond the break-off collar, and then the break-off collar is broken so as to disengage the fusion cage from the hollow tube and therein leave the fusion cage at the surgical site. In another embodiment of the device, the hollow tube engages with a connector conduit which in turn connects with the fusion cage via a break-off collar. One or more connectors connect the hollow tube with the connector conduit. The hollow tube fits over the connector conduit. The one or more connectors fit through the hollow tube and the connector conduit. Alternately, the hollow tube may fit over the connector conduit via a press-fit, aka interference fit, without need of one or more connectors. In one embodiment, the connectors comprise set screws, pins and tabs. The connector conduit allows, for example, various fusion cages designs to be fitted to a common hollow tube / plunger combination. This allows, for example, the common hollow tube / plunger combination to be re-sterilized and thus reused in multiple surgical procedures. In one embodiment, the hollow tube / plunger combination is re-usable and the fusion cage is disposable.

In one embodiment of the connector conduit, the connector conduit is of circular cross-section. In another embodiment, the connector conduit is of conical shape, or any shape that allows a transition in diameter between the fusion cage and the follow tube.

In one example method of use, the hollow tube is inserted over the connection conduit (which is attached to the fusion cage), then inserted into the surgical area, bone graft material is inserted into the hollow tube (or already provided as a pre-packaged material), the plunger is pushed into the hollow tube (and past the connection conduit), so as to deliver bone graft material to the site, then the plunger is reversed or pulled-out so to retreat from the site and move higher or beyond the break-off collar, and then the break-off collar is broken so as to disengage the fusion cage from the hollow tube (which is still connected to the connection conduit) and therein leave the fusion cage at the surgical site.

The break-off collar may be severed by any of several means, to include application of torsion and/or rotational force and/or lateral force to break-off collar, for example by twisting on the hollow tube and/or the plunger.

In one embodiment of the fusion cage, the fusion cage is of rectangular cross-section, such that one pair of opposite sides, for example a height first pair of sides, has a dimension of approximately 8-14 mm, and a second pair of opposite sides, for example a length dimension, of approximately 22-36 mm. One skilled in the art will appreciate that the exact dimensions of the fusion cage may be adapted to conform to particulars of the surgical site, for example, the relative sizing between the particular vertebrae in which bone graft material and/or a fusion cage is to be inserted. In other embodiments of the fusion cage, the fusion cage is of a substantially cylindrical shape. For example, a preferred embodiment of a fusion cage for use in an ALIF procedure forms a substantially cylindrical shape, with a height of approximately 8-14 mm and a diameter of less than about 36 millimeters. As another example, a preferred embodiment of a fusion cage for use in conjunction with a vertebrectomy has a substantially cylindrical shape with a height equal to or greater than the height of the vertebra (or the collective height of the vertebrae) it is intended to replace and a diameter of less than about 36 millimeters. Preferably, the separation "zone" between the cage and the hollow filling tube is at one end of the cage, preferably the end of the cage (when implanted) closer to the incision site.

A preferred method of using the integrated fusion cage and graft delivery device comprises precisely inserting the integrated fusion cage and graft delivery device, in one or more of the embodiments contained herein, into the surgical area. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area through and into the surgical implant cage. The surgical implant device may then be selectably detached from the integrated fusion cage and graft delivery device so as to remain at the surgical site.

Another method of using the integrated fusion cage and graft delivery device comprises inserting the integrated fusion cage and graft delivery device into a prepared disk space, such that the fusion cage portion fits snugly into the prepared disk space (the fusion cage is designed in variable heights and lengths so as to fit snugly into the prepared disk space), pushing the plunger through the hollow shaft so as to push biological fusion material (e.g. bone graft) through the hollow shaft to flow the biological material through the fusion cage's open lateral and/or medial portals in communication with the hollow tube and plunger, thereby delivering biological material into the prepared disk space, after which the fusion cage is detached from the hollow tube and left in the disk space. Thus, the fusion cage is left in the disk space with a maximum and/or optimal amount of biological material near-simultaneously delivered within the fusion cage and/or surrounding the fusion cage in the disk space.

Using the integrated fusion cage and graft delivery device as described overcomes a problem associated with the traditional separate application of bone graft material and insertion of a fusion cage. Specifically, in the traditional method, the volume of disk space which does not contain bone graft material is limited, which, for example, limits the effectiveness of the surgical procedure. For example, using the traditional two-step procedure, bone graft may be inserted into, for example, a cylindrically-shaped area of radius r to a height h of 8 mm, and then a cylindrically-shaped fusion cage inserted of height h of 14 mm. Thus, the surgical area is left without a complete volume of bone graft material, i.e. because the volume of a cylinder is Volume=$\pi r^2 h$, the bone graft area is left without $\pi r^2 (14\text{ mm}-8\text{ mm})$, or $6\pi r^2$ of bone graft material. (Note that this represents a 75% increase in bone graft material delivered to the surgical site for these example dimensions). This effectively dilutes the bone graft material and reduces its effectiveness. The present invention can substantially or completely fill the available disk space with bone graft material, because distraction of the disk space is performed substantially simultaneously with application of the fusion cage. Because more biological material is delivered to the prepared disk space, the fusion rate should increase. Also, by directly implanting fusion material, e.g. bone graft material, though a fusion cage positioned for detachment (and then detached) as a single step, time is saved and there is less manipulation of the sensitive nerve tissue at the fusion site (which increases safety).

Furthermore, the integrated fusion cage and graft delivery device may be used without the surgical implant delivery device portion such that the method comprises precisely inserting the integrated fusion cage and graft delivery device, in one or more of the embodiments contained herein, into the surgical area that may already contain one or more additional implants, such as a structural cage implant. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area without depositing bone graft material into the path of any structural cage implant or other implant that may already be present.

According to a still further aspect of the present invention, the integrated fusion cage may be introduced into a spinal target site without the use of the graft delivery device that is through use of any of a variety of suitable surgical instruments having the capability to engage the implant. The integrated fusion cage is capable of being used in minimally invasive surgical procedures, needing only a relatively small operative corridor for insertion.

According to a still further aspect of the present invention, the integrated fusion cage of the present invention may be used in a variety of configurations in a fusion procedure, including but not limited to (and by way of example only) unilateral, paired unilateral and bilateral.

Furthermore, the integrated fusion cage and graft delivery device and method of use is applicable to position and deliver fusion cages from the side, directly anterior or in the anterior fusion cages of the cervical spine.

In a preferred embodiment, the integrated fusion cage and graft delivery device comprises a hollow tube or contains at least one inner lumen constructed to receive bone graft, and a plunger adapted for insertion at least partially within the hollow tube and preferably through the full extent of the hollow tube. The plunger of some embodiments is generally of the same geometric configuration as the hollow interior potion of the hollow tube so that the plunger, once fully inserted in to the hollow tube, is substantially congruent with the hollow interior portion of the hollow tube, e.g. both the plunger and the hollow tube are substantially the same shape and/or class. The plunger preferably extends about the same length as the hollow tube, and further comprises an end portion, e.g. at least one knob or handle for grasping and manipulation by a user, or in robotic or automated or semi-automated control or surgeries, by a machine.

Also according to a preferred embodiment, the hollow interior portion of the hollow tube further comprises a sloped or curved surface at a second end (e.g. positioned near a place for deposit of bone graft material) adjacent and opposite a lateral window or opening in a lateral face of the hollow tube. As the interior of the hollow tube comprises a sloped or curved surface at its second end, the plunger also comprises a sloped or curved surface at a second end of the plunger. The plunger terminates opposite the curved surface at its second end with a laterally faced surface, which corresponds to the lateral window or opening at the second end of the hollow tube. The distal end of the hollow tube is fitted with a substantially conformal fusion cage that covers the exterior surface of the hollow tube, fitted with one or more openings that align with one or more openings of the hollow tube. Thus, in cooperation, the plunger may be inserted into the opening of the hollow tube, and extended the entire length of the hollow tube, at least to a point where the laterally faced surface of plunger is in communication with the lateral window or opening at the second end of the hollow tube. This configuration permits a user to eject substantially all of the bone graft material that is placed into the hollow tube in a lateral direction at the bone graft receiving area, through the substantially conformal and detachable fusion cage that covers the exterior surface of the hollow tube, optionally detach the detachable fusion cage, during a surgical procedure.

In a preferred embodiment, the integrated fusion cage and graft delivery device comprises an integrated fusion cage that comprises a first proximal end and a second distal end, wherein the first proximal end contains an opening adapted to allow fitting and/or engagement to the distal end of the hollow tube. This fitting and/or engagement may be over the external surface of the hollow tube or inside the interior of the hollow tube. Further, the integrated fusion cage may comprise one or more medial openings and one or more lateral openings that align with one or more openings at the distal end of the hollow tube. Further, the integrated fusion cage may contain surfaces, such as belts or striations, along one or more medial surfaces of the integrated fusion cage. The integrated fusion cage is configured such that when a plunger, once fully inserted in to the hollow tube, is substantially congruent with the hollow interior portion of the hollow tube, e.g. both the plunger and the hollow tube are substantially the same shape and/or class and bone graft material is delivered through the integrated fusion cage into the surgical area.

In one embodiment, a substantially hollow implant is detachably interconnected to a distal end of the hollow tube, the implant having a proximal end and a tapered distal end, the tapered distal end having an exterior tapered surface and a tapered interior surface, and the plunger adapted for inserting into the proximal end of the hollow tube, the plunger having a tapered distal end being contoured to the tapered interior surface of the distal end of the implant to form a conforming fit between the tapered distal end of the plunger and the tapered interior surface of the distal end of the implant when the plunger is fully inserted into the implant such that bone graft material within the hollow tube is delivered to a graft receiving area through at least one opening of the implant. Further, the distal end of the implant may comprise a closed distal tip, and the tapered distal end of the plunger may be wedge-shaped and the tapered interior surface of the closed distal tip of the distal end of the implant may be wedge-shaped.

The spinal fusion implant of the present invention may be used to provide temporary or permanent fixation along an orthopedic target site.

The spinal fusion implant of the present invention may be provided with any number of additional features for promoting fusion, such as one or more apertures extending between the top and bottom surfaces which allow a boney bridge to form through the spinal fusion implant.

The spinal fusion implant may also be provided with any number of suitable anti-migration features to prevent the implant from migrating or moving from the disc space after implantation. Suitable anti-migration features may include, but are not necessarily limited to, angled teeth or ridges formed along the top and bottom surfaces of the implant and/or rod elements disposed within the distal and/or proximal ends.

According to a further aspect of the present invention, the spinal fusion implant may be provided with one or more radiographic markers at the proximal and/or distal ends. These markers allow for a more detailed visualization of the implant after insertion (through radiography) and allow for a more accurate and effective placement of the implant.

According to a still further aspect of the present invention, the distal end of the spinal fusion implant may have a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

Another embodiment for the integrated fusion cage and graft delivery device comprises a detachable fusion cage that is detachable, or removably attached, by any of several means. As disclosed above, in one embodiment, the fusion cage is substantially conformal with the distal end of the hollow tube in that it covers the exterior surface of the hollow tube, wherein the fusion cage is configured with one or more openings that align with one or more openings of the hollow tube. In one preferred embodiment, the fusion cage of the integrated fusion cage and graft delivery device forms an interference fit with the fusion cage, such that when the integrated fusion cage and graft delivery device is inserted into the surgical area, the integrated fusion cage and graft delivery device presses against bone and/or vertebrates such that when an axial force is applied to the integrated fusion cage and graft delivery device in a rearward direction (toward the proximal end of the integrated fusion cage and graft delivery device), the fusion cage detaches from the integrated fusion cage and graft delivery device and thereby remains in the surgical area.

In another embodiment for the integrated fusion cage and graft delivery device and its method of use, the fusion cage is substantially filled with bone graft material after the fusion cage is implanted. In another embodiment for the integrated fusion cage and graft delivery device and its method of use, the fusion cage is substantially filled with bone graft material simultaneously with the implantation of the fusion cage.

In another embodiment for the integrated fusion cage and graft delivery device and its method of use, the fusion cage and/or the bone graft material associated with the fusion cage may be accessed during subsequent surgical operations.

In another embodiment for the integrated fusion cage and graft delivery device and its method of use, the fusion cage is a separate device, for example a pre-packaged implant device, which may be installed independently from the integrated fusion cage and graft delivery device or installed in coordination with the integrated fusion cage and graft delivery device. In either situation, the device may be used to provide bone graft material in and/or around the pre-packaged implant.

In another embodiment for the integrated fusion cage and graft delivery device and its method of use, some or all of the bone graft material is provided as a component of a per-packaged implant. In another embodiment for the integrated fusion cage and graft delivery device, the detachable fusion cage is detachable by way of a indent-tab that penetrates the interior of the hollow tube, such, when the plunger is substantially inserted into the hollow tube, the indent-tab is pushed out from the interior of the hollow tube so as to no longer be attached to the integrated fusion cage and graft delivery device, thereby remaining in the surgical area.

In another embodiment, the hollow tube is of cylindrical shape and includes one or more locking tabs or indent tabs configured to engage one or more locking slots of the fusion cage. The locking tabs may permanently or not permanently engage the locking slots, and may be of a shape to include rectangular, circular and oblong. In one embodiment of the locking tabs and locking slots, the locking tabs and locking slots engage one another by rotating the hollow tube clockwise and are released by counterclockwise rotation. In another embodiment of the configuration of the locking tabs and locking slots, the locking tabs and locking slots engage one another by rotating the hollow tube counterclockwise and are released by clockwise rotation.

In another embodiment, the fusion cage has internal ramps which assist in directing the bone graft material to one or more openings in the fusion cage.

In another embodiment for the integrated fusion cage and graft delivery device, the detachable fusion cage is detachable by way of receipt of an electrical, mechanical, pneumatic, hydraulic or other communication imparted by the user upon the plunger and/or hollow tube so as to detach the fusion cage and thereby deposit the fusion cage into the surgical area.

In another embodiment for the integrated fusion cage and graft delivery device, the detachable fusion cage is detachable by way of a Luer taper or Luer fitting connection, such as in a Luer-Lok® or Luer-Slip® configuration or any other Luer taper or Luer fitting connection configuration. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Patent Appl. No. 2009/0124980 to Chen.

In another embodiment for the integrated fusion cage and graft delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Patent Appl. No. 2009/0187194 to Hamada.

In another embodiment for the integrated fusion cage and graft delivery device, the detachable fusion cage is detachable by use of magnetism. More specifically, the detachable fusion cage can be made to feature a magnetic field pattern and a resulting force R that are adjustable and may be of different character than the rest of the integrated fusion cage and graft delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the integrated fusion cage and graft delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the integrated fusion cage and graft delivery device can be arranged to present one or more openings between members or portions, where such openings extend between end portions of the fusion cage. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Patent Appl. No. 2011/0015748 to Molz et al.

In another embodiment for the integrated fusion cage and graft delivery device, the detachable fusion cage is detachable by use of plasma treatment. The term "plasma" in this context is an ionized gas containing excited species such as ions, radicals, electrons and photons. (Lunk and Schmid, Contrib. *Plasma Phys.*, 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 *Polymeric Materials Encyclopedia* 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the integrated fusion cage and graft delivery device, or to provide selectable detachment of the fusion cage. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Pat. No. 7749555 to Zanella et al.

One having skill in the art will appreciate that the fusion cage may be selectably detachable to the integrated fusion cage and graft delivery device, for example, by means that mechanically grasp the head, means that attach by vacuum, and means that attach by friction, or other means known to those of skill in the art for attaching the head of an apparatus to the shaft of an apparatus.

It is another aspect of the present disclosure that the distal end of the integrated fusion cage and graft delivery device be equipped with various other tools to aid in the procedure. Such tools may include, for example, devices used to assess the condition of the implantation site and surrounding tissue. This may include, for example, a device that transmits or provides an image or signal which carries an image for visual inspection and photography. Such an image capture device may include, for example, a device to illuminate the implant site coupled with an image capture and/or transmission device. Another tool may also include, for example, a device that aids in irrigation or drainage of the surgical site, a tool used to sample or biopsy tissue.

Another embodiment for the integrated fusion cage and graft delivery device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into said hollow tube, whereby the plunger has a distal end that is contoured to an interior surface of the distal end of the hollow tube such that the contoured distal end of the plunger is nearly congruent with the interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunder along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360 degree rotation of the plunger equates to 5 cc of bone graft material delivered to the bone graft site.

Another aspect of the present invention includes providing a hollow tube and plunger assembly, in which the hollow tube and/or the plunger assembly are disposable. The tube may also be at least portions of biocompatible material which can stay in the canal without impairing the final implantation. Alternatively, it may thus be a material that is resorbable, such as a resorbable polymer, in the canal after implantation, so as not to interfere with the growth of the bone or stability of the implant.

A further embodiment of the invention provides pre-packaged inserts for loading into the hollow tube element, or if there are a plurality of hollow tube elements, into one or more of the hollow tube elements. The pre-packaged inserts may be of varying lengths, and/or layered of differing materials or components, to include the patient's own bone graft matter.

Another embodiment of the present invention provides an integrated fusion cage and graft delivery system, by which a hollow tube and/or a hollow tube/plunger assembly can be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

A further embodiment of the present invention provides a bone graft insertion apparatus comprising a hollow tube constructed to receive bone graft, the hollow tube having a proximal and distal end whereby the hollow tube contains least one opening on a surface of the distal end of the hollow tube. The at least one opening is preferably positioned other than completely along the axial or longitudinal axis of the device. The number and size and shape of such openings can vary but are preferably adapted to deliver bone graft material in a direction substantially transverse to the axial extent of the substantially hollow tube. In one embodiment, two or more apertures are provided. In certain embodiments, apertures are on the same side of the hollow tube, where in others, apertures are on different sides (e.g. opposing sides) of a hollow tube. A plunger, adapted for insertion at least partially within the hollow tube, is constructed and arranged with respect to the hollow tube so as to present at least one substantially flat contour, whereby the plunger has a distal end that is contoured to an interior surface of the distal end of the hollow tube such that the contoured distal end of the plunger is nearly congruent with the interior surface of the distal end of the hollow tube. This facilitates removing substantially all of the bone graft received by the hollow tube whereby the bone graft is delivered to the graft receiving area. It is important to remove substantially all of the bone graft material as it is expensive and/or difficult to obtain.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such as guidewires along the longitudinal axis of the shaft of the plunger.

In another embodiment of the invention, the distal end and the proximal end of the hollow tube are in communication via a conduit to enable electrical, hydraulic, pneumatic, or mechanical transmission, the later such as a wire. Such hydraulic communication allows, for example, a medical or other liquid to be delivered or extracted from the surgical area. Such mechanical communication allows, for example, the distal end to be maneuvered precisely.

In another embodiment of the present disclosure, the hollow tube and/or plunger may be curved and/or may have an angular aspect, in addition to the sloped or curved surface at a second end of the hollow tube/plunger. This shape may, for example, aid the surgeon in more comfortably introducing the delivery device to the implant site, be shaped to better accommodate implantation sites on right or left sides of the body, or be shaped to better accommodate right or left-handed surgeons. One having skill in the art will appreciate that the delivery device may have multiple angles and curved aspects which enable aspects of embodiments of the present disclosure or aid in ergonomics.

In one embodiment of the present disclosure, the device further comprises a footing or shelf at the distal end of the tubular device that is nearest the operating site for preventing or mitigating risk of injury to the patient during surgery. According to this embodiment, the footing may be flexible, semi-flexible, semi-rigid or rigid. The footing serves to protect the anatomy of the patient from being penetrated by the hollow tube of the integrated fusion cage and graft delivery device when the plunger is being inserted or during tamping of the hollow tube or the plunger by the surgeon, which may occur during the surgical procedure for a variety of reasons. In certain embodiments, the distal tip region of the hollow tube comprises a softer, maliable and/or less rigid material than the remainder of the hollow tube. For example, the distal tip could be made of a bioactive collagen.

It is yet another aspect of the present disclosure to provide an integrated fusion cage and graft delivery device that contains one or more detachable elements for use in an operation where bone graft material must be inserted into the integrated fusion cage and graft delivery device and ejected to a bone graft receiving area. According to various embodiments, these detachable devices may include a detachable funnel for gathering and inserting bone graft material at a graspable end of the integrated fusion cage and graft delivery device. The present disclosure may also comprise a plunger that has a detachable handle, which may be selectively removed to avoid blocking the surgeon's view of the operating site. The integrated fusion cage and graft delivery device may further comprise a detachable footing or shelf at one distal end of the hollow tubular member. In one embodiment this footing or shelf is selectively positionable about various points along the hollow tube. For example, a distal portion of the hollow tube has a rotatable portion that can be positioned to deliver bone graft material to areas of a disc space in a manner such that a surgeon has angular directional control as to where bone graft material is directed. Other detachable elements are also contemplated with the present invention, such as a funnel at the proximal end of the hollow tube, or exterior or interior guide wires attached to the hollow tube, or a camera which is positioned near the delivery site of the bone graft material.

In another embodiment of the invention, the device is configured such that the upper or first end of the device (that is, the end in which the plunger is inserted) is not substantially in-line with the second end of the device (that is, the end from which bone graft material is emitted and/or a fusion cage is attached). For example, the body of the hollow tube may be configured with an angle or kink along its length, appearing to be rotated along its length. In this embodiment, the plunger element is flexible and/or conformable so as to flex inside of the tube portion and otherwise traverse through the tube portion. This embodiment of the device is useful, for example, when the user requires entry to the disc space at other than a right angle. Further, the angle or kink along the length of the device may be configured is capable of selectively locking (e.g., by a pin) the upper device portion into a particular position, e.g. so that a desired angle is created between the upper device portion and the remaining portion of the device. The means for communication itself can be locked to alternatively achieve this objective. In one embodiment, when the rotating member is in an unlocked mode, the member is free to rotate in at least one plane. The selective locking mechanism can be remotely accessed by a user of the tool at the upper end of the handle by, for example, an external shaft that communicates with the locking mechanism of the rotating member on the distal end of the body. Yet another aspect of the present disclosure is that the device can be variably angled to allow for a variety of insertion angles. A ratcheting adapter can be fitted to allow for this application.

The present invention can be used in veterinary conditions, in the thoracic spine or can be used for insertion of a laterally based disk replacement.

Thus, according to various embodiments of the present disclosure, a method of introducing bone graft material to a desired operating site ("bone graft receiving area") is provided by use of a hollow tubular member comprising a generally rectangular cross-sectional area, whereby the desired operating area is capable of receiving at least one plunger. The one or more plunger having at least one distal end which is designed to accommodate ejecting bone graft or other material to be inserted into the joint space or between intervertebral members in a generally lateral direction, as opposed to a generally longitudinal direction (in relation to the direction of the primary axis of the device).

One skilled in the art will appreciate that the distal end of the tubular device need not be limited to those specific embodiments described above. Other forms, shapes or designs that enable the foregoing aspects of the present invention are hereby incorporated into this disclosure. Forms, shapes and designs that relate to the provision of an end of a tubular device to perform lateral introduction of bone or bone substitute to an operating site are considered to be within the scope of the present disclosure.

One aspect of the present invention provides an integrated fusion cage and graft delivery device system for delivering bone graft, in a partially formed, fully formed or unformed condition to a bone graft receiving area in a body.

In yet another embodiment the hollow tube of the integrated fusion cage and graft delivery device may further comprise a funnel on the graspable end of the hollow tube, which may be selectively positioned about the graspable end of the hollow tube, for facilitating insertion of new or additional bone graft into the hollow tube. The funnel may take on a variety of shapes and sizes, depending on the nature of the bone graft material being inserted in the hollow tube.

One embodiment of the substantially hollow tube provides that the hollow tube is telescoping, thereby allowing its length to be adapted to the particular desires of the surgeon and/or the surgical area. In this embodiment, the plunger may also be telescoping to substantially conform to the configuration and/or size and/or shape of the substantially hollow tube.

In another embodiment, the size and/or shape of the one or more hollow tubes of the device are sized to fit, and/or not substantially obscure access to the aperture of, the cannula or cannulas that the device is fitted through for delivery of bone graft material to the operating site. In this embodiment, the device's one or more pair of hollow tubes and plungers do not substantially impair access to the operating site nor the surgeon's view of the operating site.

In one embodiment of the invention, a bone graft insertion apparatus comprises: a hollow tube constructed to receive bone graft, said hollow tube having an extended axis and a proximal end and a distal end, said distal end having an interior surface; a plunger adapted for inserting into said proximal end of said hollow tube, said plunger having a distal end being contoured to said interior surface of said distal end of said hollow tube such that bone graft material within said hollow tube is delivered to a graft receiving area through at least one opening near the distal end of said hollow tube; wherein said graft receiving area is configured to accommodate at least one substantially hollow implant.

In another embodiment of the invention, a bone graft insertion apparatus comprises: a hollow tube constructed to receive bone graft, said hollow tube having a proximal and distal end; whereby said hollow tube contains least one opening on a surface of said distal end of said hollow tube; whereby said opening on a surface of said distal end of said hollow tube is positioned other than completely along the axial or longitudinal axis of the device; a plunger adapted for insertion at least partially within said hollow tube at proximal end of said hollow tube; whereby said plunger is constructed and arranged with respect to said hollow tube so as to present at least one substantially flat contour; whereby said plunger has a distal end that is contoured to an interior surface of said distal end of said hollow tube such that said contoured distal end of said plunger is nearly congruent with said interior surface of said distal end of said hollow tube for removing substantially all of said bone graft received by said hollow tube; whereby said bone graft is delivered to a graft receiving area.

In another embodiment of the invention, a method of inserting bone graft comprises: preparing a surgical area to receive bone graft; inserting a tool into said surgical area, said tool consisting essentially of a hollow tube adapted to receive bone graft, a plunger adapted for insertion into said hollow tube, said plunger constructed to prevent rotation during insertion into said hollow tube, said plunger having a distal end contoured to the interior surface of the distal end of said hollow tube; providing bone graft material into the said hollow tube of said tool; inserting said plunger into the proximal end of said hollow tube; inserting said distal end of said hollow tube of said tool into surgical area; applying force to said plunger thereby advancing said plunger through said hollow tube wherein said bone graft is inserted into said surgical area.

In another embodiment of the invention, an integrated fusion cage and graft delivery device apparatus comprises: a hollow tube constructed to receive bone graft, the hollow tube having an extended axis and a proximal end and a distal end, the distal end having an interior surface; a plunger adapted for inserting into the proximal end of the hollow tube, the plunger having a distal end being contoured to the interior surface of the distal end of the hollow tube; a selectably detachable fusion cage, the selectably detachable fusion cage having at least one opening that substantially aligns with at least one opening near the distal end of the hollow tube, such that bone graft material within the hollow tube is delivered to a graft receiving area through at least one opening of the selectably detachable fusion cage; and the selectably detachable fusion cage having a means for detachment whereby the fusion cage is delivered to the graft receiving area.

In one embodiment, the device is not a caulking gun style device, that is the bone graft material and/or the fusion cage are not delivered and/or positioned using a hand-pump and/or hand-squeeze mechanism. Instead, the device delivers graft material and/or a fusion cage using a hollow tube and plunger arrangement which is not a caulking gun style device and further, does not appreciably disrupt or block the user's view of the surgical site and/or enable precision delivery of bone graft material and/or a fusion cage to the surgical site. Indeed, the device is distinctly unlike the chalking gun device of U.S. Pat. Appl. No. 2004/0215201 to Lieberman ("Lieberman"), which requires an L-shaped base member handle, rack teeth to advance a plunger member, and user action on a lever of the L-shaped base member handle to deploy bone graft material. In one embodiment, the device of this application is not a caulking gun style device and does not comprise rack teeth, a base member handle and at least one component that obscures user viewing of the surgical site. Lieberman is incorporated by reference in its entirety for all purposes.

Similarly, in one embodiment, the device is distinctly unlike the chalking gun device of U.S. Pat. Appl. No. 2002/0049448 to Sand et al ("Sand"), which requires a gun and trigger mechanism in which the user squeezes together a gun-style handle to deploy material into bone. The Sand device obstructs the view of the user of the delivery site. In one embodiment, the device of this application is not a caulking gun style device and does not comprise an opposing-levered, gun-style delivery mechanism and at least one component that obscures user viewing of the surgical site. Sand is incorporated by reference in its entirety for all purposes.

In one embodiment, the device is configured to deliver bone graft material substantially laterally from its delivery end, that is substantially not in the axial direction but rather substantially from the side and/or in a radial direction. This is distinctly different than devices that deliver bone graft material along their vertical axis, that is, along or out their bottom end, and/or obstruct the user view of the bone graft and/or fusion cage delivery site, such as that of U.S. Pat. Appl. No. 2010/0087828 to Krueger et al ("Krueger"), U.S. Pat. Appl. No. 2009/0264892 to Beyar et al ("Beyar"), U.S. Pat. Appl. No. 2007/0185496 to Beckman et al ("Beckman"), U.S. Pat. Appl. No. 2009/0275995 to Truckai et al ("Truckai")and U.S. Pat. Appl. No. 2006/0264964 to Scifert et al ("Scifert"). Krueger, Beyar, Beckman, Truckai and Scifert are incorporated by reference in their entireties for all purposes.

In one embodiment, the device is configured to deliver bone graft material so as to completely fill the defined interior of its fusion cage and subsequently deliver bone graft material to the surrounding bone graft site, rather than, for example, to contain the bone material as are the fusion cage designs of U.S. Pat. No. 7,846,210 to Perez-Cruet ("Perez-Cruet"). Further, the fusion device of this application features a distal tip that functions to precisely position the fusion device and stabilize the device during delivery of bone graft material. Perez-Cruet is incorporated by reference in its entirety for all purposes.

In one embodiment, a bone graft insertion apparatus is disclosed, the bone graft insertion apparatus comprising: a hollow tube constructed to receive bone graft, said hollow tube having an extended axis and a proximal end and a distal end, said distal end having a substantially tapered distal tip interior surface and a distal end interior surface of rectangular cross-section; a plunger adapted for inserting into said proximal end of said hollow tube, said plunger having a distal end exterior surface of rectangular cross-section contoured to said distal end interior surface of said hollow tube, said plunger having a substantially tapered distal tip contoured to said substantially tapered distal tip interior surface of said hollow tube to form a substantially congruent fit, wherein bone graft material within said hollow tube is delivered to a graft receiving area through one or more lateral openings near said distal end of said hollow tube, said one or more lateral openings substantially precluding the delivery of bone graft material directly along said axis of said hollow tube, said plunger precluded from rotating when inserted into said hollow tube.

In another embodiment, a bone graft insertion apparatus is disclosed, the bone graft insertion apparatus comprising: a hollow tube having a length, a proximal end and a distal end, said hollow tube having a rectangular cross-section, said distal end having a tapered tip interior surface and at least one opening; a plunger adapted for insertion within said hollow tube at said proximal end of said hollow tube, said plunger having a rectangular cross-section end portion and a distal tip contoured to conform to the distal end of said hollow tube, said plunger having a length sufficient such that when fully inserted into said hollow tube, said plunger distal end contacts at least one opening.

In another embodiment, a bone graft insertion apparatus is disclosed, the bone graft insertion apparatus comprising: a hollow tube constructed to receive bone graft having an extended axis, a length, a proximal end and a distal end, said hollow tube having a rectangular cross-section, said distal end having a tapered tip interior surface with a terminus and two oval-shaped openings having an upper and a lower end located on opposite lateral sides of said distal end, said tapered tip extending into said hollow tube and said terminus positioned adjacent to said oval-shaped openings; a plunger adapted for insertion within said hollow tube at said proximal end of said hollow tube, said plunger having a rectangular cross-section end portion and a distal lower surface, said plunger having a length sufficient such that when fully inserted into said hollow tube, said plunger distal lower surface contacts said hollow tube terminus at a position adjacent to said oval-shaped openings, said plunger rectangular cross-section end portion forming a continuous surface adjacent each of the oval-shaped openings from a position opposite said terminus to a point extending beyond said upper end of each oval-shaped opening; wherein bone graft material within said hollow tube is delivered to a graft receiving area through said oval-shaped openings of said hollow tube, said oval-shaped openings precluding the delivery of bone graft material directly along said axis of said hollow tube, said plunger precluded from rotating when inserted into said hollow tube; wherein said oval-shaped openings near the distal end of said hollow tube are positioned within a 25% length from said distal end relative to a total length of said hollow tube.

One of ordinary skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. The plunger element could be flexible, semi-rigid, or rigid and made of materials such as stainless steel, titanium alloy, aluminum alloy, chromium alloy, and other metals or metal alloys. Similarly, the tubular element could be flexible, semi-rigid, or rigid and made of materials such as stainless steel, titanium alloy, aluminum alloy, chromium alloy, and other metals or metal alloys. In certain embodiments, the plunger and hollow tube are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the hollow tube and/or plunger are made of a substantially transparent material and/or are rigidly opaque.

In one embodiment of the fusion cage, the fusion cage comprises a polymer, such as PEEK, titanium and composite materials.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the speed of the procedure, the minimally invasive aspect of the procedure, the ability to introduce the implant material to the implant site with minimal risk and damage to the surrounding tissue, the lower risk of infection, more optimally placed implant material, a more stable delivery device which is designed to reduce the likelihood of the implant material becoming dislodged prior to fixation, and fewer tools in a surgical site due to the integration of several components required to provide bone graft to a bone graft receiving area. Further, the lower profile of the device allows improved viewing of the area intended for receipt of bone graft material, and use of a reduced set and size of elements therein provided a less expensive device. Also, the device disclosed provides that substantially all of the bone graft material may be ejected from the device and delivered to the surgical site, rather than wasted as unretrievable matter remaining inside the device. The ability to remove substantially all of the bone graft material is of significant benefit because the bone graft material is expensive and/or hard to obtain.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 1A is a front perspective view of the device for delivering bone graft;

FIG. 1B is a front perspective view of the plunger of the device;

FIG. 1C is a cross sectional view of a portion of the device shown in FIG. 1A;

FIG. 6 is a front perspective view of one embodiment of the device, showing the relationship between the tubular and plunger portions where the tubular portion includes two lateral facing openings at the distal end of the tubular portion and a wedge-shaped distal end of the tubular member;

FIG. 7 is another front perspective view of the tubular portion of the device of FIG. 6 showing the second of two lateral openings at the distal end of the tubular portion and a wedge-shaped distal end of the tubular member;

FIG. 8 is a front elevation view of the distal end of the tubular portion of the device of FIG. 6;

FIG. 9 is a bottom elevation view of the proximal end of the tubular device of FIG. 6;

FIG. 10A is a top plan view of the device of FIG. 6 with the plunger portion fully inserted into the tubular portion;

FIG. 10B is a left elevation view of the device of FIG. 6 with the plunger portion fully inserted into the tubular portion;

FIG. 10C is a bottom plan view of the device of FIG. 6 with the plunger portion fully inserted into the tubular portion;

FIG. 10D is a right elevation view of the device of FIG. 6 with the plunger portion fully inserted into the tubular portion;

FIG. 19A is a top plan view of a fusion cage of an embodiment of the device particularly adapted for use in anterior lumbar interbody fusion procedures;

FIG. 19B is a front elevation view of the device of FIG. 19A;

FIG. 19C is a left elevation view of the device of FIG. 19A;

FIG. 19D is a view of the device of FIG. 19A inserted between vertebrae;

FIGS. 45A-G provide scaled views of one embodiment of the fusion cage element of yet another embodiment of the integrated fusion cage and graft delivery device configured to operate with the hollow tube of FIGS. 46A-H, plunger of FIGS. 47A-D and ejection tool of FIGS. 48A-E;

FIGS. 46A-H provide scaled views of one embodiment of the hollow tube (aka snap on cannula) of the integrated fusion cage and graft delivery device configured to operate with the fusion cage element of Figs.45A-G, plunger of FIGS. 47A-D and ejection tool of FIGS. 48A-E;

FIGS. 47A-D provide scaled views of one embodiment of the plunger (aka snap on plunger) of the integrated fusion cage and graft delivery device configured to operate with the fusion cage element of FIGS. 45A-G, hollow tube of FIGS. 46A-H, and ejection tool of FIGS. 48A-E; and FIGS. 48A-E provide scaled views of one embodiment of the ejection tool (aka cage insertion tool) of the integrated fusion cage and graft delivery device configured to operate with the fusion cage element of FIGS. 45A-G, hollow tube of FIGS. 46A-H and plunger of FIGS. 47A-D.

DETAILED DESCRIPTION

Figure 2:
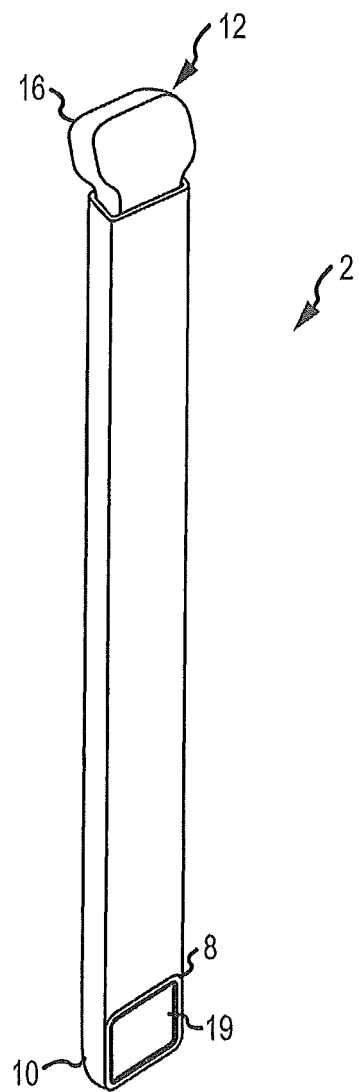
FIG. 2 is another front perspective view of the device of FIGS. 1A and 1B, showing the relationship between the tubular and plunger portions of the device.

The present invention relates to a device and method for integrated and near-simultaneous delivery of bone graft material and a fusion cage to any portion of a patient which requires bone graft material and/or a fusion cage. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The integrated fusion cage and graft delivery device is formed such that the one or more hollow tubes and/or plungers may be helpful in selectively and controllably placing bone graft material and a fusion cage in or adjacent to such window. The integrated fusion cage and graft delivery device is formed to allow delivery of bone graft material and/or a fusion cage in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present invention also contemplates the delivery of bone graft material and/or a fusion cage with or without the use of a plunger, and with or without the use of various other tools described in greater detail herein.

Referring now to FIGS. 1-33 and 36-45, several embodiments of the present invention are shown.

In regard to FIG. 1A, an integrated fusion cage and graft delivery device portion is shown, which is comprised of a hollow tubular member or hollow tube or contains at least one inner lumen 2, which has a first proximate end 6 (which is referred to elsewhere in this specification as the "graspable end" of hollow tube 2), and a second distal end 8, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the second end 8. According to a preferred embodiment, the hollow tube 2 also comprises at least one sloped or curved surface 10 at or near the second end 8 of the hollow tube 2. Although a generally rectangular cross-section is depicted, the cross-section need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space.

Referring now in detail to FIG. 1B, a plunger 12 is shown for use with the hollow tube 2 of FIG. 1A. The plunger 12 is generally of the same geometry as the hollow portion of the hollow tube 2, extending at least the same length of hollow tube 2. The plunger 12 may includes, as depicted in FIG. 1B at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat, horizontal surface 19, which corresponds to the opening at the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the horizontal surface 19 of plunger 12 is in communication with the second end 8 of the hollow tube 2. This configuration permits a user to eject substantially all of the bone graft material that is placed into the hollow tube 2 during a surgical procedure. One skilled in the art will appreciate that the plunger need not terminate in a generally flat, horizontal surface to effect the substantial removal of all of the bone graft material placed into the hollow tube; more specifically, any shape that allows conformance between the internal contour of the distal end of the hollow tube and the distal end of the plunger will effect the substantial removal of the bone graft material. Further details about the relationship are described below in regard to FIG. 2.

In the embodiment, of FIG. 1A-C, a contoured leading edge is provided on the plunger to correspond with the internal contour of distal end of the hollow tube of the delivery device. This contoured plunger serves several purposes: First, it maintains the plunger in a desirable rotational position with respect to the hollow tube (i.e., prevents the plunger from inadvertently or intentionally being manipulated to rotate about the longitudinal axis of the hollow tube). Second, it ensure that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. Alternative positioning means may also be provided to ensure that the plunger remains in the desirable position during delivery of bone graft into the hollow tube, for example by a machined bevel or edge on the outer surface of the plunger, and a corresponding groove in the interior surface of the hollow tube, which must be aligned when inserting the plunger in the hollow tube.

Referring now to FIG. 1C, an elevation view of the hollow tube 2 shown in FIG. 1A is shown in detail. The second end 8 of the hollow tube 2 has an opening with a height A and width B according to the needs of the surgeon, the location of the bone graft receiving area, the nature of the surgical operation to be performed, and the quantity and type of bone graft that is being inserted in (and ultimately ejected from) this integrated fusion cage and graft delivery device. According to a preferred embodiment, the height A of the opening at the second end 8 of the hollow tube 2 is in the range of 4 mm to 9 mm, and in a most preferred embodiment is about 7 mm. According to a preferred embodiment, the width B of the opening at the second end 8 of the hollow tube 2 is in the range of 7 mm to 14 mm, and in a most preferred embodiment is about 10 mm.

Referring to FIGS. 1A-C, it is to be understood that although these particular drawings reflect an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, that in other embodiments, the second end 8 of the hollow tube 2 (and thereby, the second end 18 of the plunger 12) do not extend a lateral distance away, but rather terminate along the longitudinal wall of the hollow tube 2. In this embodiment, the hollow tube 2 may have a second end 8 which has an opening that is carved out of the side of the wall of the hollow tube 2, such that it appears as a window in the tubular body of hollow tube 2. According to this embodiment, the horizontal face 19 of the plunger 12 would also be a face on the outer surface of plunger 12, without extending any lateral distance away from the body of plunger 12. According to this embodiment, the plunger 12 would still retain the curved or sloped surface at the opposite end of the horizontal face 19 (referred to in FIG. 1B as 20) and similarly the hollow tube 2 would still comprise a sloped or curved surface 10 opposite the opening at second end 8. It is to be expressly understood that other variations which deviate from the drawing FIGS. 1A-C are also contemplated with the present invention, so long as that the opening at the second end 8 of hollow tube 2 is oriented to permit bone graft to be exited from the hollow tube 2 in a generally lateral direction (in relation to the longitudinal direction of the axis of the hollow tube 2).

According to another embodiment, the plunger 12 shown in FIG. 1B may further comprise a secondary handle (not shown in FIG. 1B), which includes an opening about at least one end of secondary handle such that it is permitted to couple with handle 16 of plunger 12. In this fashion, the secondary handle may be larger, contain one or more rings or apertures for placing a users hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Referring now in detail to FIG. 2, the plunger 12 is shown inserted into the hollow tube 2, such that the horizontal face 19 is substantially planar with the opening at the second end 8 of the hollow tube 2. As described above, the geometry of plunger 12 is such that it fits snuggly or tightly in the interior of the hollow tube 2. This configuration is such that the sloped or curved surface 10 of the hollow tube 2 is substantially congruent to the sloped or curved surface 20 (not shown in FIG. 2), thereby allowing the plunger to be inserted into the hollow tube 2 and allowing substantially all of bone graft material which is placed into the hollow tube 2 to be ejected by the user.

Figure 3:
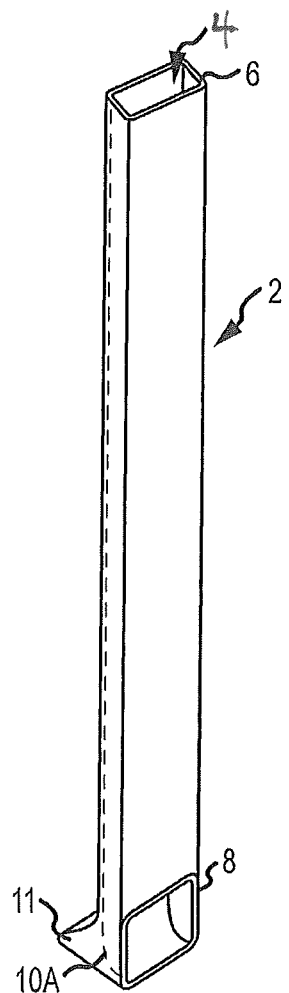
FIG. 3 is a front perspective view of the device according to one alternative embodiment where the tubular portion includes a foot section and where the plunger portion has been fully inserted into the tublular portion.

Referring now in detail to FIG. 3, an alternate embodiment of the present invention is shown. According to this embodiment, the hollow tube 2 comprises a footing 11 at the second end 8 of the hollow tube 2. This footing 11 extends in a lateral direction, opposite the direction of the opening at the second end 8 of the hollow tube 2. The purpose of this footing 11 is to prevent injury to the annulus of a patient, or other sensitive anatomy adjacent the bone graft receiving area. This footing 11 is helpful when a surgeon or other user of the integrated fusion cage and graft delivery device is using the plunger 12 to drive bone graft through the hollow tube 2, or using another tool, such as a tamp, mallet, or other driving or impacting device to strike the plunger 12 and/or hollow tube 2 during the surgical procedure. Without the footing 11, the hollow tube 2 would have a generally angular second end 8, which may cause damage to the patient during these types of procedures. Thus, the footing 11 prevents the second end 8 of the hollow tube 2 from penetrating the annulus or other sensitive anatomy of the patient.

According to this embodiment, the footing 11 may also operate to ensure a fixed position of the second end 8 of the hollow tube 2 in the surgical site. This in turn allows a user to ensure that bone graft ejecting the second end 8 of the hollow tube 2 is being ejected laterally, and in the desired direction. This may be important, for example, when the integrated fusion cage and graft delivery device is placed within a disc space, and bone graft is being ejected laterally from the second end 8 of the hollow tube 2 in a specific direction. In other embodiments, the footing 11 may also serve as a visual marker for the surgeon, as it extends away from the horizontal wall of the hollow tube 2, and is therefore visible at the second end 8 of the hollow tube 2. As shown in FIG. 3, the presence of the footing 11 does not affect the interior slope or curved surface 10A of the hollow tube 2, so that the plunger 12 of the design shown in FIG. 1B may still be used with the hollow tube 2 of this alternate embodiment.

Figure 4:
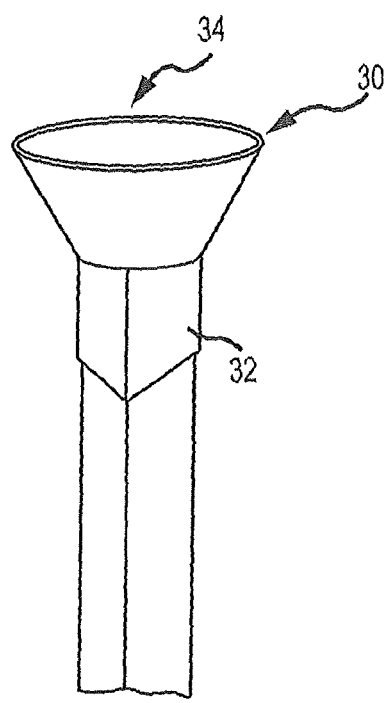
FIG. 4 is a partial front perspective view of another alternative embodiment of the device where the tubular portion includes a funnel at its proximal end designed to receive bone graft.

Referring now in detail to FIG. 4, a removable funnel 30 is shown, which comprises an opening 34 which is generally larger in diameter or dimension when compared to the opening 4 of the hollow tube 2. This removable funnel 30 further comprises a sleeve 32, the sleeve 32 having an internal cross-section which is substantially congruent with the external cross-section of the first end 6 of the hollow tube 2. Thus, according to this embodiment, the funnel 30 is selectively removable from the first end 6 of the hollow tube 2, and may allow a surgeon to more easily place new or additional bone graft into the hollow tube 2 by way of the opening 34 of the funnel 30. This funnel 30 may be used in connection with a hollow tube 2 that has been pre-filled with bone graft, or a hollow tube which is not pre-filled with bone graft. Thus, the funnel may be selectively positioned on the first end 6 of the hollow tube 2 at any point during the surgical operation when the surgeon desires new or additional bone graft be placed in the hollow tube 2 of the integrated fusion cage and graft delivery device.

Figure 5:
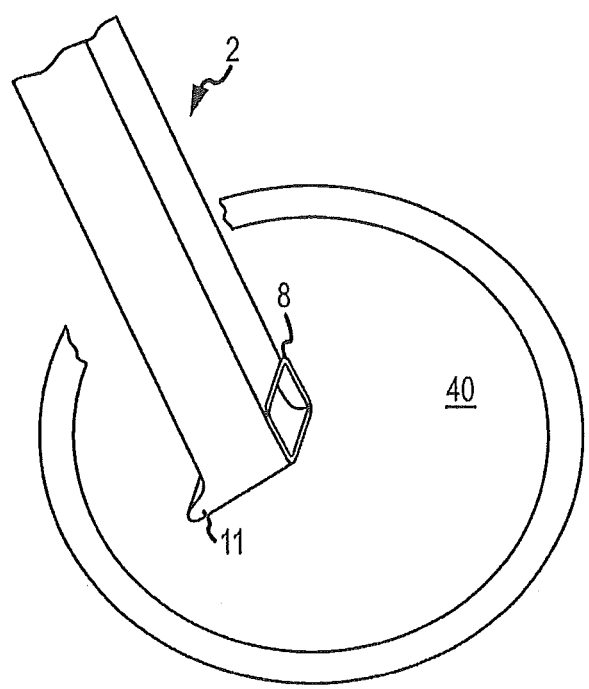
FIG. 5 is a partial front perspective view of the device according to one embodiment where the device is positioned in a disc space during a surgical operation.
Figure 11A:
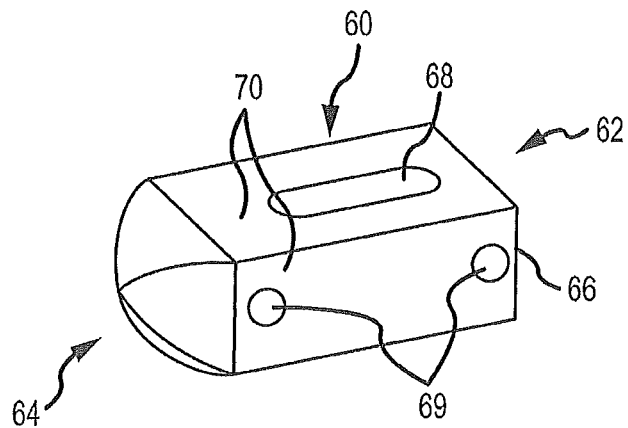
FIG. 11A is a front perspective view of one embodiment of the fusion cage of the device, showing a tapered proximal end and medial openings.
Figure 11B:
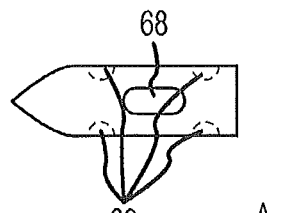
FIG. 11B is a top plan view of the fusion cage of FIG. 11A.
Figure 11C:
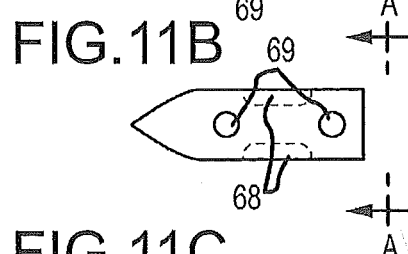
FIG. 11C is a left elevation view of the fusion cage of FIG. 11A.
Figure 11D:
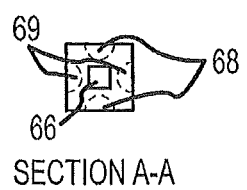
FIG. 11D is a rear elevation view of the fusion cage of FIG. 11A.

Referring now in detail to FIG. 5, one particular application of the integrated fusion cage and graft delivery device is shown in a perspective view. Here, the integrated fusion cage and graft delivery device is shown with the embodiment of the hollow tube 2 further comprising a footing 11, and a second end opening for ejecting bone graft in a generally lateral direction, here in the interior of a disc space 40. The disc is shown with an opening on one end for inserting the second end 8 of the hollow tube 2 of the integrated fusion cage and graft delivery device. As opposed to prior art integrated fusion cage and graft delivery devices which have an opening at a second end that is open to the longitudinal axis of the delivery device, the present invention comprises a lateral opening, which as shown in FIG. 5 allows a surgeon to eject bone mill into the lateral direction and thereby into the opened areas of the disc space 40. A surgeon has the option to rotate the direction of the opening in the second end 8 of the hollow tube 2 for ejecting additional bone graft to other open areas in the disc space 40. Once the disc space 40 is substantially full of bone graft, the surgeon may remove the hollow tube 2 without disturbing the disc or anatomy of the patient. The surgeon may also accomplish the delivery of bone graft without displacing any cage or other structural implantable device which may be present in or adjacent the disc space. One skilled in the art will appreciate that the hollow tube 2 further comprising a footing 11, and a second end opening for ejecting bone graft in a generally lateral direction, may effect the delivery of bone graft in a lateral direction simultaneous with delivery in a longitudinal direction.

Referring now to FIGS. 6-10, a preferred embodiment of the device is shown. In regard to FIG. 6, a integrated fusion cage and graft delivery device portion is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable (the other is viewable in FIG. 7). Also in FIG. 6, the plunger member 12 is shown. The manner of insertion of plunger member 12 into tubular member 2 is also provided. Thus, as shown in FIG. 6, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2.

Furthermore regarding FIG. 6, a preferred embodiment of the distal end 10 of the tubular member 2 and the distal end 20 of the plunger member 12 is provided. The configuration provided, a wedge-shaped end 50 of the tubular member and a wedge-shaped end of the plunger 52, allows substantially all of the bone graft material to be removed and thus inserted into the surgical area when the plunger 2 is fully inserted into the tubular member 2. The wedge-shaped feature 50 of the distal end 10 of the tubular member 2 and the wedge-shaped end 52 of the distal end 20 of the plunger member 12 is discussed in additional detail with respect to FIGS. 8 and 9 below. The ability to remove substantially all of the bone graft material is an important feature of the invention because bone graft material is traditionally expensive and may require surgery to obtain.

Referring now to FIG. 7, a perspective view of a preferred embodiment of the hollow tubular member 2 is provided. Consistent with FIG. 6, the generally hollow tube 2 is shown with one of two lateral openings at the distal end 8 of the tubular member 2 viewable (the other is viewable in FIG. 6). Thus, in operation the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2. In this configuration, bone graft material is ejected into the surgical area in two lateral directions. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Referring now to FIG. 8, an elevation view of the wedge-shaped distal end 50 of the tubular member 2 is provided. In this embodiment, the proximal end of the plunger would conform to the same shape, to allow close fitting of the plunger and the hollow tubular member. This contoured plunger, corresponding to the contoured tubular member, serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensure that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. One skilled in the art will appreciate that the plunger need not terminate in a wedge-shape surface to effect the substantial removal of all of the bone graft material placed into the hollow tube; more specifically, any shape that allows conformance between the internal contour of the distal end of the hollow tube and the distal end of the plunger will effect the substantial removal of the bone graft material.

Referring now to FIG. 9, an elevation view of the opening 4 of the distal end 6 of the hollow tubular member 2 is provided. As shown in FIG. 9, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, cross-sections of an oval shape or those with at least one defined angle to include obtruse, acute, and right angles can provide a shape in some situations that is more congruent with the size or shape of the annulotomy of a particular disc space.

Referring to FIGS. 10A-D, sequential elevation views of the square-shaped embodiment of the integrated fusion cage and graft delivery device 1 are provided, depicting the complete insertion of the plunger 12 into the hollow tubular member 2. In each of FIGS. 10A-D, the wedge-shaped distal end 50 of the tubular member 2 is depicted. Also, each of FIGS. 10A-D depict the additional length of the plunger element 12 when inserted into the tubular member 2. FIG. 10A shows one of two lateral openings at the distal end 8 of the hollow tubular member 2. FIG. 10C shows another of the two lateral openings at the distal end 8 of the hollow tubular member 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Referring to FIGS. 11A-D, a fusion cage 60 of an integrated fusion cage and graft delivery device 1 portion is shown, which is comprised of a integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may comprise one or more medial openings 68 that align with one or more openings at the distal end 8 of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted in to the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 and/or the bone graft delivery portion of the integrated fusion cage and graft delivery device is of oblong or rectangular or square shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

In a preferred embodiment, the fusion cage 60 has a keel-shaped tip to separate disk and prevent annular penetration. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 12A:
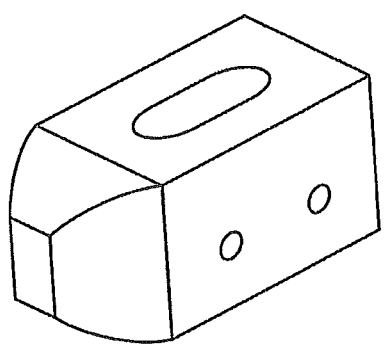
FIG. 12A is a front perspective view of another embodiment of the fusion cage of the device.
Figure 12B:
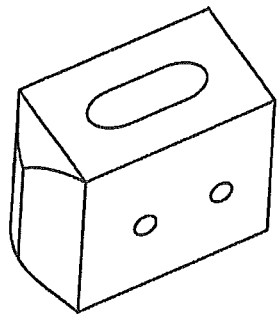
FIG. 12B is a front perspective view of yet another embodiment of the fusion cage of the device.
Figure 12C:
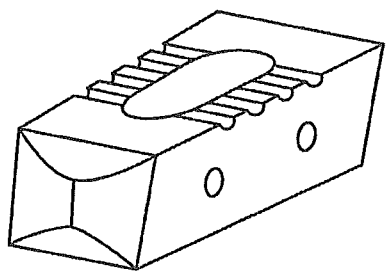
FIG. 12C is a front perspective view of yet another embodiment of the fusion cage of the device.

Referring now to FIGS. 12A-C, two alternate embodiments of the fusion cage 60 are provided. FIG. 12A shows an embodiment of the integrated fusion cage 60 with a second distal end 64 tapered to a flat rectangular shape end. FIG. 12B shows an embodiment of the integrated fusion cage 60 with a second distal end 64 tapered to a wedged-shaped end. Such a configuration would be, for example, would be conformal with the wedge-shaped second end 50 of the hollow tube 2, as shown in FIGS. 6-8. FIG. 12C shows an embodiment of the integrated fusion cage 60 with belts of striations imparted to the upper medial surface 70 of the fusion cage 60.

Figure 13:
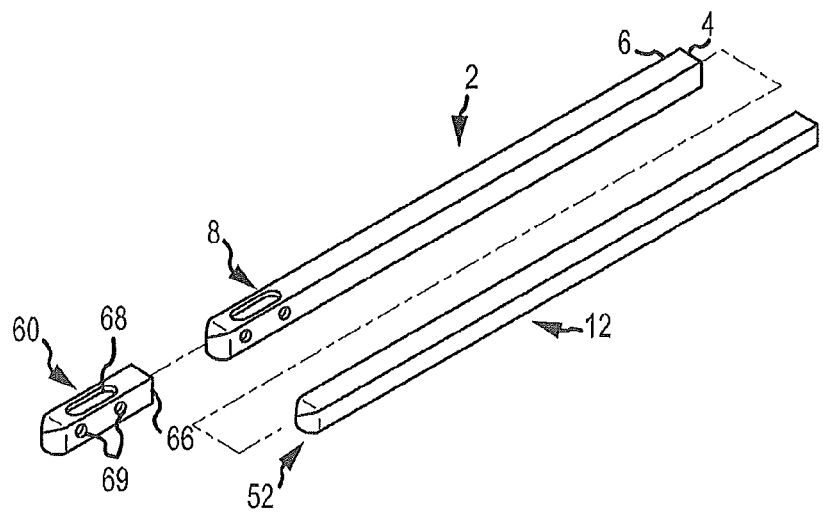
FIG. 13 is a front perspective view of one embodiment of the device, showing the relationship between the tubular and plunger portions where the tubular portion includes two lateral facing openings at the distal end of the tubular portion and a wedge-shaped distal end of the tubular member, and a fusion cage fitting over the exterior distal end of the tubular member.
Figure 14A:
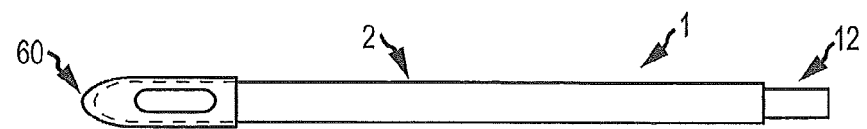
FIG. 14A is a top plan view of the device of FIG. 13 with the plunger portion fully inserted into the tubular portion and the fusion cage fully inserted over the tubular portion.
Figure 14B:
FIG. 14B is a left elevation view of the device of FIG. 13 with the plunger portion fully inserted into the tubular portion and the fusion cage fully inserted over the tubular portion.
Figure 14C:
FIG. 14C is a bottom plan view of the device of FIG. 13 with the plunger portion fully inserted into the tubular portion and the fusion cage fully inserted over the tubular portion.
Figure 14D:
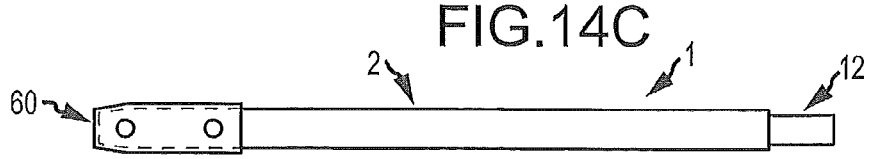
FIG. 14D is a right elevation view of the device of FIG. 13 with the plunger portion fully inserted into the tubular portion and the fusion cage fully inserted over the tubular portion.

In regard to FIG. 13, an integrated fusion cage and graft delivery device 1 is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable. Also in FIG. 13, the plunger member 12 is shown and the fusion cage 60. The manner of insertion of plunger member 12 into tubular member 2 is also provided, as is the manner of insertion of fusion cage 60 over tubular member 2 and into the fusion cage first end opening 66. Thus, as shown in FIG. 13, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2 and through the medial openings 68 and/or the lateral openings 69 of the fusion cage 60. In one embodiment as shown in FIG. 13, the lateral openings at the distal end 8 of the hollow tubular member 2 are preferably disposed within a distance from the distal end 8 not exceeding 25% of the total distance (or length) of the hollow tube member 2, more preferably not exceeding 15% of this identified distance, and most preferably not exceeding 10% of this identified distance. In one embodiment as shown in FIG. 13, the lateral openings at the distal end 8 of the hollow tubular member 2 are preferably disposed within a distance from the distal end 8 not exceeding 10 cm of the total distance (or length) of the hollow tube member 2, more preferably not exceeding 8 cm of this identified distance, and most preferably not exceeding 5 cm of this identified distance.

Referring to FIGS. 14A-D, sequential elevation views of the square-shaped embodiment of the integrated fusion cage and graft delivery device 1 are provided, depicting sequential elevation views of the integrated fusion cage and graft delivery device 1 with the plunger portion 12 fully inserted into the tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral and medial openings may vary, for example the distal end 8 of the tubular member 2 may have more than two openings that are of different shape (e.g. oval, rectangular).

Referring to FIGS. 15A-D, a fusion cage 60 of an integrated fusion cage and graft delivery device portion is shown, which is comprised of a integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted in to the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 is of a square shape and the bone graft delivery portion of the integrated fusion cage and graft delivery device is of a cylindrical shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

Figure 15A:
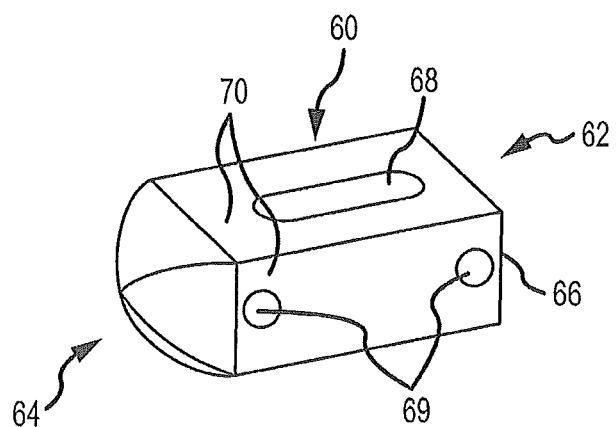
FIG. 15A is a front perspective view of another embodiment of the fusion cage of the device.
Figure 15B:
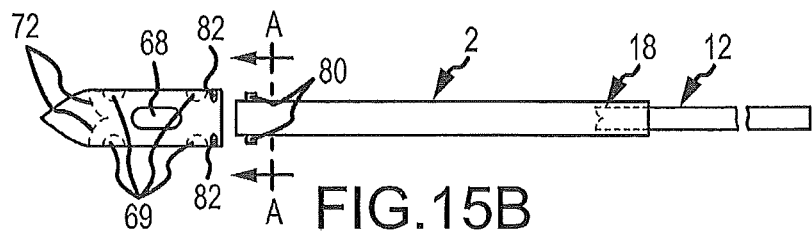
FIG. 15B is a top plan view of another embodiment of the device wherein the fusion cage of the device includes internal ramps and locking slots configured to engage locking tabs of the tubular portion, and the plunger includes a tapered tip.

In a preferred embodiment, the fusion cage 60 has a keel-shaped tip to separate disk and prevent annular penetration and has internal ramps 72 which assist in directing the bone graft material to one or more lateral openings 69. As the plunger 12 is inserted into the hollow tube 2, bone graft material is directed by the fusion cage internal ramps 72 out the lateral openings 69, and bone additionally bone graft material may flow out the one or more medial openings 68. The plunger end 18 may be configured to be conformal with the internal ramps 72 of the fusion cage 60, as depicted in FIG. 15B. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 15C:
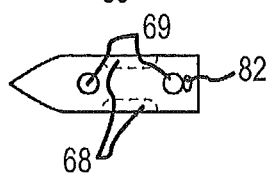
FIG. 15C is a left elevation view of the fusion cage of FIG. 15B.
Figure 15D:
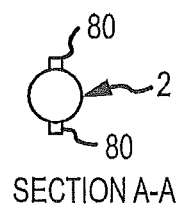
FIG. 15D is a front elevation view of the tubular portion of FIG. 15B.

In a preferred embodiment as shown in FIGS. 15B-D, the hollow tube 2 is of cylindrical shape and includes one or more locking tabs 80 configured to engage one or more locking slots 82 of the fusion cage 60. The locking tabs 80 may permanently or not permanently engage the locking slots 82, and may be of shape to include rectangular, circular and oblong. The instruments used with the integrated fusion cage and graft delivery device described above in its varying embodiments may include one or more tamps, preferably having a configuration which at least in part corresponds in shape and contour of the hollow tube portion of the delivery device. The one or more tamps may be adapted to correspond further to the shape and contour of the graspable end of the plunger, for use in driving the plunger through the hollow tube portion of the delivery device to ensure any remaining bone graft located in the hollow tube is delivered to the graft receiving area.

Figure 16:
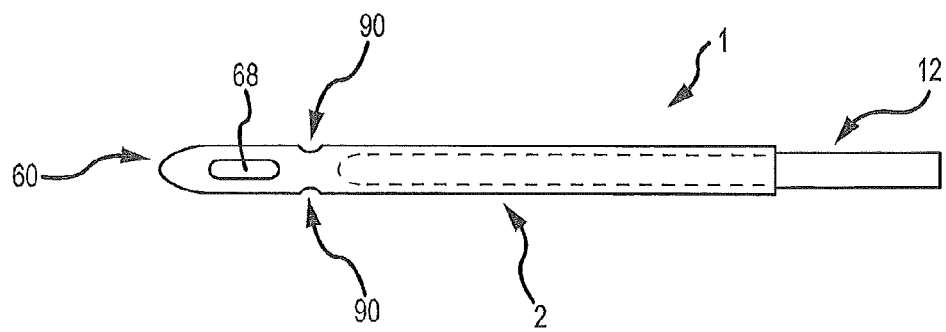
FIG. 16 is a top plan view of another embodiment of the device with the plunger portion partial inserted into the tubular portion and the fusion cage engaged with the tubular portion via a break-off collar.

In the embodiment of the device of FIG. 16, the hollow tube 2 engages with the fusion cage 60 via a break-off collar 90 and the plunger 12 inserts into the interior of the hollow tube 2. The plunger 12 is depicted partially inserted into the hollow tube 2. The break-off collar 90 may be severed by any of several means, to include application of torsion and/or rotational force and/or lateral force to break-off collar 90, for example by twisting on the hollow tube 2 and/or the plunger 12.

Figure 17A:
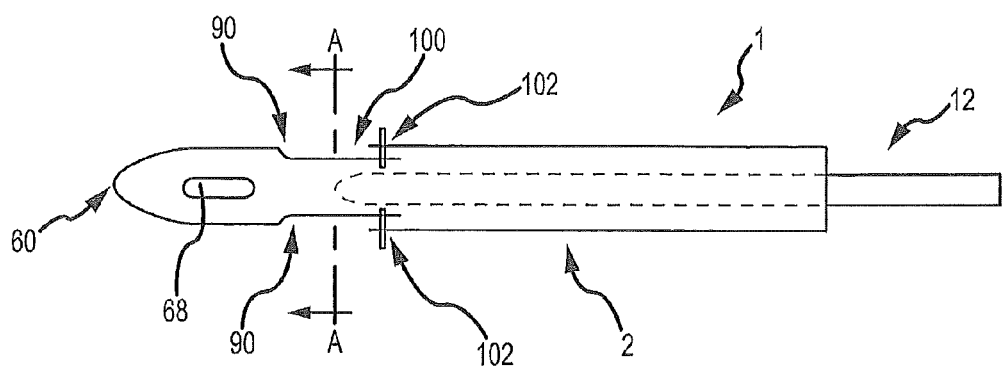
FIG. 17A is a top plan view of another embodiment of the device wherein the fusion cage engages with a connector conduit which in turn engages with the tubular portion.
Figure 17B:
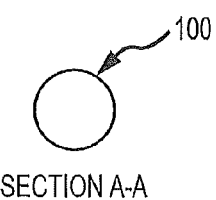
FIG. 17B is a cross-sectional view of section A-A of FIG. 17A.
Figure 18A:
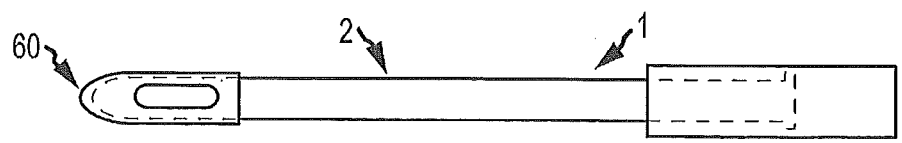
FIG. 18A is a top plan view of another embodiment of the device wherein the tubular portion comprises a telescoping feature.
Figure 18B:
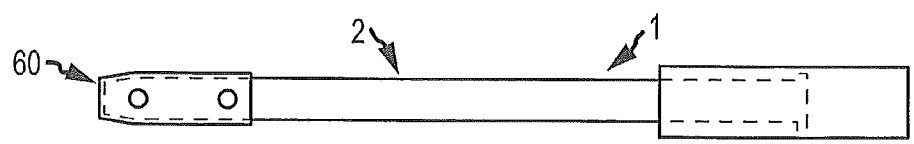
FIG. 18B is a left elevation view of the device of FIG. 18A.
Figure 18C:
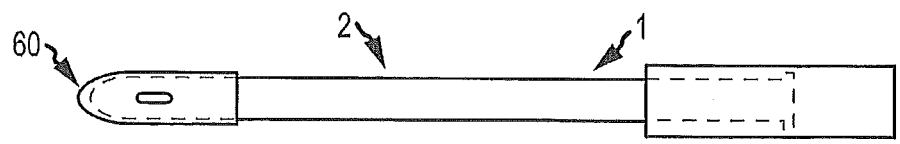
FIG. 18C is a bottom plan view of the device of FIG. 18A.
Figure 18D:
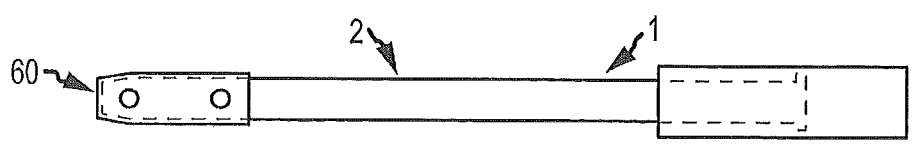
FIG. 18D is a right elevation view of the device of FIG. 18A.
Figure 20A:
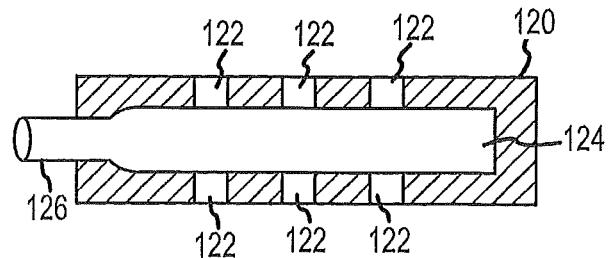
FIG. 20A is a cross-sectional top plan view of a fusion cage of an embodiment of the device particularly adapted for use in direct lateral interbody fusion procedures.
Figure 20B:
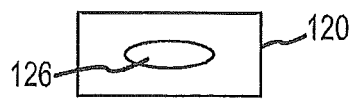
FIG. 20B is a front elevation view of the device of FIG. 20A.
Figure 20C:
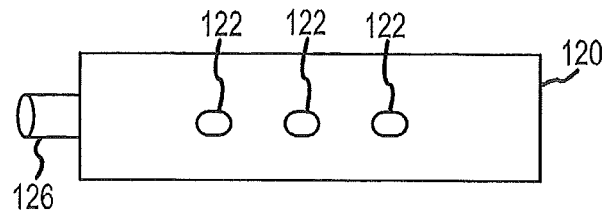
FIG. 20C is a left elevation view of the device of FIG. 20A.
Figure 20D:
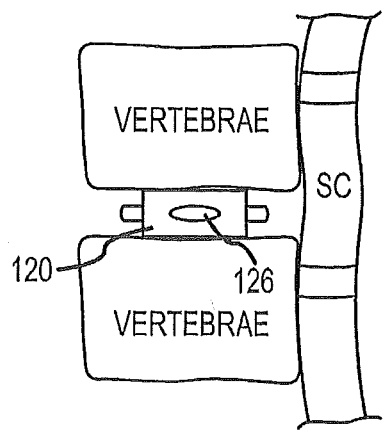
FIG. 20D is a view of the device of FIG. 20A inserted between vertebrae.
Figures 21A, 21B:
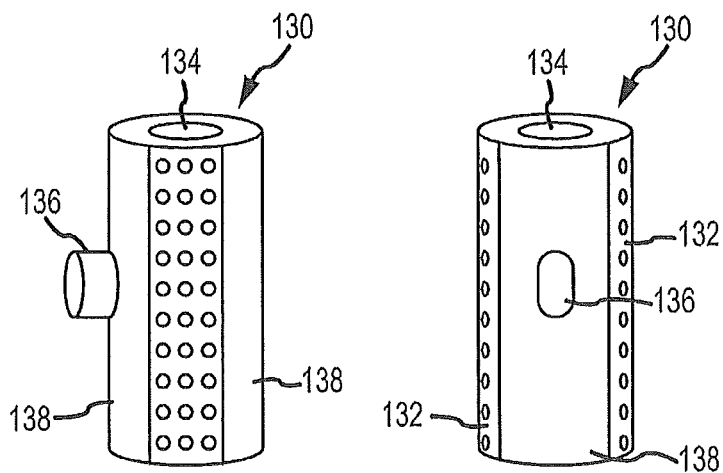
FIG. 21A is a front perspective view of a fusion cage of an embodiment of the device particularly adapted for use in connection with vertebrectomy procedures.
FIG. 21B is a left perspective view of the device of FIG. 21A.
Figures 21C, 21D:
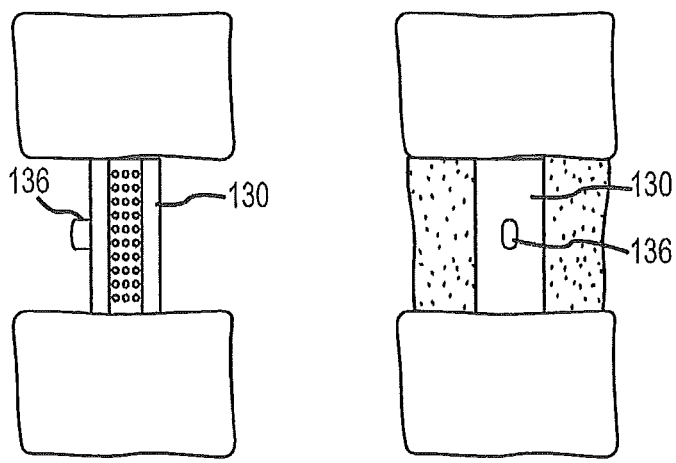
FIG. 21C is a front elevation view of the device of FIG. 21A inserted into a surgical site.
FIG. 21D is a left elevation view of the device of FIG. 21A inserted into a surgical site.

In the embodiment of the device of FIG. 17A-B, the hollow tube 2 engages with a connector conduit 100 which in turn connects with the fusion cage 60 via a break-off collar 90. One or more connectors 102 connect the hollow tube 2 with the connector conduit 100. The hollow tube 2 fits over the connector conduit 100. The one or more connectors 102 fit through the hollow tube 2 and the connector conduit 100. The break-off collar 90 may be severed by any of several means, to include application of torsion and/or rotational force and/or lateral force to break-off collar 90, for example by twisting on the hollow tube 2 and/or the plunger 12. In one embodiment of the connector conduit 100, as shown in FIG. 17B, the connector conduit 100 is of circular cross-section.

Referring to FIGS. 18A-D, sequential elevation views of the square-shaped embodiment of the integrated fusion cage and graft delivery device 1 are provided, depicting sequential elevation views of the integrated fusion cage and graft delivery device 1 with telescoping tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end of the tubular member to allow bone graft material to be provided to the surgical site in other than a purely axial or longitudinal direction.

In an embodiment of the invention particularly suited for ALIF procedures, a fusion cage 110 as shown in FIGS. 19A-D comprises a hollow internal chamber 114 in fluid communication with bone graft discharge portals 112 and a charging portal 116, which comprises a break-off collar in some embodiments such as those depicted in FIGS. 17A-D. The fusion cage 110 has a substantially cylindrical shape, with the discharge portals 112 located opposite each other on the curved lateral portion of the fusion cage 110 and the charging portal 116 located substantially in between the discharge portals 112 on the curved anterior portion of the fusion cage 110. The curved posterior portion of the fusion cage 110 is substantially devoid of portals from the internal chamber 114 to the exterior of the fusion cage 110. The charging portal 116 is adapted to receive a hollow tube such as the hollow tube 2 shown in other embodiments described herein. Bone graft material enters the internal chamber 114 through a hollow tube connected to the charging portal 116, and exits the internal chamber 114 through the discharge portals 112. The discharge portals 112 are positioned so that when the fusion cage 110 is properly positioned in between two vertebrae, bone graft material discharged therethrough fills the space in between the vertebrae on the lateral sides of the spine, but does not discharge into or fill the anterior or posterior space in between the vertebrae. In embodiments of fusion cage 110 comprising a break-off collar, once the fusion cage 110 is properly positioned and the desired amount of bone graft material has been inserted into the chamber 114 and discharged through the discharge portals 112, the break-off collar is severed from the fusion cage 110 (as described with respect to other embodiments herein) and removed from the patient's body.

In embodiments that do not comprise a break-off collar, the charging portal 116 of fusion cage 110 is adapted to removably receive a hollow tube (such as the hollow tube 2 shown in other embodiments described herein). For example, the walls of the charging portal 116 may be threaded so that the hollow tube can be screwed into the charging portal 116.

The fusion cage 110 preferably has a height of from about 8 millimeters to about 14 millimeters, and a diameter of less than about 36 millimeters. The fusion cage 110 is made from polyether ether ketone (PEEK), titanium, a composite material, or any other material suitable for implantation in a human body. The fusion cage 110 comprises, in some embodiments, ramps within internal chamber 114 to guide bone graft material to discharge portals 112.

In an embodiment of the invention particularly suited for D-LIF procedures, a fusion cage 120 as shown in FIGS. 20A-D comprises a hollow internal chamber 124 in fluid communication with bone graft discharge portals 122 and a charging portal 126, which in some embodiments—including the embodiment shown in FIGS. 20A-D—comprises a break-off collar. The fusion cage 120 is substantially shaped as a rectangular prism, with the discharge portals 122 located on opposite sides of the fusion cage 120 and the charging portal 126 located on a lateral face of the fusion cage 120. The opposite lateral face of the fusion cage 120 is devoid of portals from the internal chamber 124 to the exterior of the fusion cage 120. The charging portal 126 is adapted to receive a hollow tube such as the hollow tube 2 shown in other embodiments described herein. Bone graft material enters the chamber 124 through a hollow tube connected to the charging portal 126, and exits the internal chamber 124 through the discharge portals 122. The discharge portals 122 are positioned so that when the fusion cage 120 is properly positioned in between two vertebrae, bone graft material discharged therethrough fills the space in between the vertebrae towards the anterior and posterior of the spine, but does not discharge into or fill the lateral space in between the vertebrae. As with other embodiments described herein, in embodiments that comprise a break-off collar, once the fusion cage 120 is properly positioned and the desired amount of bone graft material has been inserted into the chamber 124 through charging portal 126 and discharged through the discharge portals 122, the break-off collar is severed from the fusion cage 120 (as described with respect to other embodiments herein) and removed from the patient's body.

In embodiments that do not comprise a break-off collar, the charging portal 126 is adapted to removably receive a hollow tube (such as the hollow tube 2 shown in other embodiments described herein). For example, the internal walls of charging portal 126 may be threaded so that the hollow tube can be screwed into the charging portal 126.

The fusion cage 120 preferably has a height of from about 8 millimeters to about 14 millimeters, and a length of from about 22 millimeters to about 36 millimeters. The fusion cage 120 is made from polyether ether ketone (PEEK), titanium, a composite material, or any other material suitable for implantation in a human body. The fusion cage 120 comprises, in some embodiments, ramps within internal chamber 124 to guide bone graft material to discharge portals 122.

Referring now to FIGS. 21A-D, in embodiments of the invention particularly suited for use in connection with a vertebrectomy, a fusion cage 130 comprises a substantially cylindrical wall surrounding an internal chamber 134. Thus, the fusion cage 130 has a substantially cylindrical shape. Internal chamber 134 is open at the top and the bottom of fusion cage 130, and lateral portions 132 of the cylindrical wall of the fusion cage 130 are porous to bone graft material (i.e. bone graft slurry). Anterior and posterior portions 138 of the cylindrical wall of fusion cage 130 in between porous portions 132 are impervious to bone graft material. A charging portal 136—which in some embodiments, including the embodiment shown in FIGS. 21A-D, comprises a break-off collar—is positioned on an impervious portion 138 of fusion cage 130. The charging portal 136 is adapted to receive a hollow tube such as the hollow tube 2 shown in other embodiments described herein. Bone graft material enters the chamber 134 through a hollow tube connected to the charging portal 136, and exits the chamber 134 through porous wall portions 132. The porous wall portions 132 are positioned so that when the fusion cage 130 is properly positioned in between two vertebrae, bone graft material discharged therethrough fills the space in between the vertebrae on either side of the spine, but the impervious wall portions 138 prevent bone graft material from discharging into the anterior or posterior space in between the vertebrae, thus preventing bone graft material from pushing against the spinal cord. In embodiments of fusion cage 130 comprising a break-off collar, once the fusion cage 130 is properly positioned and the desired amount of bone graft material has been inserted into the chamber 134 through charging portal 136 and discharged through the porous wall portions 132, the break-off collar 136 is severed from the fusion cage 130 (as described with respect to other embodiments herein) and removed from the patient's body.

In embodiments that do not comprise a break-off collar, the charging portal 136 is adapted to removably receive a hollow tube (such as the hollow tube 2 shown in other embodiments described herein). For example, the internal walls of the charging portal 136 may be threaded so that the hollow tube can be screwed into the charging portal 136.

The fusion cage 130 preferably has a height equal to or greater than the vertebra or vertebrae it is intended to replace, and a diameter of less than about 36 millimeters. The fusion cage 130 is made of polyether ether ketone, titanium, a composite material, or any other material suitable for implantation in a human body. In some embodiments, ramps in the internal chamber 134 guide the bone graft material to the porous lateral faces 132.

Figure 22:
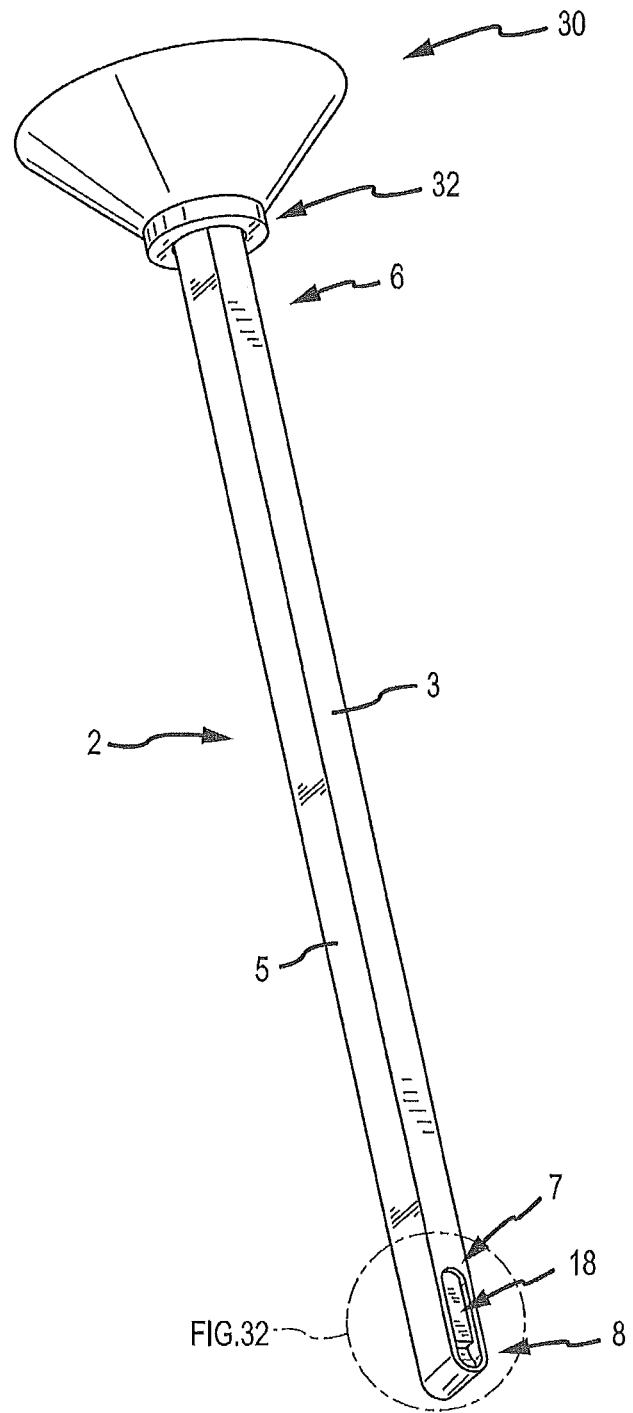
FIG. 22 is a front perspective view of another embodiment of the device for delivering bone graft.
Figure 27:
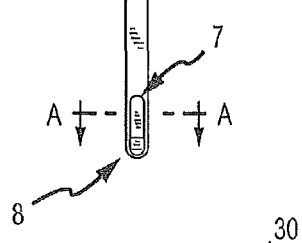
FIG. 27 is a bottom plan view of the device shown in FIG. 22.
Figure 28:
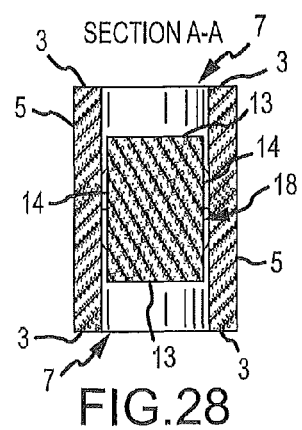
FIG. 28 is a cross-sectional view of section A-A of FIG. 25.

Referring now to FIGS. 22-33, another embodiment of the device for delivering bone graft is provided. In regard to FIGS. 22-28, integrated fusion cage and graft delivery device 1 is shown. FIG. 22 is a perspective view of the device 1, FIG. 23 a perspective exploded view, FIG. 24 a top plan view, FIG. 25 a front elevation view, FIG. 26 a right elevation view, FIG. 27 is a bottom plan view, and FIG. 28 is a cross-sectional view of section A-A of FIG. 25.

Device 1 is comprised of a hollow tubular member or hollow tube 2, a plunger 12 which fits within the hollow tube 2, and a funnel 30. The funnel 30 engages the upper or distal or first end 6 of the hollow tube, and comprises a sleeve 32 and opening 34. Medical material, such as bone graft material, is inserted into opening 34 of funnel 30, which in turn enters hollow tube 2. Hollow tube 2 comprises hollow tube first exterior surface 3, hollow tube second exterior surface 5, first end 6, second end 8, and hollow tube first distal opening 7. Hollow tube 2 is generally of symmetrical shape such that first exterior surface 3 comprises two such surfaces opposite or at 180 degrees from one another, and second exterior surface 5 comprises two such surfaces opposite or at 180 degrees from one another. Also, hollow tube first distal opening 7 is positioned on each of two opposite sides of hollow tube 2 at second end 8, each opening from hollow tube first exterior surface 3.

Figure 23:
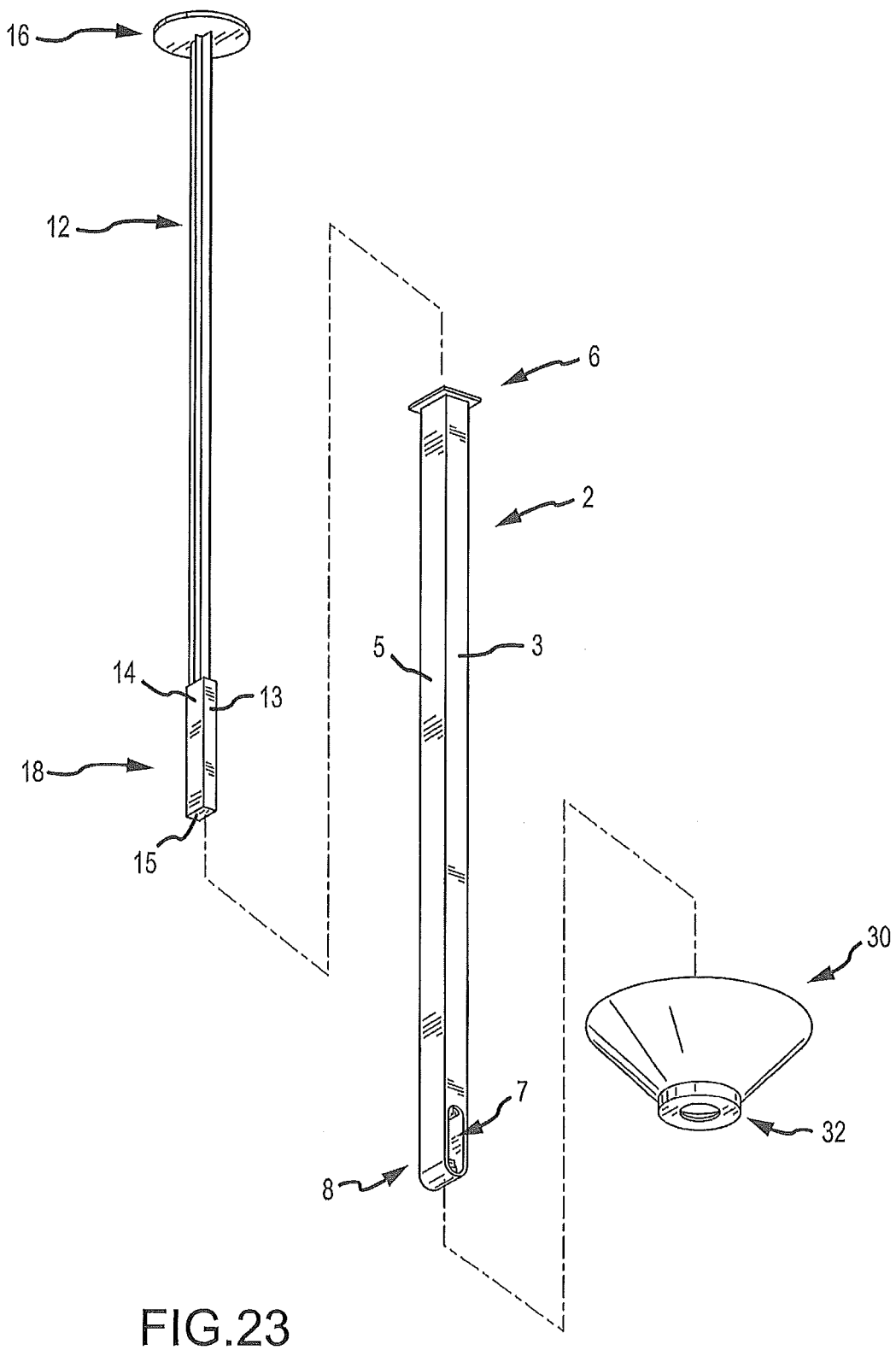
FIG. 23 is a front perspective exploded view of the device shown in FIG. 22.
Figure 24:
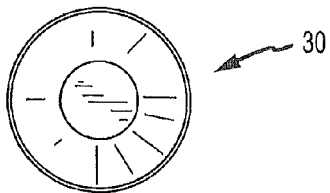
FIG. 24 is a top plan view of the device shown in FIG. 22.
Figure 25:
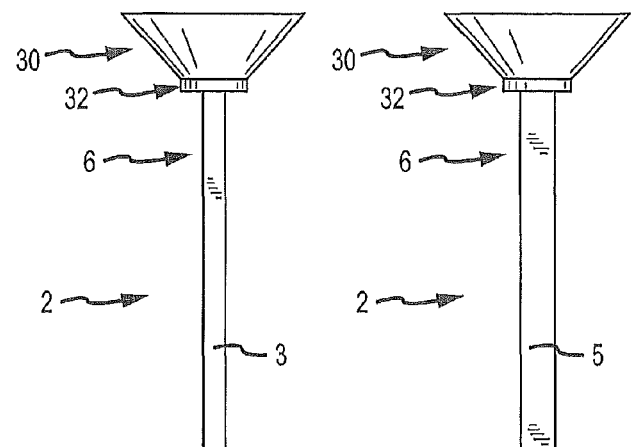
FIG. 25 is a front elevation view of the device shown in FIG. 22.
Figure 26:
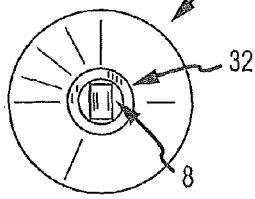
FIG. 26 is a right elevation view of the device shown in FIG. 22.

Funnel 30 is configured with sleeve 32 such that funnel 30 may be positioned at second end 8 of hollow tube 2 such that hollow tube may fit through funnel 30, enabling funnel 30 to move along hollow tube 2 from second end 8 of hollow tube 2 to first end 6 of hollow tube 2 until funnel 30 engages first end 6 of hollow tube, such as at protrusion or shelf depicted in FIG. 23.

Plunger 12 comprises handle 16 at upper or proximal end of plunger 12, plunger distal or second end 18. Plunger second end 18 comprises distal first surface 13, distal second surface 14 and distal third (or bottom) surface 15. Plunger second end 18 is generally of symmetrical shape such that distal first surface 13 comprises two such surfaces opposite or at 180 degrees from one another, and distal third surface 15 comprises two such surfaces opposite or at 180 degrees from one another. Plunger 12 is configured such that second end 18 forms a congruent or conformal engagement with the interior of the hollow tube 2. Stated another way, the plunger second end 18 fits within the hollow tube 2 so as to slide within the hollow tube with minimal to no effective spacing between the exterior surface of the plunger second end 18 and the interior of the hollow tube 2, thereby forcing through bone graft material positioned in the hollow tube 2 through the hollow tube when the plunger 12 (and thus its second end 18) is axially moved from hollow tube first end 6 to hollow tube second end 8.

Figures 29, 30, 31:
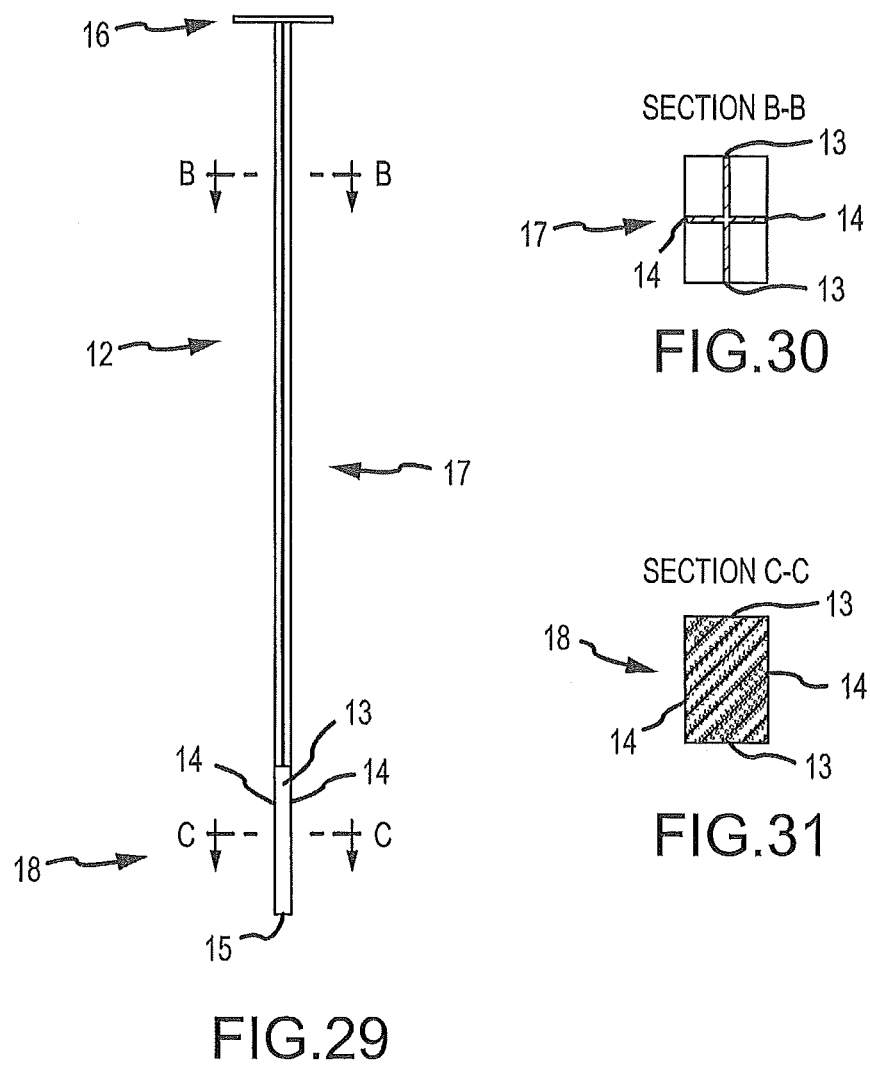
FIG. 29 is a front elevation view of the plunger element of the device shown in FIG. 22.
FIG. 30 is a cross-sectional view of section B-B of FIG. 29.
FIG. 31 is a cross-sectional of section C-C of FIG. 29.

In regard to FIGS. 29-31, further features of the plunger 12 are described. FIG. 29 is a front elevation view of the plunger element of the device shown in FIG. 22, FIG. 30 is a cross-sectional view of section B-B of FIG. 29, and FIG. 31 is a cross-sectional of section C-C of FIG. 29. Plunger 12 comprises handle 16 at upper or proximal end of plunger 12, plunger distal or second end 18. Plunger second end 18 comprises distal first surface 13, distal second surface 14 and distal third (or bottom) surface 15. Plunger medial portion 17 forms a cross configuration, as depicted in FIG. 30, such that distal first surfaces 13 are of reduced width relative to width at second end 18. Similarly, plunger distal second surfaces 14, at plunger medial portion 17, are of reduced width relative to width at second end 18. At distal end 18 of plunger 12, plunger cross-section is a rectangle, as depicted in FIG. 31.

Figure 32:
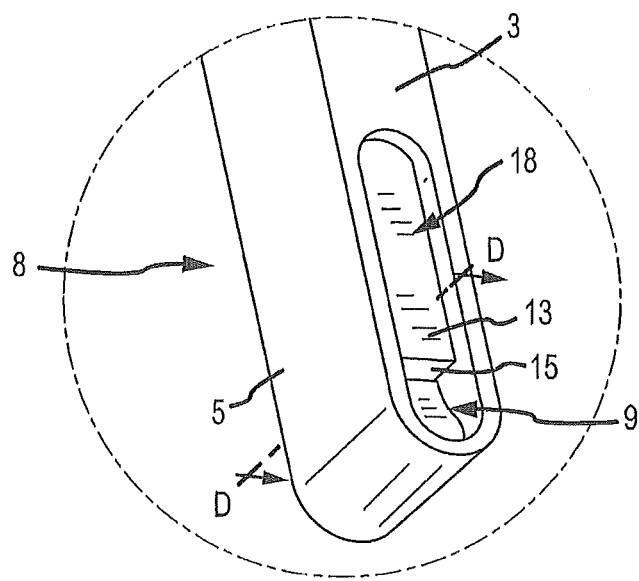
FIG. 32 is a detailed front perspective view of a portion of the device shown in FIG. 22.
Figure 33:
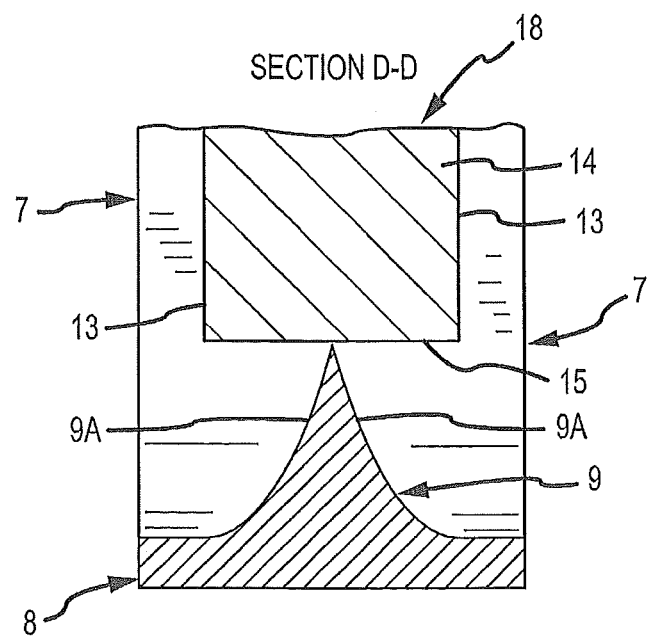
FIG. 33 is a cross-sectional view of section D-D of FIG. 32.

In regard to FIGS. 32 and 33, additional detail of the distal portion of device 1 are provided. FIG. 32 is a detailed view of a portion of the device 1 shown in FIG. 22 and FIG. 33 is a cross-sectional view of section D-D of FIG. 32. Each of FIGS. 32 and 33 depict the device 1 when the plunger 12 is fully inserted into the hollow tube 2, and the plunger distal third surface 15 has engaged and is in contact with the hollow tube distal interior ramp 9. Hollow tube distal interior ramp 9 comprises hollow tube distal interior ramp surfaces 9A, symmetrically positioned about the middle of the hollow tube second end 8. Hollow tube distal interior ramp surfaces 9A are of curvilinear shape forming a terminus, and urge bone graft material, when disposed within the hollow tube 2, to substantially exit the pair of first distal openings 7 of the device 1.

Referring now to FIGS. 36-39 another embodiment of an integrated fusion cage and graft delivery device 1 is provided. With reference to FIGS. 36-39, the integrated fusion cage and graft delivery device 1 comprises plunger 12, hollow tube 2, fusion cage 60 and ejection tool 140. The fusion cage 60 comprises fusion cage second or distal end 64 with tapered end feature and fusion cage first or proximal end 62 comprising fusion cage collar 92, fusion cage collar face 93 and fusion cage collar cavity 94. Hollow tube 2 comprises hollow tube second end 8 which engages fusion cage collar 92 by fitting over fusion cage collar 92 in a press or interference fit. Plunger 12 fits within hollow tube 12, and further may optionally fit within fusion cage collar cavity 94 so as to enter into interior of fusion cage 60 as previously described above.

Ejection tool 140 comprises ejection tool second or distal end 152 and ejection tool first or proximal end 142. Ejection tool second end 152 engages fusion cage collar face 93 to apply force or push fusion cage 60 from engagement with hollow tube 2. Ejection tool second end 152 is configured such that it may not travel past or into the fusion cage. When sufficient axial force is applied to the ejection tool 140 in the direction of the fusion cage 60, the interference fit that secures the fusion cage 60 (at fusion cage collar 92) to hollow tube 2 (at second end 8 of hollow tube) is overcome and the fusion cage 60 is released or disengaged from the hollow tube 2. Ejection tool 140 further comprises an ejection tool L-cut 151 that engages knobs 6A of hollow tube 2. In one embodiment, knobs 6A of hollow tube 2 are configured to additionally or alternatively engage L-cuts of the funnel 30 at funnel sleeve 32 (See FIG. 23). Plunger 16 further comprises handle 16 and plunger stop 16A which engages upper portion of hollow tube 2. Plunger stop 16A may be configured to prevent plunger distal most portion from entering fusion cage collar cavity 94 and therefore further prevent entry into interior of fusion cage 60.

Fusion cage 60 further comprises fusion cage internal ramps 72 as described above. The fusion cage internal ramps 72 may be symmetrical about a centerline of the device 1, and may be linear or sloped inwardly. In one embodiment, plunger stop 16A may be configured to prevent plunger distal most portion from striking or contacting fusion cage internal ramps 72 but otherwise allowing entry into fusion cage collar cavity 94 and therefore also allow entry into interior of fusion cage 60.

Fusion cage 60 further comprises fusion cage first opening or port pair 65 and fusion cage second opening or port pair 67. Fusion cage first opening pair 65 are symmetric about a vertical plane intersecting a centerline of the fusion cage 60, and are located such that at least a portion of the openings are adjacent the tip of the fusion cage internal ramps 72. The fusion cage first opening pair 65 are of an oblong racetrack shape, but in other embodiments may be oval, circular and rectangular. The fusion cage second opening pair 67 are of an oval shape, but in other embodiments may be oblong racetrack, circular and rectangular. The fusion cage may have rounded or no square edges, and may have a non-smooth exterior surface or any or all portions. That is, the fusion cage 60 may have ridges, bumps, contours, sawtooth profile edges along or on top of any or all exterior surfaces, such as surfaces adjacent the fusion cage second opening pair 67 and/or fusion cage first opening pair 65.

Figure 40:
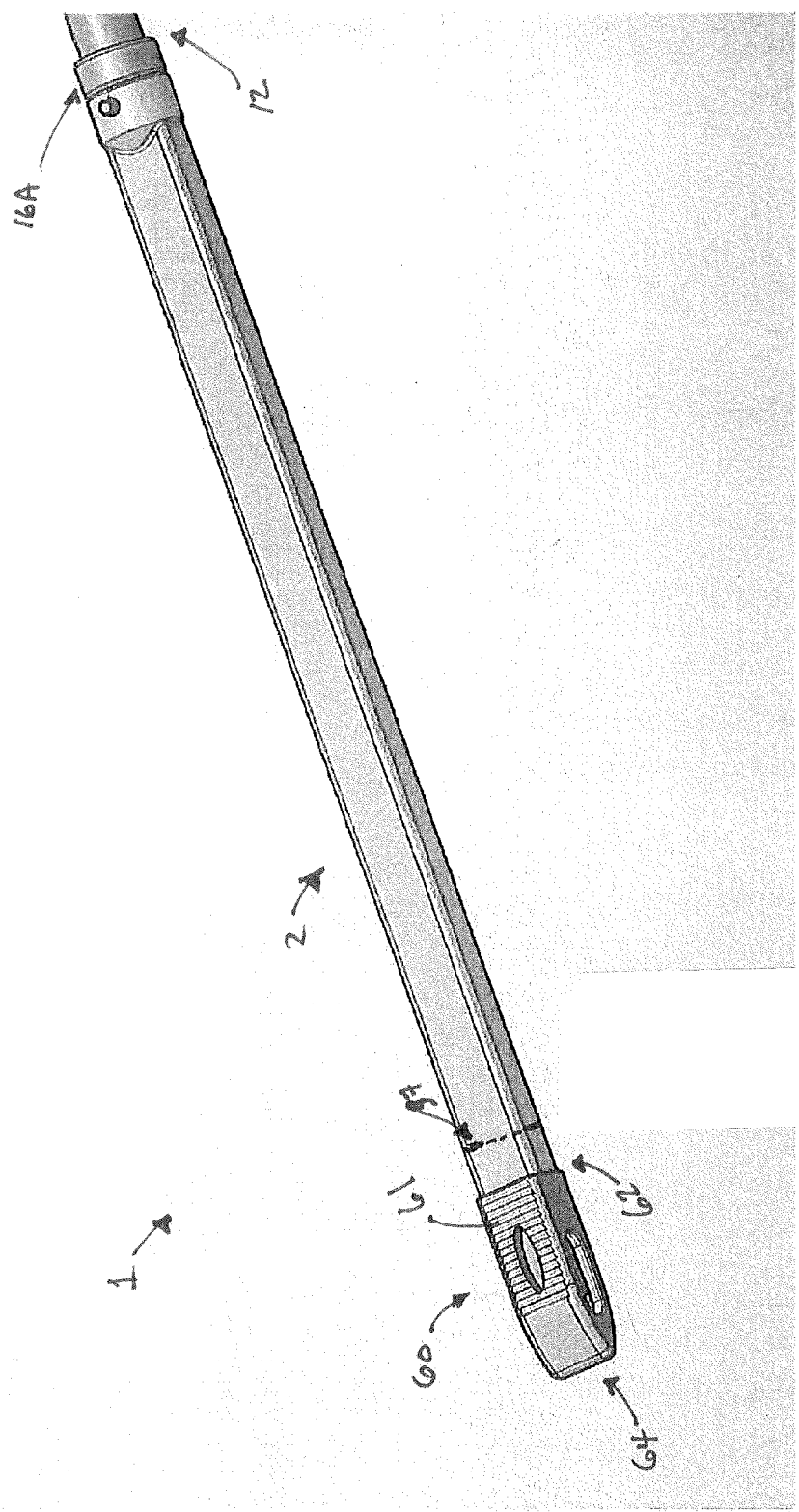
FIG. 40 is a front perspective view of an integrated fusion cage and graft delivery device according to yet another embodiment.
Figure 41:
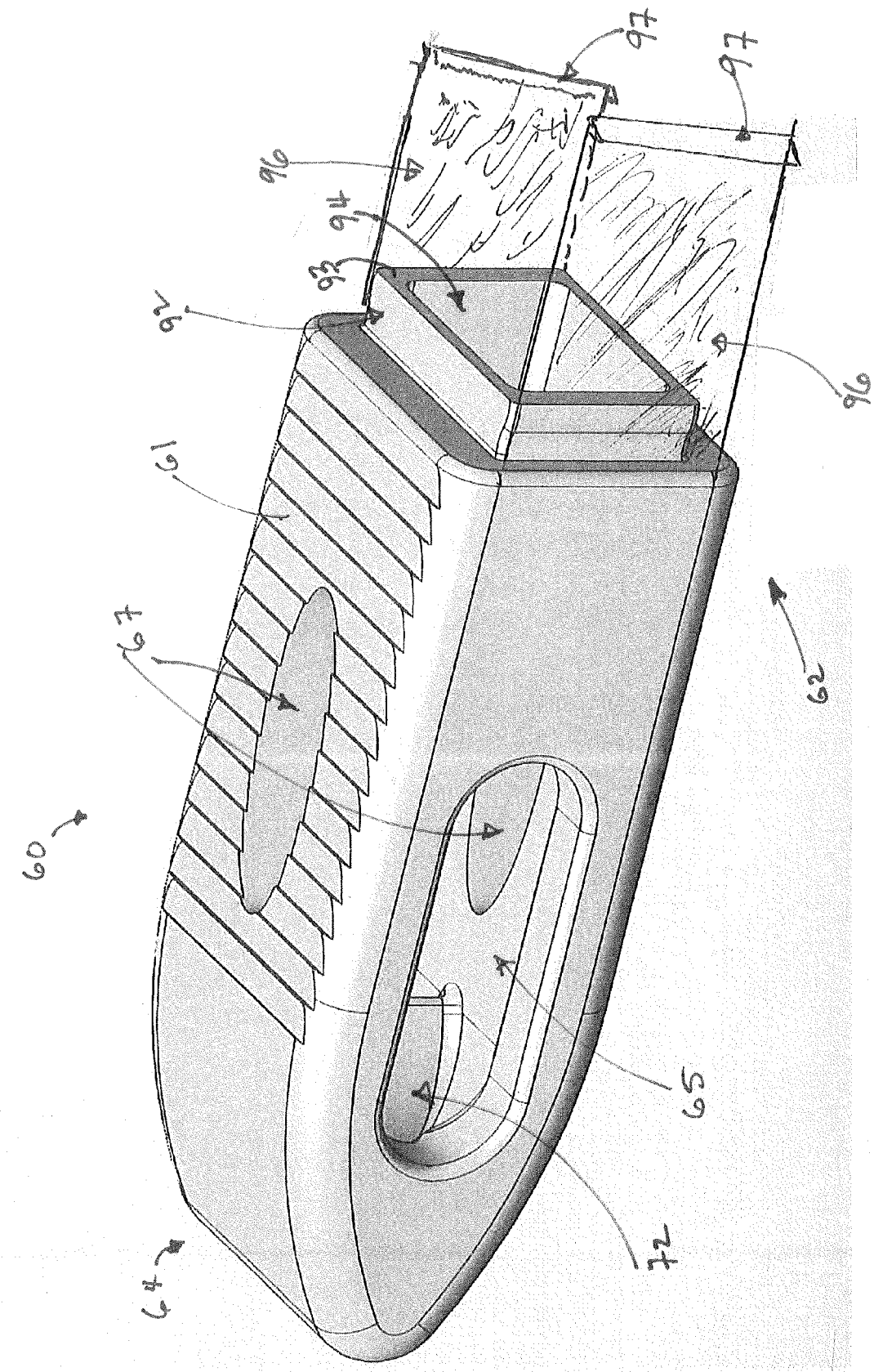
FIG. 41 is a closed-up front perspective view of the device of FIG. 40.

Referring now to FIGS. 40-41, another embodiment of an integrated fusion cage and graft delivery device 1 is provided. FIG. 40 is a front perspective view of an integrated fusion cage and graft delivery device 1, and FIG. 41 is a closed-up front perspective view of a portion of the device of FIG. 40. The embodiment of FIGS. 40-41 comprises a pair of fusion cage tab extensions 96, each of which comprises a fusion cage tab extension latch 97. Integrated fusion cage and graft delivery device 1 comprises plunger 12, hollow tube 2 and fusion cage 60. FIG. 40 depicts the integrated fusion cage and graft delivery device 1 with plunger 12 fully inserted into hollow tube 2 such that plunger stop 16A engages upper portion of hollow tube 2. The fusion cage 60 comprises fusion cage second or distal end 64 with tapered end feature and fusion cage first or proximal end 62 comprising fusion cage collar 92, fusion cage collar face 93 and fusion cage collar cavity 94.

Fusion cage 60 further comprises fusion cage internal ramps 72 as described above. The fusion cage internal ramps 72 may be symmetrical about a centerline of the device 1, and may be linear or sloped inwardly. Fusion cage 60 further comprises fusion cage first opening or port pair 65 and fusion cage second opening or port pair 67. Fusion cage first opening pair 65 are symmetric about a vertical plane intersecting a centerline of the fusion cage 60, and are located such that at least a portion of the openings are adjacent the tip of the fusion cage internal ramps 72. The fusion cage first opening pair 65 are of an oblong racetrack shape, but in other embodiments may be oval, circular and rectangular. The fusion cage second opening pair 67 are of an oval shape, but in other embodiments may be oblong racetrack, circular and rectangular. The fusion cage may have rounded or no square edges. Fusion cage 60 has fusion cage surface texture 61, depicted as a series of lateral sawtooth-like ridges.

Fusion cage tab extensions 96, each of which comprises a fusion cage tab extension latch 97, function, among other things, to increase stability of the interface or connection between the distal end of the hollow tube 2 and the fusion cage 60. The fusion cage tab extension latches 97 may be configured to engage corresponding grooves on the interior surface of the hollow tube 2. The fusion cage tab extensions 96 fit inside the end of the hollow tube and, in one embodiment, provide a force directed outwards to or against the interior of the hollow tube. The vertical height and longitudinal (axial) length of the fusion cage tab extensions 96 provide more secure fit between the hollow tube 2 and the fusion cage 60 by restricting rotational movement, for example, of the hollow tube 2 with respect to the fusion cage 60. After bone graft material is provided to the fusion cage 60 by way of the plunger 12 (as described above), the fusion cage tab extensions 96 may be broken-off by application of a tool, such as the ejection tool 140, engaged with the fusion cage tab extension latches 97 so as to fatigue or otherwise severe the fusion cage tab extensions 96.

Figure 42:
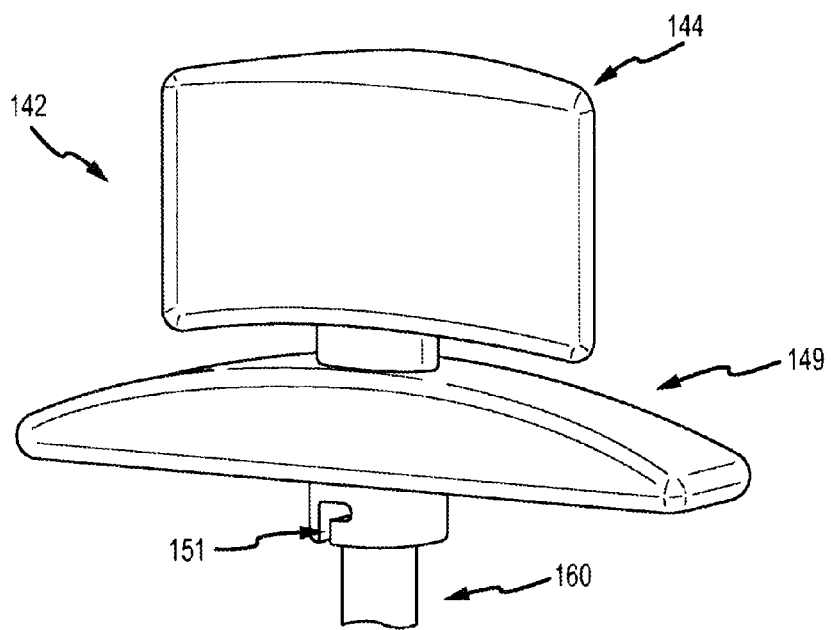
FIG. 42 is a close-up front perspective view of the ejection tool element first end.
Figure 43:
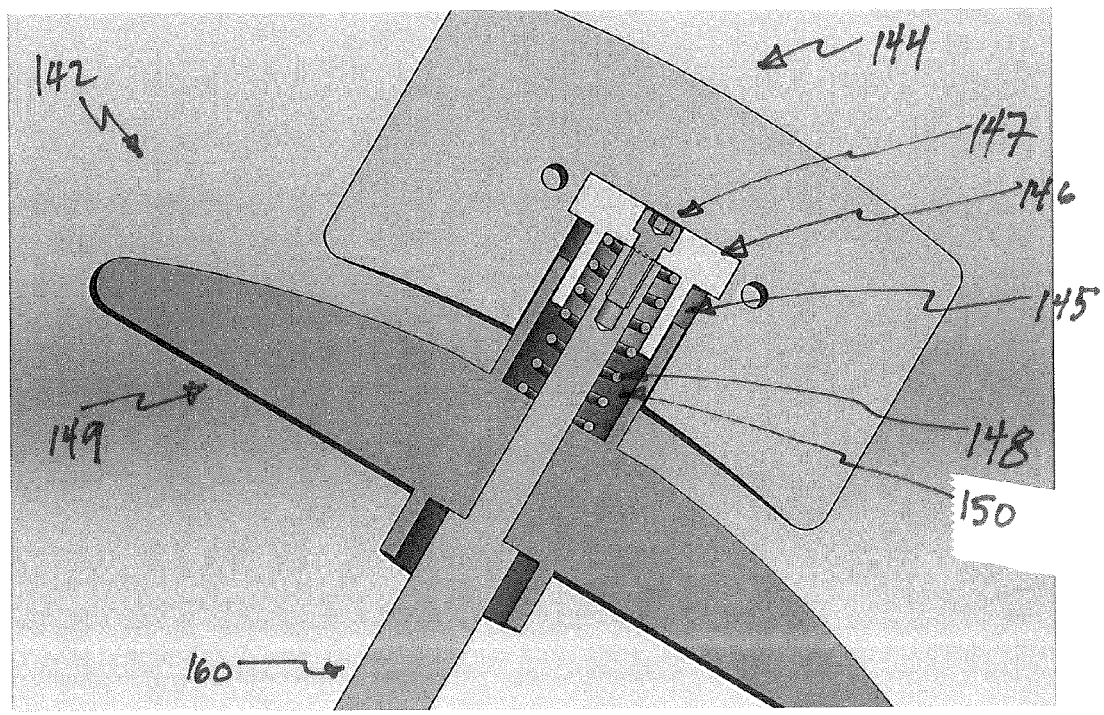
FIG. 43 is a cut-away cross-sectional view of the element of FIG. 42.

Referring now to FIGS. 42-43, another embodiment of the ejection tool 140 of an integrated fusion cage and graft delivery device 1 is provided. FIG. 42 is a close-up front perspective view of the ejection tool first end 142, and FIG. 43 is a cut-away cross-sectional view of FIG. 42. Ejection tool 140 comprises ejection tool cover 144 which engages ejection tool wings 149. Ejection tool 140 engages with hollow tube 2 at hollow tube knobs 6A via ejection tool L-cuts 151. Ejection tool cover 144 comprises cylindrically-shaped ejection tool cover cavity 145 which fits over cylindrically-shaped ejection tool wings cavity 150 and over spring cover 146. Spring cover is secured to ejection tool cover 144 by spring cover attachment 147, which may be a pin, a screw or other means known in the art, and further fits around at least a portion of coiled spring 148. When ejection tool cover 144 is pushed downward toward fusion cage 60, the spring 148 compresses and imparts a force in the opposite direction, thereby returning the ejection tool cover 144 to its original (retracted) position. In use, after securing the ejection tool first end 142 to hollow tube 2 as described above, the user (e.g. surgeon) squeezes the ejection tool cover 144 against the ejection tool wings 149, thereby advancing the ejection tool rod 160 downwards inside the hollow tube so as to engage the fusion cage 60 at the fusion cage collar face 93 and release or disengage the fusion cage 60 from the hollow tube 2. The enjection tool 140 and hollow tube 2 may then be removed from the surgical site (e.g. spinal disk space) as one unit, leaving the fusion cage in the surgical site.

Figure 44:
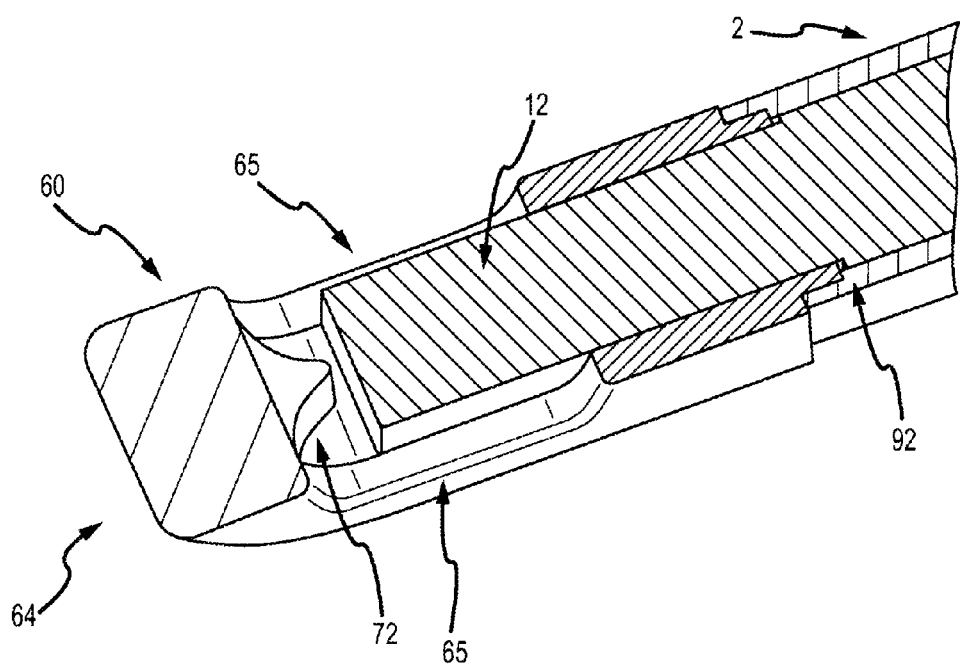
FIG. 44 is a close-up cut-away cross-sectional view of one embodiment of the integrated fusion cage and graft delivery device.

FIG. 44 is a close-up cut-away cross-sectional view of one embodiment of the integrated fusion cage and graft delivery device 1. FIG. 44 depicts a configuration of the integrated fusion cage and graft delivery device 1 wherein the plunger 12 is configured to traverse the length og the hollow tube 2, past the fusion cage collar 92 and into the fusion cage 60, stopping just prior to engaging the tip of the fusion cage internal ramps 72. Fusion cage 60 is depicted with fusion cage first opening pair 65 and fusion cage second end 64.

FIGS. 45-48 are scaled drawings of, respectively, the fusion cage 60, the hollow tube 2, the plunger 12 and the ejection tool 140 of yet another embodiment of the integrated fusion cage and graft delivery device 1, and operate in coordination with one another.

FIGS. 45A-G provide scaled views of one embodiment of the fusion cage element of yet another embodiment of the integrated fusion cage and graft delivery device configured to operate with the hollow tube of FIGS. 46A-H, plunger of FIGS. 47A-D and ejection tool of FIGS. 48A-E. Fusion cage 60 comprises fusion cage second or distal end 64 with tapered end feature and fusion cage first or proximal end 62 comprising fusion cage collar 92, fusion cage collar face 93 and fusion cage collar cavity 94. Fusion cage 60 further comprises fusion cage first opening or port pair 65, fusion cage second opening or port pair 67, fusion cage surface texture 61 and fusion cage internal ramps 72.

FIGS. 46A-H provide scaled views of one embodiment of the hollow tube (aka snap on cannula) of the integrated fusion cage and graft delivery device configured to operate with the fusion cage element of FIGS. 45A-G, plunger of FIGS. 47A-D and ejection tool of FIGS. 48A-E. Hollow tube 2 comprises first end 6 with knobs 6A and second end 8 comprising hollow tube cage clamp 8A and hollow tube cage clamp radial surface 8B. Hollow tube cage clamp radial surface 8B is configured to engage fusion cage collar 92, for example by an interference or friction fit (i.e. to "snap-on"). Other means of connection comprise those known to those skilled in the art, such as a threaded-screw engagement and a tongue and groove engagement.

FIGS. 47A-D provide scaled views of one embodiment of the plunger (aka snap on plunger) of the integrated fusion cage and graft delivery device configured to operate with the fusion cage element of FIGS. 45A-G, hollow tube of FIGS. 46A-H, and ejection tool of FIGS. 48A-E. Plunger 12 comprises handle 16, plunger stop 16A, plunger medial portion 17 and second end 18. Second end 18 may be configured to pass into and/or through fusion cage collar cavity 94.

FIGS. 48A-E provide scaled views of one embodiment of the ejection tool (aka cage insertion tool) of the integrated fusion cage and graft delivery device configured to operate with the fusion cage element of FIGS. 45A-G, hollow tube of FIGS. 46A-H and plunger of FIGS. 47A-D. Ejection tool 140 comprises ejection tool second or distal end 152, ejection tool first or proximal end 142 and ejection tool stop 143. Ejection tool second end 152 engages fusion cage collar face 93 to apply force or push fusion cage 60 from engagement with hollow tube 2. Ejection tool second end 152 is configured such that it may not travel past or into the fusion cage.

A method of use of the integrated fusion cage and graft delivery device 1 as depicted in any of the afore-mentioned embodiments of FIGS. 37-48 would be performed as follows. The fusion cage 60 is attached to the hollow tube 2 by way of the above-discussed interference fit at fusion cage collar 92 and interior surface of distal end of hollow tube 2. Funnel 30 is then attached to upper portion of hollow tube at first or upper or proximal end of hollow tube 2 via knobs 6A. Bone graft or other suitable substance as known to one skilled in the art is inserted at upper or first end 6 of hollow tube 2. Plunger 12 is then inserted into hollow tube 2 at upper or proximal end of hollow tube and pushed or advanced axially down interior of hollow tube, thereby urging or pushing or advancing the bone graft material down the hollow tube 2 toward fusion cage 60. Bone graft then proceeds into the fusion cage 60 whereby it at least substantially fills fusion cage 60 interior and further engages fusion cage internal ramps 72 and emits bone graft material through fusion cage first opening pair 65 and fusion cage second opening pair 67 and thus enters surgical area (e.g. a spinal surgical area). Upon sufficient user (i.e. surgeon) selectable injection of bone graft material into surgical site and fusion cage 60, the plunger 12 is refracted and removed from the hollow tube 2 by opposite axial movement, i.e. by moving the plunger 12 away from the fusion cage 60. The funnel 30 may then be optionally removed. Next, the ejection tool 140 is inserted into hollow tube 2 at upper or proximal end Ejection tool 140 is advanced until ejection tool second end 152 engages fusion cage collar face 93, whereupon downward force is applied to push fusion cage 60 from engagement with hollow tube 2. As discussed, ejection tool second end 152 is configured such that it may not travel past or into the fusion cage. When sufficient axial force is applied to the ejection tool 140 in the direction of the fusion cage 60, the interference fit that secures the fusion cage 60 (at fusion cage collar 92) to hollow tube 2 (at second end 8 of hollow tube) is overcome and the fusion cage 60 is released or disengaged from the hollow tube 2. The engagement tool 140, and the hollow tube 2 in which it is inserted, are then removed from the surgical site, leaving a fusion cage at least substantially filled with bone graft and a surgical site also at least substantially filled with bone graft.

In one embodiment, all or a portion of fusion cage collar 92 is of a material different than the remainder of the fusion cage 60, e.g. comprising a metal alloy. In one embodiment, a portion of the distal end of the hollow tube 2 is of a material different than the remainder of the hollow tube 2, e.g. comprising a metal alloy. In one embodiment, a portion of the distal end of the ejection tool is comprised of a metal alloy.

In one embodiment of the device, the tip of the hollow tube and/or fusion cage may separate under a threshold pressure as applied axially from the inside of the hollow tube or fusion cage respectively. Such a user-selected threshold would allow bone graft material to enter the surgical site if bone graft material becomes clogged in the hollow tube and/or fusion cage.

In one embodiment, one or more alignment markers are placed on the funnel, e.g. lines at 0 degree and 180 degree. In one embodiment, one or more clamps are applied to the hollow tube for additional support and/or stability. The clamps may be, e.g. scissor-type clamps. In one embodiment, all or a portion of the plunger, hollow tube, fusion cage and ejection tool comprise a thermoplastic polycarbonate such as Lexan™. In one embodiment, the fusion cage comprises a different material than one or more of the hollow tube, plunger and ejection device. In one embodiment, the plunger comprises an elastic portion and elastic seal which functions, among other things, to restrict wiggle of the plunger when moving through the hollow tube. In one embodiment, one or more portions of the device are manufactured via sonic welding, and/or comprise a sonic weld. For example, the tip of the hollow tube and/or fusion cage may be sonic welded or comprise a sonic weld.

In one embodiment of the device, the width of the hollow tube second exterior surface 5 is between 10 and 14 mm. In a preferred embodiment, the width of the hollow tube second exterior surface 5 is between 11 and 13 mm. In a most preferred embodiment, the width of the hollow tube second exterior surface 5 is between 11.5 mm and 12.5 mm. In a preferred embodiment, the width of the hollow tube second exterior surface 5 is 12 mm.

In one embodiment of the device, the width of the hollow tube first exterior surface 3 is between 6 and 10 mm. In a preferred embodiment, the width of the hollow tube first exterior surface 3 is between 7 and 9 mm. In a most preferred embodiment, the width of the hollow tube first exterior surface 3 is between 7.5 mm and 8.5 mm. In a preferred embodiment, the width of the hollow tube first exterior surface 3 is 8 mm.

In one embodiment of the device, the ratio of the width of the hollow tube second exterior surface 5 and the width of the hollow tube first exterior surface 3 is between 1.7 and 1.3. In a preferred embodiment, the ratio of the width of the hollow tube second exterior surface 5 and the width of the hollow tube first exterior surface 3 is between 1.6 and 1.4. In a most preferred embodiment, the ratio of the width of the hollow tube second exterior surface 5 and the width of the hollow tube first exterior surface 3 is between 1.55 and 1.45. In one embodiment, the ratio of the width of the hollow tube second exterior surface 5 and the width of the hollow tube first exterior surface 3 is 1.5.

In one embodiment of the device, the width of the interior of the hollow tube major axis (located adjacent the second exterior surface 5) is between 9 and 13 mm. In a preferred embodiment, the width of the interior of the hollow tube major axis is between 10 and 12 mm. In a most preferred embodiment, the width of the interior of the hollow tube major axis is between 10.5 mm and 11.5 mm. In a preferred embodiment, the width of the interior of the hollow tube major axis is 11 mm.

In one embodiment of the device, the width of the interior of the hollow tube minor axis (located adjacent the first exterior surface 3) is between 5 and 9 mm. In a preferred embodiment, the width of the interior of the hollow tube minor axis is between 6 and 8 mm. In a most preferred embodiment, the width of the interior of the hollow tube minor axis is between 6.5 mm and 7.5 mm. In a preferred embodiment, the width of the interior of the hollow tube minor axis is 7 mm.

In one embodiment of the device, the ratio of the width of the interior of the hollow tube major axis and the width of the interior of the hollow tube minor axis is between 1.7 and 1.3. In a preferred embodiment, the ratio of the width of the interior of the hollow tube major axis and the width of the interior of the hollow tube minor axis is between 1.6 and 1.4. In a most preferred embodiment, the ratio of the width of the interior of the hollow tube major axis and the width of the interior of the hollow tube minor axis is between 1.55 and 1.45. In one embodiment, the ratio of the width of the interior of the hollow tube major axis and the width of the interior of the hollow tube minor axis is 1.5.

It should be noted that the rectangular configuration of the hollow tube affords several advantages over conventional circular configuration. For example, for a surgical area with smallest dimension set at a width of 8 mm with thickness dimension 0.5 mm, a conventional circular device (with resulting interior diameter of 7 mm or a radius of 3.5 mm) would realize a surface area of 38.48 $mm^2$. Applicants' device would carry interior dimension of 7 mm by 11 mm for a surface area of 77 mm, an increased surface area factor of 2.0, thereby resulting in more bone graft material delivery, because, among other things, a given volume of bone graft encounters less surface area of the interior of a particular device which results in, among other things, reduced chance of jamming of bone graft material within the device.

In one embodiment, a one or more edges of the device are rounded. For example, the exterior edges of the hollow tube are rounded, and/or the interior edges of the hollow tube are rounded (in which case the edges of the plunger, at least at the plunger distal end, are identically rounded to ensure a congruous or conformal fit between the edges of the plunger and the interior of the hollow tube so as to, among other things, urge the majority of bone graft material to move through the hollow tube).

In one embodiment, the handle 16 of plunger is a planar disk shape, as depicted in FIG. 23. In another embodiment, handle 16 is not planar. For example, handle 16 is angled so as to conform to interior of funnel 30 when the plunger 12 is fully inserted into hollow tube 2.

In one embodiment, the hollow tube distal interior ramp surfaces 9A are linear shape, that is, forming a triangle in cross-section. In another configuration, the hollow tube distal interior ramp surfaces 9A are of any shape that urges egress of bone graft material contained in the hollow tube to exit the interior of the hollow tube through the pair of first distal openings 7 of the device 1.

A bone graft tamping device may also be provided, which is adapted to be telescopically inserted into the hollow tube after the plunger is removed from the hollow tube. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

The hollow tube may also be fitted with a passageway wherein a surgical tube or other device may be inserted, such as to deliver a liquid to the surgical area or to extract liquid from the surgical area. In such an embodiment, the plunger is adapted in cross-section to conform to the hollow tube's cross-section.

In another embodiment of the present invention, a kit of surgical instruments comprises a plurality of differently sized and/or shaped hollow tubes and a plurality of differently sized and/or shaped plungers. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectably delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

The kit of surgical instruments may comprise a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly may be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the integrated fusion cage and graft delivery device may either come with a pre-filled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger and hollow tube cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

According to the embodiment described in the preceding paragraph, the present invention may be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area and permits lateral or nearly lateral (n relation to the longitudinal axis of the hollow tube and plunger assembly) introduction of bone graft to the graft receiving area. This method prevents loss of bone graft due to improper or limited orientation of the integrated fusion cage and graft delivery device, and further allows a user to achieve insertion of a desired quantity of bone graft by way of the contoured plunger and hollow tube configuration described according to preferred embodiments herein.

The method of the present invention may also be carried out by providing a hollow tube having a first end and a second end, constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger in a generally downward direction through the hollow tube (i.e., in a direction from the first end to the second end). According to this embodiment, a graft retaining structure may also be provided for use in connection with the contoured edge of the plunger, such that the graft retaining structure is positioned between the contoured edge of the plunger and the bone graft, but which is adhered to the bone graft and remains at the graft receiving area following removal from the hollow tube. Furthermore, this graft retaining structure may also be employed with another tool, such as a graft packer, which is employed either before or after the hollow tube is removed from the graft receiving area.

In another embodiment, the one or more plungers corresponding to the one or more hollow tubes are positioned with distal ends near the proximate end of the horizontal tube before use, said plungers having a detent to retain plunger in ready position without undesired movement before surgeon chooses which one or more plungers to extend through hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design preferably comprises a hollow tubular member comprising a rounded edge rectangular shaft, which may be filled or is pre-filled with grafting material. The loading is carried out by the plunger. The rectangular design is preferable as it allows the largest surface area device to be placed into the annulotomy site of a disk, but in other embodiments may be formed similar to conventional round shafts.

The other preferred feature includes a laterally-mounted exit site for the graft material. The combination of this design feature allows direction-oriented dispersion of the graft material. This allows ejection of the graft material into an empty disk space as opposed to below the hollow tube, which would tend to impact the material and not allow its spread through a disk space.

Another feature of this design is that a rectangular design allows the user to readily determine the orientation of the device and thereby the direction of entry of the bone graft material into the surgical area. However, such a feature may be obtained alternatively through exterior markings or grooves on the exterior on the hollow tube. Such exterior grooves or markings would allow use of a range of cross-sections for the device, to include a square, circle, or oval while allowing the user to readily determine the orientation of the device relative to the direction of entry of the bone graft material into the surgical area.

A further feature of this design is that an anti-perforation footing or shelf is paced on the bottom of the hollow tube to prevent annular penetration and/or injury to the patient's abdomen or other anatomy adjacent the bone graft receiving area.

Another alterative embodiment to the design described herein includes a removable funnel attachment. This allows easy loading of the cannula with the funnel and with its removal easy visualization of the operating site without visual blockage through the microscope.

In another embodiment of the invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alterative embodiment to the design described herein includes a navigation aid on one or more surfaces of the tubular body to permit surgeon to know how far the device has been inserted or to ensure proper alignment relative to a transverse bone graft delivery site (i.e. disc space). Such capability is particularly important when the patient or surgical area is not positioned immediately below the surgeon, or multiple procedures are being performed. A navigation aid allows more immediate and reliable locating of the surgical area for receiving of bone graft material. In one embodiment, the hollow tube is scored or marked or provides some affirmative indication, actively or passively, to the surgeon to indicate degree of delivery of the material, e.g. bone graft material, to the delivery site, and/or position of the plunger element. For example, the exterior of the hollow tube could be color-coded and/or provided with bars. In another embodiment, a computer and/or electro-mechanical sensor or device is used to provide feedback to the surgeon to indicate degree of delivery of the material, e.g. amount of cc's of bone graft material, to the delivery site, and/or position of the plunger element.

In another alterative embodiment to the design described herein, the plunger could include an activation device, which is often in a liquid or semi-liquid state, and that may be injected once the semi-solid portion of the morphogenic protein has been displaced by the movement of the plunger through the tubular body. That is, the plunger pushes the dry material, and once completed has a bulb or other device on the usable end to insert the liquid portion of the activating agent through the inner lumen within the plunger to evacuate the liquid from the plunger and out an opening at the non-usable end of the plunger so as to contact the dry material already inserted into the disc space).

In one embodiment of the device, all or portions of the device are manufactured using 3-D printing techniques. In another embodiment, all or portions of the device are made by injection molding techniques.

In one embodiment, the ratio of the surface area of the bottom tip of the plunger is approximately half the surface area of the two lateral openings at the distal portion of the hollow tube.

In one embodiment, the device includes a supplemental means of gripping the device, such as a laterally extending cylindrically-shaped handle that engages the hollow tube.

In one embodiment, the material inserted into the hollow tube is a non-Newtonian fluid. In one embodiment, the device is adapted to accept and deliver compressible fluids. In another embodiment, the device is adapted to accept and deliver non-compressible fluids.

In one embodiment, the upper portion of plunger is fitted with one or more protrusions, which extends from the surface of the plunger so as to engage the upper surface of the hollow tube, to prevent the plunger from engaging the distal interior portion of the hollow tube. In one embodiment, the upper portion of plunger is fitted with one or more protrusions to prevent the plunger from engaging the apex of the hollow tube distal interior ramp surface.

In one embodiment, the funnel attaches to the upper portion of the hollow tube by a bayonet connection. In one embodiment, the funnel attaches to the upper portion of the hollow tube by an interference fit. In one embodiment, the funnel attaches to the upper portion of the hollow tube by a threaded connection. In one embodiment, the funnel attaches to the upper portion of the hollow tube by a slot/groove connection.

In one embodiment, the second end of hollow tube has one hollow tube distal opening. In one embodiment, the second end of hollow tube has two hollow tube distal openings located on opposite sides. In one embodiment, the second end of hollow tube has no more than two openings, the openings located on opposite sides.

In one embodiment, after bone graft material is delivered to a surgical site, a cavity approximately defined by the volume engaged by the device when inserted into the surgical site is left in the surgical site upon removal of the device from the surgical site. In one embodiment, the aforementioned cavity is then used as the site for insertion of a fusion cage.

Surprisingly, while conventional practice assumed that the amount of material that would be required, let alone desired, to fill a prepared disc space with bone paste (or BMP, etc.) would be roughly equivalent to the amount of material removed from such space prior to inserting a cage, a present inventor discovered that far more bone graft material can be—and should preferably be—inserted into such space to achieve desired fusion results. The reasons why this basic under appreciation for the volume of bone graft necessary to achieve optimal fusion results vary, but the clinical evidence arrived at via practice of the present invention compellingly demonstrates that more than doubling of the amount of bone graft material (and in some cases increasing the amount by 200%, 300% or 400% or more) than traditionally thought necessary or sufficient, is extremely beneficial to achieving desired results from fusion procedures.

The ramifications of this simple yet dramatic discovery (documented in part below) is part of the overall inventive aspect of the present invention, as it has been—to date—simply missed entirely by the practicing spine surgeons in the field. The prospect of reduced return surgeries, the reduction in costs, time, and physical suffering by patients, as well as the volume of legal complaints against surgeons and hospitals due to failed fusion results, is believed to be significant, as the evidence provided via use of the present invention indicates a vast reduction in the overall costs involved in both economic resources, as well as emotional capital, upon acceptance and wide-spread use of the present invention. Insurance costs should thus decrease as the present invention is adopted by the industry. While the costs of infusing increased amount of bone graft materials into the space of a patient's disc may at first appear to increase the costs of an individual operation, the benefits achieved thereby will be considerable, including the reduction of repeat surgeries to fix non-fused spines. Thus, regardless of the actual tools and devices employed to achieve the end result of attaining up to 100% more bone graft material being utilized in fusion operations, (as well as other surgeries where previously under-appreciated bone graft material delivery volumes have occurred) one important aspect of the present invention is directed to the appreciation of a previously unrecognized problem and the solution thereto, which forms part of the inventive aspects of the present invention described and claimed herein.

In one embodiment, at least twice the amount of disk material removed from a surgical site is replaced with bone graft material. In a preferred embodiment, at least three times the amount of disk material removed from a surgical site is replaced with bone graft material. In a most preferred embodiment, at least three and a half times the amount of disk material removed from a surgical site is replaced with bone graft material.

Experimental Results

The following experimental results are with respect to an apparatus and method for near-simultaneous and integrated delivery of bone graft material in a patient's spine. These results are sample results and are not intended to limit the invention.

Materials and Methods

During the time period from July 2010 through December 2012, a set of patients undergoing minimally invasive (MIS) transverse lumbar interbody fusion (T-LIF) at the L4-5 and/or L5-S1 levels were studied for disk material removed and BG delivered at each disk space during the surgical procedure. The diagnosis was spondylosis or spondylolisthesis in all patients. A total of 63 patients with an average age of 56 years were studied. There were 29 male and 34 female patients. Ninety-one disk spaces were analyzed. A single surgeon with the same surgical team performed all surgeries. The operations were carried out through a 22 mm cannula with microscopic control. The midline structures and spinous process attachments were left undisturbed. The disk space was debrided exhaustively using non-motorized, hand tools to bleeding subchondral bone. The debrided disk material was measured in a volumetric syringe. Bone Graft (BG) material consisting of silicated tricalcium phosphate granules and hyaluronic acid powder were mixed in a 1:1 ratio and local bone graft and bone marrow aspirate concentrate were added together to form a slurry. The slurry was measured volumetrically. Disk space mobilization and distraction was carried out with serial impaction of distractor tools until appropriate disk height was achieved. Distraction ranged from 8 mm to 14 mm, with the 10 mm or 12 mm height being most commonly observed.

The BG delivery tool of this disclosure was used to apply the BG slurry to the disk space. The embodiment had a rectangular cross section with the same footprint as a small fusion cage (8 mm×12 mm). The tapered tip was placed into the debrided disk space under microscopic control to allow for direct visualization, followed by the application of a snap-on funnel for loading the BG. The BG slurry was then placed in the funnel and the slurry was pushed into the disk space with the plunger. The biportal design of the delivery tool directed the slurry into the lateral areas of the prepared disk space, leaving a natural void for the fusion cage once the tool was removed. Once the disk space was filled entirely, the site of insertion was inspected for any BG material, which might have escaped the confines of the disk space. This material was excluded in the final measurement to ensure an accurate calculation of BG delivery. Removal of the delivery tool provided an unobscured path for the fusion cage to be applied.

A polyether ether ketone, hollow interbody fusion cage of the appropriate size was then placed into the disk space. A minimally invasive, bilateral pedicle screw/rod system was applied prior to wound closure. Average blood loss for the procedures was 127 ml±75 ml.

A two-tailed student's t-test was used to determine if any significant difference existed between the volumes of disk material removed at L4-5 versus L5-S1. The null hypothesis was that no significant difference existed between samples. Significance was set at $p<0.05$. The two-tailed t test was also used to determine whether a significant difference existed between volumes of BG delivery and disk material removed. The formula [(BG delivered+graft volume of the fusion cage)/ disk material removed] was used to generate the ratio of BG delivery versus disk material removed.

In order to compare the volume of disk material removed during a T-LIF procedure with a complete, surgical diskectomy, the volume of disk material removed during L5-S1 anterior lumbar diskectomy was measured volumetrically. The L5-S1 disk was harvested and measured for patients undergoing either anterior fusion or total disk replacement. The material removed consisted of anterior and posterior annulus as well as complete nuclectomy, and represented more tissue (in terms of the annuli) than would be typically removed in a T-LIF procedure. There were 29 anterior L5-S1 diskectomy patients. The age range, gender distribution and diagnosis were the same as the T-LIF patients.

All study patients were followed up with anterior/posterior radiographs and a physical examination at 4 weeks, 12 weeks, 26 weeks and 52 weeks post surgery.

A visual analog scale (VAS) for pain was obtained at each visit and an Oswestry Disability Index (ODI) was completed preoperatively and at 26 weeks postoperatively.

Results

There were 58 L4-5 disk spaces and 33 L5-S1 disk spaces evaluated. The average volumes of disk material harvested from L4-5 and L5-S1 were 4.1 ml±2.2 ml and 2.8 ml±1.9 ml, respectively. The p-value for the student's two-tailed t-test was equal to 0.01, revealing a significant difference in terms of disk material removed between L4-5 and L5-S1. The range of volume was less than 1 ml to 14.5 ml. The comparison between disk material removed and BG material inserted at L4-5 or at L5-S1 demonstrated a significant difference ($p<<0.001$).

Figure 34A:
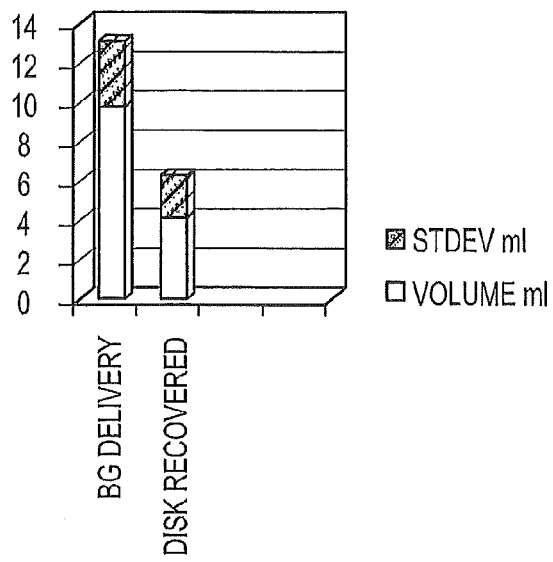
FIG. 34A is a bar graph describing experimental results of bone graft delivery and disk material removed for L4-5.
Figure 34B:
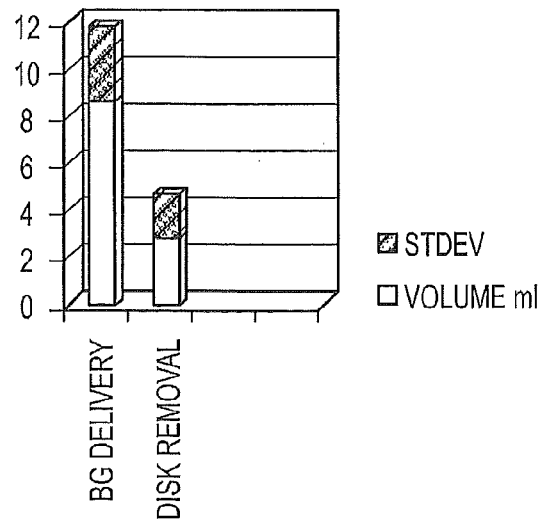
FIG. 34B is a bar graph describing experimental results of bone graft delivery and disk material removed for L5-S1.
Figures 35A, 35B:
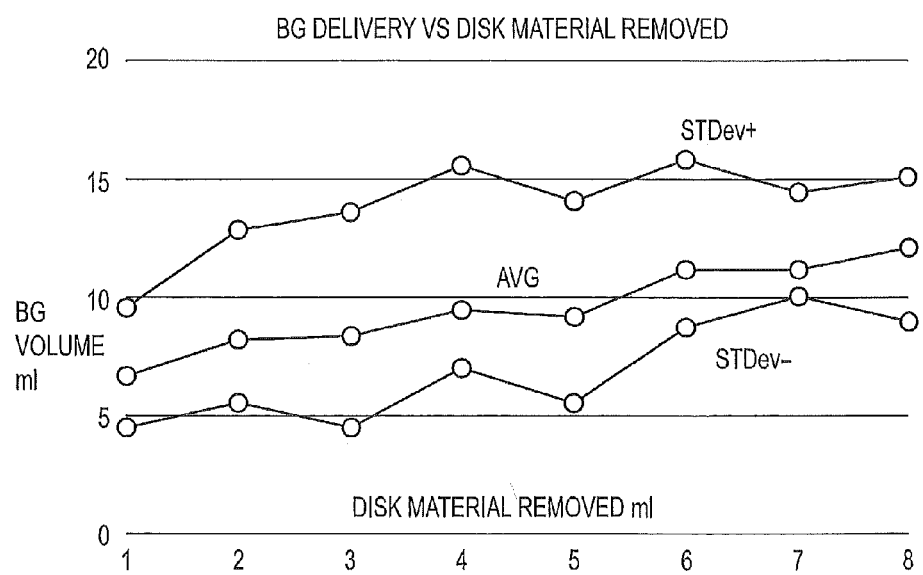
FIG. 35A is a table describing experimental results of bone graft delivery and disk material removed.
FIG. 35B is a graph of the table of FIG. 35A describing experimental results of bone graft delivery and disk material removed.
Figure 36:
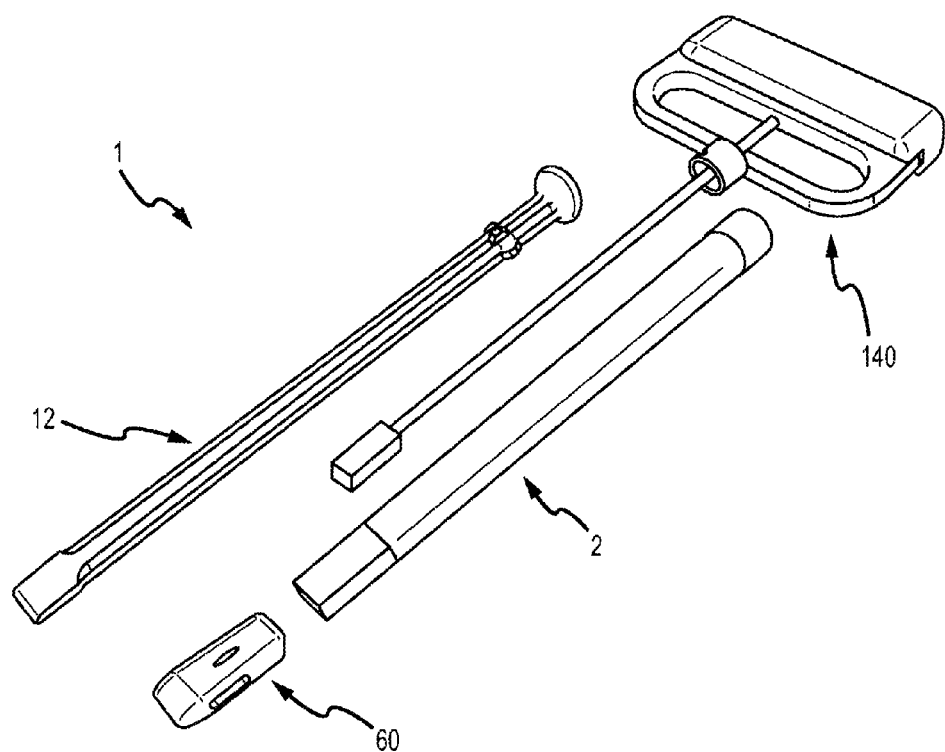
FIG. 36 is a front perspective exploded view of an integrated fusion cage and graft delivery device according to another embodiment.
Figure 37:
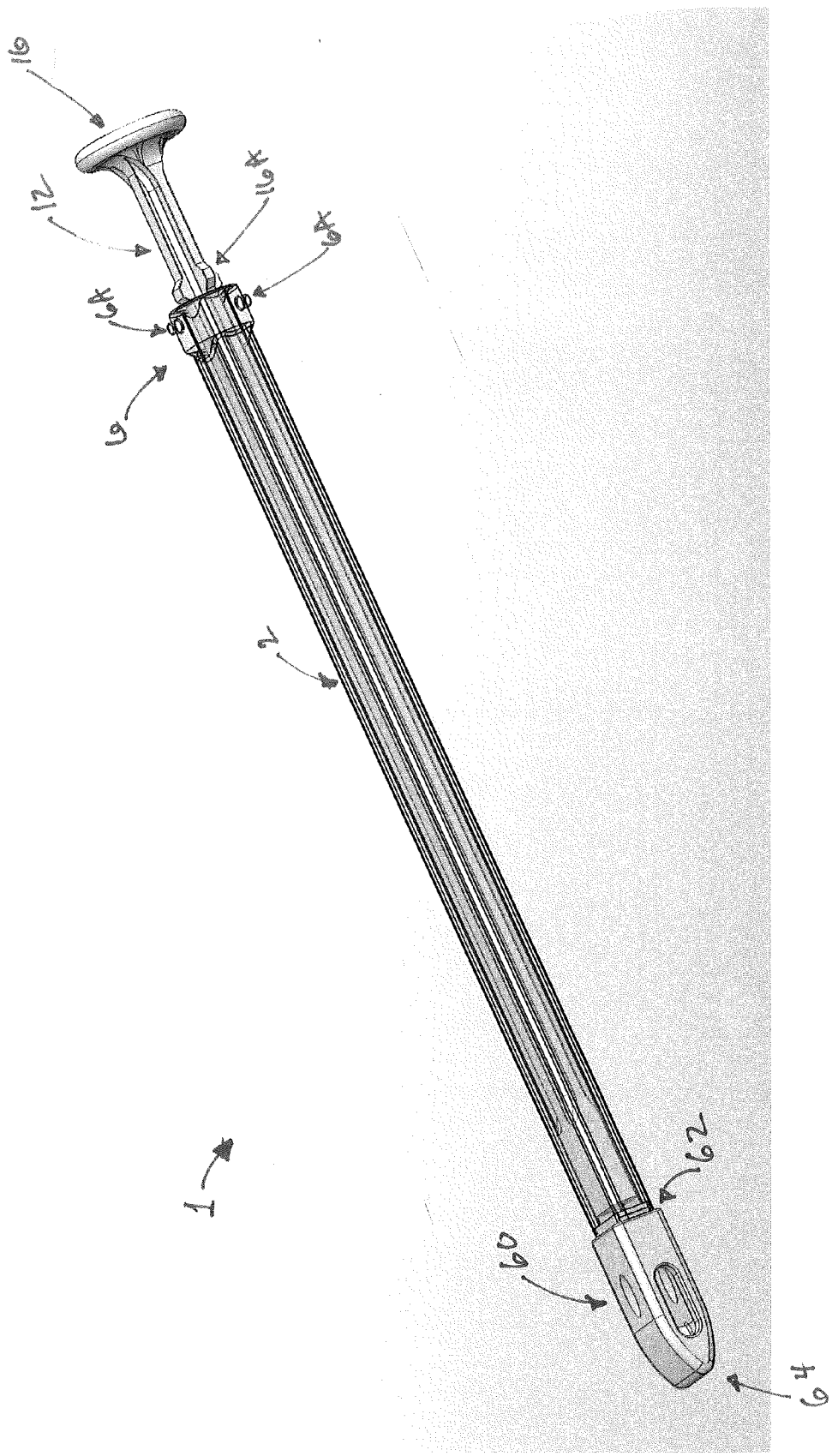
FIG. 37 is a front perspective view of the device of FIG. 36.
Figure 38:
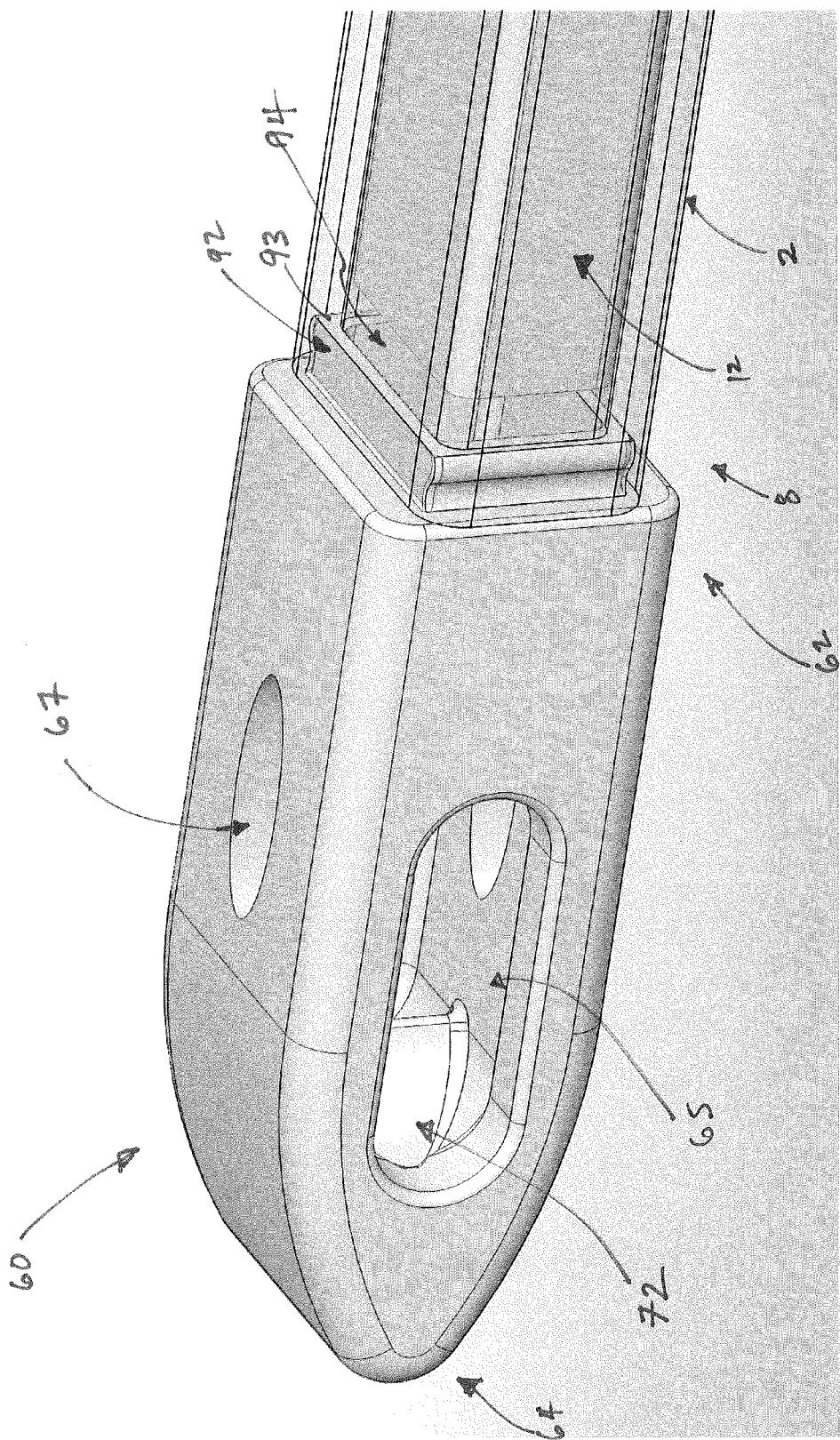
FIG. 38 is a closed-up front perspective view of the device of FIG. 36.
Figure 39:
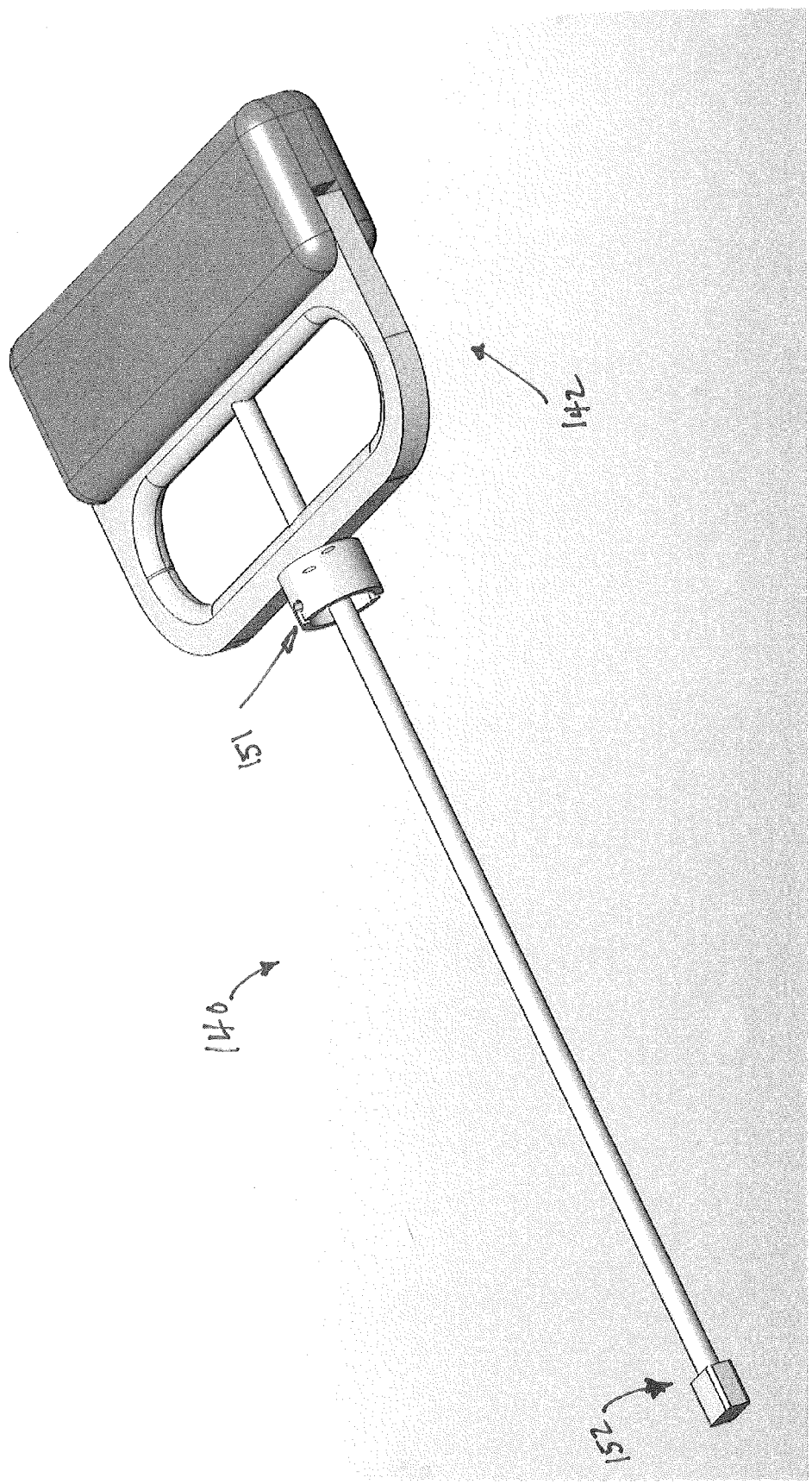
FIG. 39 is a front perspective view of the ejection tool element of the device of FIG. 36.

BG volume applied to L4-5 was 9.8 ml±3.3 ml. At L5-S1 it was 8.6 ml±3.2 ml. The p-value for the student's two-tailed t-test was equal to 0.07, trending to a significant difference in bone graft applied between L4-5 and L5-S1. The combined average was 9.2 ml±3.0 ml. The volume of BG applied ranged from 4.5 ml to 19 ml. The formula of [(BG delivered+graft volume of the fusion cage)/ disk material removed] generated a surprising result: The amount of disk material removed compared to the amount of BG placed in the disk space was not a 1:1 ratio, as would have been empirically expected. At L4-5 the ratio was 3.4±2.2 and at L5-S1 it was 4.7±2.7, as shown in FIGS. 34A-B, respectively. This was statistically significant with a p-value of 0.02. With respect to the entire study, the ratio of BG inserted relative to disk material removed revealed that on average 3.7±2.3 times as much BG was inserted into the disk space as disk material removed. This finding was even more dramatic with collapsed disk spaces where 1 ml of disk material harvest led to an average of 6.6 ml±0.9 ml of BG delivery, as shown in FIGS. 35A-B. The volume of BG delivery was asymptotically related to the volume of disk material removed with 12.3 m; of disk material being delivered to a disk where 8.0 ml of disk was removed, as shown in FIGS. 35A-B.

The average volume of disk material removed during a T-LIF diskectomy at L5-S1 was 3.2 ml and the average volume of disk material from the anterior L5-S1 diskectomy was 8.1 ml. Dividing the average T-LIF volume by the average anterior diskectomy (including annuli) volume revealed that on average 34% of the disk material was removed at the time of T-LIF at the L5-S1 disk space.

Because of the tapered tip of the BG delivery tool, it was possible to enter the most collapsed disk space without endplate injury. The delivery device did not jam with the application of the BG slurry. The removable funnel allowed direct visualization of the tool under the microscope without obscuring its tip during insertion. Because the delivery device applied BG out of its side portals, it provided a natural void for fusion cage insertion, and no cage jamming resulted during impaction. BG delivery using the described tool took a fraction of the time (less than 2 minutes) usually devoted to depositing BG to the disk space. There were no complications associated with the use of the BG delivery tool.

The average preoperative ODI measured 29±9 and the postoperative value was 21±8. A significant difference was not detected with p=0.06. The VAS similarly improved with pre-operative score measuring 7.5±1.5 and postoperative score 4.0±2.5. The postoperative VAS was statistically significant relative to the corresponding preoperative value with p<0.05. Pseudoarthrosis developed in 7 disks in 4 patients (7.6%). The patients with 2-level pseudoarthrosis had a diagnosis of hypothyroidism. This diagnosis was also present in one of the single level pseudoarthrosis patients. The remaining pseudoarthrosis patients did not have discernable risk factors (diabetes, tobacco consumption or obesity).

Discussion

There is substantial variation in fusion rates after T-LIF surgery with pseudoarthrosis rates varying from 23.1% to 2.9%. The reasons for the range of successful arthrodesis vary from surgical technique, including BG preparation and application, to the way in which a pseudoarthrosis is diagnosed— direct surgical exploration or by radiographic means. Reason would dictate that the volume of BG delivered to a prepared disk space would contribute positively to successful arthrodesis with inadequate grafting leading to pseudoarthrosis. Using hand tools and the goal of disk space debridement, a conservative estimate of 34% of disk removal was observed in this study at the L5-S1 level. This substantial difference represents the different goals of the procedures and provides a baseline for general disk space debridement for T-LIF procedures.

The statistically significant difference between the amount of disk material removed from L4-5 versus L5-S1 correlates with the commonly observed radiographic finding of disk height at L4-5 being greater than that of L5-S1. Likewise, BG delivery to L4-5 was greater relative to the L5-S1 disk space. Although direct volume of BG insertion was greater in L4-5 relative to L5-S1, the ratio (BG delivered/disk material removed) was higher at L5-S1 (4.7±2.7) than at L4-5 (3.4±2.2). This was a statistically significant difference (p<0.02) and corresponds with the more collapsed disk spaces demonstrating a higher percentage of BG delivery (see FIGS. 34A-B).

On average, 3.7 times as much bone graft was applied to the debrided disk space relative to disk material removed. This is explained by the fact that the disk space was collapsed at the time of diskectomy, and then distracted and mobilized during the preparation process to a distracted height. This suggests that relying on an empiric 1:1 ratio of disk removal to BG insertion grossly under-fills the disk space and would be an important contributor to pseudoarthrosis. This is an especially important consideration in the most collapsed disk spaces since distraction to appropriate height in a non-collapsed disk reduces the ratio to 8:12.3 (see FIG. 35A) or a 1:1.4 ratio.

The BG slurry used in this study consisted of a mixture of granular material and liquid. This combination of materials does not behave as a typical, Newtonian (non-compressible) fluid. A non-Newtonian fluid will exude its fluid component as it is compressed, and the residual granular BG material occludes a conventional, cylindrical BG delivery device.

The BG delivery tool in this study revealed a number of advantages in that it allowed for BG application in collapsed disc spaces due to its wedged tip, a process which is not possible with round-ended injection cannulas. The increased cross sectional footprint relative to a round cannula allowed considerably less friction of non-Newtonian fluid material through the cannula, resulting in an increase in the BG flow dynamics, and eliminating jamming due to BG impaction. It is estimated that changing the cross-sectional area from 8 mm×8 mm to 8 mm×12 mm improves the flow dynamics of a non-Newtonian fluid by 40%. The two sites for BG extrusion at the sides of the cannula tip double the exit zone surface area, further decreasing the resistance to flow of the granular mixture. The removable funnel allowed direct visualization of the cannula as it was applied to the disk space without being obscured by the funnel. The biportal expression of the BG material allowed graft inoculation of all prepared areas of the disk space and left a void for the fusion cage. The applied BG delivery tool allowed refilling of the cannula without having to remove the device, resulting in decreased potential trauma to the adjacent nerve tissue.

The fusion rate in this study was 92.4% with three of the pseudoarthrosis patients having a diagnosis of hypothyroidism. This may be related to abnormalities in bone metabolism associated in patients with endocrinopathy. The other pseudoarthrosis patients did not have apparent risk factors. Postoperative pain scores and functional improvement correlated with progression to arthrodesis.

In summary, preparation of the disk spaces at L4-S1 can deliver 34% of the disk volume during debridement. BG delivery was on average 3.7 times the volume of disk removal with a relatively higher ratio of BG being delivered to the more collapsed disk spaces. A novel BG delivery device can be used to dispense a volume of BG to the disk space that is capable of filling the entire debrided area in an efficient and safe fashion. This should allow for maximization of arthrodesis potential, increase patient safety, and decrease operative time.

To provide further clarity to the Detailed Description provided herein in the associated drawings, the following list of components and associated numbering are provided as follows:

| Reference No. | Component |
|---|---|
| 1 | Integrated fusion cage and graft delivery device |
| 2 | Hollow tube |
| 3 | Hollow tube first exterior surface |
| 4 | Opening (of Hollow tube) |
| 5 | Hollow tube second exterior surface |
| 6 | First end (of Hollow tube) |
| 6A | Knob |
| 7 | Hollow tube first distal opening |
| 8 | Second end (of Hollow tube) |
| 8A | Hollow tube cage clamp |
| 8B | Hollow tube cage clamp radial surface |
| 9 | Hollow tube distal interior ramp |
| 9A | Hollow tube distal interior ramp surface |
| 10 | Curved surface (of Hollow tube) |
| 10A | Curved interior surface (of Hollow tube) |
| 11 | Footing (of Hollow tube) |
| 12 | Plunger |
| 13 | Plunger distal first surface |
| 14 | Plunger distal second surface |
| 15 | Plunger distal third surface |
| 16 | Handle (of Plunger) |
| 16A | Plunger stop |
| 17 | Plunger medial portion |
| 18 | Second end (of Plunger) |
| 19 | Horizontal surface (of Plunger) |
| 20 | Curved surface (of Plunger) |
| 30 | Funnel |
| 32 | Sleeve (of Funnel) |
| 34 | Opening (of Funnel) |
| 40 | Disc space |
| A | Height of opening (in Hollow tube) |
| B | Width of opening (in Hollow tube) |
| 50 | Wedge-shaped Second end (of Hollow tube) |
| 52 | Wedge-shaped Second end (of Plunger) |
| 60 | Fusion Cage |
| 61 | Fusion cage surface texture |
| 62 | Fusion Cage First End |
| 64 | Fusion Cage Second End |
| 65 | Fusion Cage First Opening Pair |
| 66 | Fusion Cage First End Opening |
| 67 | Fusion Cage Second Opening Pair |
| 68 | Fusion Cage Medial Opening |
| 69 | Fusion Cage Lateral Opening |
| 70 | Fusion Cage Medial Surfaces |
| 72 | Fusion Cage Internal Ramps |
| 80 | Hollow Tube Locking Tabs |
| 82 | Fusion Cage Locking Slots |
| 90 | Break-off Collar |
| 92 | Fusion Cage Collar |
| 93 | Fusion Cage Collar Face |
| 94 | Fusion Cage Collar Cavity |
| 96 | Fusion Cage Tab Extension |
| 97 | Fusion Cage Tab Extension Latch |
| 100 | Connector Conduit |
| 102 | Connectors |
| 110 | ALIF Fusion Cage |
| 112 | ALIF Fusion Cage Portals |
| 114 | ALIF Fusion Cage Chamber |
| 116 | ALIF Fusion Cage Break-off Collar |
| 120 | D-LIF Fusion Cage |
| 122 | D-LIF Fusion Cage Portals |
| 124 | D-LIF Fusion Cage Chamber |
| 126 | D-LIF Fusion Cage Break-off Collar |
| 130 | Vertebrectomy Fusion Cage |
| 132 | Vertebrectomy Fusion Cage Porous Wall Portion |
| 134 | Vertebrectomy Fusion Cage Chamber |
| 136 | Vertebrectomy Fusion Cage Break-off Collar |
| 138 | Vertebrectomy Fusion Cage Impervious Wall Portion |

-continued

| Reference No. | Component |
|---|---|
| 140 | Ejection Tool |
| 142 | Ejection Tool First (Proximal) End |
| 143 | Ejection Tool Stop |
| 144 | Ejection Tool Cover |
| 145 | Ejection Tool Cover Cavity |
| 146 | Spring Cover |
| 147 | Spring Cover Attachment |
| 148 | Spring |
| 149 | Ejection Tool Wings |
| 150 | Ejection Tool Wings Cavity |
| 151 | Ejection Tool L-cut |
| 152 | Ejection Tool Second (Distal) End |
| 160 | Ejection Tool Rod |

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bone graft insertion apparatus comprising:
a hollow tube constructed to receive bone graft, said hollow tube having an extended axis and a proximal end and a distal end, said hollow tube having a rectangular interior cross-section from said proximal end to said distal end, said distal end having a tapered tip interior surface with a terminus and two lateral oval-shaped openings having an upper and a lower end located on opposite lateral sides of said distal end, said tapered tip interior surface extending into said hollow tube and said terminus positioned adjacent to said lateral oval-shaped openings, said hollow tube of single-piece construction;
a plunger adapted for inserting into said proximal end of said hollow tube along the extended axis, said plunger having a distal end exterior surface of rectangular cross-section contoured to said interior cross-section of said hollow tube, said plunger of single-piece construction with a distal exterior tip, said plunger distal end exterior surface of rectangular cross-section forming a substantially congruent fit with said hollow tube rectangular interior cross-section, wherein said hollow tube and said plunger are configured to deliver bone graft material to a graft receiving area through said lateral oval-shaped openings, said plunger having an axial length at least sufficient wherein at a least a portion of said plunger distal end is positioned adjacent to said one or more lateral openings when fully inserted into said hollow tube, said one or more lateral openings substantially precluding the delivery of bone graft material directly along said axis of said hollow tube, said plunger precluded from rotating when inserted into said hollow tube;

wherein said distal exterior tip of said plunger is configured to remain always proximal to the tapered distal end of said hollow tube.

2. The apparatus according to claim 1, wherein said tapered tip interior surface is symmetrical about an axial centerline of the hollow tube.

3. The apparatus according to claim 1, wherein said tapered tip interior surface comprises a curved surface.

4. The apparatus according to claim 1, wherein said distal end of said hollow tube comprises an exterior curved surface.

5. The apparatus according to claim 1, further comprising:
a detachable funnel connected to said proximal end of said hollow tube, wherein said detachable funnel facilitates insertion of said bone graft into said hollow tube.

6. The apparatus of claim 1, wherein said hollow tube has a length and said one or more lateral openings are solely located on a lower half of said length.

7. The apparatus of claim 1, wherein said plunger distal tip forms a planar lower surface.

8. The apparatus of claim 1, wherein said distal end of at least one of said plunger and said hollow tube are constructed of material more flexible than material comprising said proximal end of said hollow tube.

9. The apparatus of claim 1, wherein said hollow tube is preloaded with one of bone graft and bone morphogenic protein.

10. A combination bone graft insertion and implant insertion apparatus comprising:
a hollow tube constructed to receive bone graft, said hollow tube having an extended axis and a proximal end and a distal end, said hollow tube having a uniform interior cross-section from said proximal end to said distal end, said hollow tube of single-piece construction;
a substantially hollow implant detachably interconnected to the distal end of the hollow tube, said implant constructed to receive bone graft from said hollow tube, said implant having at least two openings having an upper and a lower end located on opposite lateral sides of said implant, said implant having striations on a plurality of implant surfaces, said implant having a tapered distal end which spans the extended axis and forms the most distal end of the combination bone graft insertion and implant insertion apparatus; and
a plunger adapted for inserting into said proximal end of said hollow tube along the extended axis, said plunger having a distal end exterior surface of cross-section contoured to said interior cross-section of said hollow tube, said plunger of single-piece construction with a distal exterior tip, said plunger distal end exterior surface of cross-section forming a substantially congruent fit with said hollow tube uniform interior cross-section,
wherein said hollow tube, said substantially hollow implant and said plunger are configured to deliver bone graft material to a graft receiving area into the interior of the substantially hollow implant and through the at least two openings of said substantially hollow implant when the plunger is advanced from the proximal end to the distal end of the hollow tube along the extended axis,
wherein the distal exterior tip of said plunger is configured to remain always proximal to the tapered distal end of said substantially hollow implant when said plunger is inserted into said hollow tube and said substantially hollow implant is attached to said hollow tube.

11. The apparatus of claim 10, wherein said hollow tube has a length and said one or more lateral openings are solely located on a lower half of said length.

12. The apparatus of claim 10, wherein said one or more lateral openings substantially preclude the delivery of bone graft material directly along said axis of said hollow tube, said plunger precluded from rotating when inserted into said hollow tube.

13. The apparatus of claim 10, wherein said hollow tube is preloaded with one of bone graft and bone morphogenic protein.

14. The apparatus of claim 1, wherein said distal end of said hollow tube is configured to detachably interconnect to a detachable hollow implant, said implant having a tapered distal end which spans the extended axis and forms the most distal end of the bone graft insertion apparatus when attached to said hollow tube, wherein said distal exterior tip of said plunger is configured to remain always proximal to the tapered distal end of said hollow implant when said plunger is inserted into said hollow tube and said hollow implant is attached to said hollow tube.

15. A combination bone graft delivery and implant insertion apparatus for integrated delivery of bone graft material to a spinal surgical site and for disposing an implant to a spinal surgical site, comprising:
a hollow tube constructed to receive bone graft, said hollow tube having an extended axis and a proximal end and a distal end, said hollow tube having a uniform interior cross-section from said proximal end to said distal end;
a substantially hollow implant for use in spinal surgery detachably interconnected to the distal end of the hollow tube, said implant constructed to receive bone graft from said hollow tube and constructed to be disposed in a spinal surgical site, said implant having at
least two pairs of implant openings, each pair of implant openings located on opposite sides of said implant, said implant configured to fit between a spinal disk space of a spinal surgical site, said implant having striations on a plurality of surfaces adjacent at least one pair of the at least two pairs of implant openings, said hollow implant having a tapered distal end; and
a plunger adapted for inserting into said proximal end of said hollow tube and deliver bone graft to an interior of the implant, said plunger having a distal end exterior surface of cross-section contoured to said interior cross-section of said hollow tube, said plunger distal end exterior surface of cross-section forming a substantially congruent fit with said hollow tube uniform interior cross-section, wherein said hollow tube, said implant and said plunger are configured to deliver the bone graft material to the spinal surgical site through the at least two pairs of implant openings of said implant after passing through the interior of the implant, wherein when bone graft material is within said hollow tube, said bone graft material can be delivered to the interior of the implant and to the spinal surgical site, wherein the implant is detached from the hollow tube and disposed in the spinal surgical site, wherein the spinal surgical site comprises a spinal disk space.

16. The apparatus of claim 15, wherein said striations are disposed on implant exterior surfaces defining two opposite edges of the implant openings on at least one pair of the at least two pairs of implant openings, wherein said implant has at least six implant openings.

17. The apparatus of claim 15, wherein said hollow tube is preloaded with one of bone graft and bone morphogenic protein.

\* \* \* \* \*